United States Patent
Hua

(10) Patent No.: US 11,160,580 B2
(45) Date of Patent: Nov. 2, 2021

(54) SYSTEMS AND METHODS FOR PEDICLE SCREW STABILIZATION OF SPINAL VERTEBRAE

(71) Applicant: SPINE 23, INC., Hillsborough, CA (US)

(72) Inventor: Sherwin Hua, Hillsborough, CA (US)

(73) Assignee: SPINE23 INC., Campbell, CA (US)

( * ) Notice: Subject to any disclaimer, the term of this patent is extended or adjusted under 35 U.S.C. 154(b) by 0 days.

(21) Appl. No.: 16/855,941

(22) Filed: Apr. 22, 2020

(65) Prior Publication Data

US 2021/0068870 A1 Mar. 11, 2021

Related U.S. Application Data

(60) Provisional application No. 62/838,231, filed on Apr. 24, 2019.

(51) Int. Cl.
*A61B 17/70* (2006.01)

(52) U.S. Cl.
CPC ...... *A61B 17/7032* (2013.01); *A61B 17/7091* (2013.01)

(58) Field of Classification Search
CPC ............ A61B 17/7074; A61B 17/7077; A61B 17/7079; A61B 17/708; A61B 17/7083; A61B 17/7085; A61B 17/7091
See application file for complete search history.

(56) References Cited

U.S. PATENT DOCUMENTS

| | | |
|---|---|---|
| 4,448,191 A | 5/1984 | Rodnyansky et al. |
| 5,092,866 A | 3/1992 | Breard et al. |
| 5,242,443 A | 9/1993 | Kambin |
| 5,300,076 A | 4/1994 | Leriche |
| 5,306,275 A | 4/1994 | Bryan |
| 5,324,316 A | 6/1994 | Schulman et al. |
| 5,672,175 A | 9/1997 | Martin |
| 5,728,097 A | 3/1998 | Mathews |
| 5,865,842 A | 2/1999 | Knuth et al. |
| 5,938,689 A | 8/1999 | Fischell et al. |

(Continued)

FOREIGN PATENT DOCUMENTS

| | | |
|---|---|---|
| CN | 2782035 Y | 5/2006 |
| CN | 1972639 A | 5/2007 |

(Continued)

OTHER PUBLICATIONS

"MANTIS™ Spinal System Surgical Technique", Stryker Spine, Literature No. TLMANST06071, 2006, (Brochure) in 48 pages.

(Continued)

*Primary Examiner* — Lynnsy M Summitt
(74) *Attorney, Agent, or Firm* — Knobbe, Martens, Olson & Bear, LLP

(57) ABSTRACT

The present application is directed to various spinal stabilization systems and methods. The systems can include a plurality of spinal screws each having a screw head. The systems can also include one or more wires directly or indirectly connected to the screw heads of each of the spinal screws. The systems can also include one or more towers that is configured to be removably advanced over the wires. The spinal implant of the system can be configured to be positioned within the screw heads of the plurality of spinal screws.

17 Claims, 47 Drawing Sheets

(56) References Cited

U.S. PATENT DOCUMENTS

| | | |
|---|---|---|
| 5,980,521 A | 11/1999 | Montague et al. |
| 6,011,991 A | 1/2000 | Mardirossian |
| 6,016,449 A | 1/2000 | Fischell et al. |
| 6,051,017 A | 4/2000 | Loeb et al. |
| 6,090,113 A | 7/2000 | Le Couedic et al. |
| 6,175,764 B1 | 1/2001 | Loeb et al. |
| 6,181,965 B1 | 1/2001 | Loeb et al. |
| 6,185,452 B1 | 2/2001 | Schulman et al. |
| 6,208,894 B1 | 3/2001 | Schulman et al. |
| 6,235,028 B1 | 5/2001 | Brumfield et al. |
| 6,240,316 B1 | 5/2001 | Richmond et al. |
| 6,427,086 B1 | 7/2002 | Fischell et al. |
| 6,482,182 B1 | 11/2002 | Carroll et al. |
| 6,485,491 B1 | 11/2002 | Farris et al. |
| 6,493,592 B1 | 12/2002 | Leonard et al. |
| 6,530,929 B1 | 3/2003 | Justis et al. |
| 6,546,277 B1 | 4/2003 | Franck et al. |
| 6,549,810 B1 | 4/2003 | Leonard et al. |
| 6,582,441 B1 | 6/2003 | He et al. |
| 6,597,954 B1 | 7/2003 | Pless et al. |
| 6,622,051 B1 | 9/2003 | Bishay et al. |
| 6,623,490 B1 | 9/2003 | Crane et al. |
| 6,711,430 B1 | 3/2004 | Ferris et al. |
| 6,731,976 B2 | 5/2004 | Penn et al. |
| 6,735,475 B1 | 5/2004 | Whitehurst et al. |
| 6,782,292 B2 | 8/2004 | Whitehurst |
| 6,788,975 B1 | 9/2004 | Whitehurst et al. |
| 6,793,656 B1 | 9/2004 | Mathews |
| 6,795,737 B2 | 9/2004 | Gielen et al. |
| 6,819,956 B2 | 11/2004 | Dilorenzo |
| 6,830,544 B2 | 12/2004 | Tanner |
| 6,862,479 B1 | 3/2005 | Whitehurst et al. |
| 6,871,098 B2 | 3/2005 | Nuttin |
| 6,916,320 B2 | 7/2005 | Michelson |
| 6,922,590 B1 | 7/2005 | Whitehurst |
| 6,929,606 B2 | 8/2005 | Ritland |
| 6,950,707 B2 | 9/2005 | Whitehurst |
| 6,959,215 B2 | 10/2005 | Gliner et al. |
| 6,970,741 B1 | 11/2005 | Whitehurst et al. |
| 6,990,377 B2 | 1/2006 | Gliner et al. |
| 7,003,352 B1 | 2/2006 | Whitehurst |
| 7,006,859 B1 | 2/2006 | Osorio et al. |
| 7,008,422 B2 | 3/2006 | Foley et al. |
| 7,011,660 B2 | 3/2006 | Sherman et al. |
| 7,013,177 B1 | 3/2006 | Whitehurst et al. |
| 7,063,708 B2 | 6/2006 | Gibson et al. |
| 7,063,725 B2 | 6/2006 | Foley |
| 7,066,961 B2 | 6/2006 | Michelson |
| 7,083,621 B2 | 8/2006 | Shaolian et al. |
| 7,103,408 B2 | 9/2006 | Haller et al. |
| 7,107,103 B2 | 9/2006 | Schulman et al. |
| 7,146,217 B2 | 12/2006 | Firlik et al. |
| 7,151,961 B1 | 12/2006 | Whitehurst et al. |
| 7,158,333 B1 | 1/2007 | Sutardja et al. |
| 7,167,751 B1 | 1/2007 | Whitehurst et al. |
| 7,174,212 B1 | 2/2007 | Klehn et al. |
| 7,179,225 B2 | 2/2007 | Shluzs et al. |
| 7,179,261 B2 * | 2/2007 | Sicvol ............... A61B 17/7032 606/86 A |
| 7,187,967 B2 | 3/2007 | Kennedy |
| 7,188,626 B2 | 3/2007 | Foley et al. |
| 7,209,787 B2 | 4/2007 | Dilorenzo |
| 7,221,981 B2 | 5/2007 | Gliner |
| 7,236,830 B2 | 6/2007 | Gliner |
| 7,236,831 B2 | 6/2007 | Firlik et al. |
| 7,250,052 B2 | 7/2007 | Landry et al. |
| 7,255,686 B2 | 8/2007 | Putz |
| 7,282,064 B2 | 10/2007 | Chin |
| 7,283,856 B2 | 10/2007 | Boling |
| 7,292,890 B2 | 11/2007 | Whitehurst et al. |
| 7,299,096 B2 | 11/2007 | Balzer et al. |
| 7,302,298 B2 | 11/2007 | Lowry et al. |
| 7,305,268 B2 | 12/2007 | Gliner et al. |
| 7,306,603 B2 | 12/2007 | Boehm, Jr. et al. |
| 7,326,210 B2 | 2/2008 | Jahng et al. |
| D565,735 S | 4/2008 | Washbon |
| 7,353,064 B2 | 4/2008 | Gliner et al. |
| 7,376,468 B2 | 5/2008 | King et al. |
| 7,406,105 B2 | 7/2008 | Delmain et al. |
| 7,465,306 B2 | 12/2008 | Pond, Jr. et al. |
| 7,468,064 B2 | 12/2008 | Bruneau et al. |
| 7,491,208 B2 | 2/2009 | Pond, Jr. et al. |
| 7,491,218 B2 | 2/2009 | Landry et al. |
| 7,497,869 B2 | 3/2009 | Justis |
| 7,520,879 B2 | 4/2009 | Justis et al. |
| 7,527,638 B2 | 5/2009 | Anderson et al. |
| 7,547,318 B2 | 6/2009 | Birkmeyer et al. |
| 7,575,581 B2 | 8/2009 | Lovell |
| 7,588,575 B2 | 9/2009 | Colleran et al. |
| 7,588,588 B2 | 9/2009 | Spitler et al. |
| 7,604,658 B2 | 10/2009 | Wilson et al. |
| 7,666,189 B2 | 2/2010 | Gerber et al. |
| 7,686,814 B2 | 3/2010 | Lim et al. |
| 7,691,132 B2 | 4/2010 | Landry et al. |
| 7,708,763 B2 | 5/2010 | Selover et al. |
| 7,717,944 B2 | 5/2010 | Foley et al. |
| 7,736,370 B2 | 6/2010 | Sweeney |
| 7,749,233 B2 | 7/2010 | Farr et al. |
| 7,758,584 B2 | 7/2010 | Bankoski et al. |
| 7,758,617 B2 | 7/2010 | Lott et al. |
| 7,763,055 B2 | 7/2010 | Foley |
| 7,776,051 B2 | 8/2010 | Colleran et al. |
| 7,824,410 B2 | 11/2010 | Simonson et al. |
| 7,846,093 B2 | 12/2010 | Gorek et al. |
| 7,875,031 B2 * | 1/2011 | Chin ............... A61B 17/7037 606/86 A |
| 7,937,160 B2 | 5/2011 | Garabedian et al. |
| 7,947,045 B2 | 5/2011 | Hestad et al. |
| 7,955,355 B2 | 6/2011 | Chin |
| 8,043,343 B2 | 10/2011 | Miller et al. |
| 8,052,720 B2 | 11/2011 | Kuester et al. |
| 8,075,565 B2 * | 12/2011 | Wilcox ............... A61B 17/7079 606/86 A |
| 8,216,282 B2 * | 7/2012 | Hua ............... A61B 17/7001 606/264 |
| 8,333,770 B2 * | 12/2012 | Hua ............... A61B 17/7032 606/86 A |
| 8,366,714 B2 * | 2/2013 | Jones ............... A61B 17/7083 606/86 A |
| 8,545,541 B2 | 10/2013 | Hua |
| 8,556,940 B2 | 10/2013 | Hua |
| 8,721,691 B2 | 5/2014 | Hua |
| 9,179,875 B2 | 11/2015 | Hua |
| 9,198,698 B1 | 12/2015 | Doose et al. |
| 9,402,661 B2 * | 8/2016 | Reitblat ............... A61B 17/7035 |
| 9,642,552 B2 | 5/2017 | Hua |
| 9,820,668 B2 | 11/2017 | Hua |
| 9,877,846 B2 * | 1/2018 | Dvorak ............... A61B 17/7077 |
| 9,919,146 B2 | 3/2018 | Hua |
| 10,004,543 B2 * | 6/2018 | Stokes ............... A61B 17/7085 |
| 10,194,960 B1 * | 2/2019 | Hammann ......... A61B 17/7079 |
| 10,406,351 B2 | 9/2019 | Hua |
| 10,660,631 B1 * | 5/2020 | Boesel ............... A61B 17/0206 |
| 10,702,314 B2 | 7/2020 | Reitblat et al. |
| 10,736,533 B2 | 8/2020 | Hua |
| 10,973,551 B2 | 4/2021 | Hua |
| 2001/0003156 A1 | 6/2001 | Gill |
| 2002/0151770 A1 | 10/2002 | Noll et al. |
| 2003/0028072 A1 | 2/2003 | Fischell et al. |
| 2003/0040753 A1 | 2/2003 | Daum et al. |
| 2003/0093129 A1 | 5/2003 | Nicolelis et al. |
| 2003/0171750 A1 | 9/2003 | Chin |
| 2003/0208203 A1 | 11/2003 | Lim et al. |
| 2003/0233125 A1 | 12/2003 | Kaplan et al. |
| 2003/0233126 A1 | 12/2003 | Kaplan et al. |
| 2004/0030236 A1 | 2/2004 | Mazzochi et al. |
| 2004/0082961 A1 | 4/2004 | Teitelbaum |
| 2004/0088024 A1 | 5/2004 | Firlik et al. |
| 2004/0147928 A1 | 7/2004 | Landry et al. |
| 2004/0186532 A1 | 9/2004 | Tadlock |
| 2004/0225335 A1 | 11/2004 | Whitehurst et al. |
| 2004/0243130 A1 | 12/2004 | Biscup |
| 2004/0243207 A1 | 12/2004 | Olson et al. |
| 2005/0075680 A1 | 4/2005 | Lowry et al. |

(56) References Cited

U.S. PATENT DOCUMENTS

| | | |
|---|---|---|
| 2005/0101954 A1 | 5/2005 | Simonson |
| 2005/0102006 A1 | 5/2005 | Whitehurst et al. |
| 2005/0131311 A1 | 6/2005 | Leuthardt et al. |
| 2005/0131422 A1 | 6/2005 | Anderson et al. |
| 2005/0137652 A1 | 6/2005 | Cauller et al. |
| 2005/0182453 A1 | 8/2005 | Whitehurst et al. |
| 2005/0192570 A1 | 9/2005 | Jackson |
| 2005/0192589 A1 | 9/2005 | Raymond et al. |
| 2005/0228380 A1 | 10/2005 | Moore et al. |
| 2005/0245969 A1 | 11/2005 | Loeb |
| 2005/0251237 A1 | 11/2005 | Kuzma et al. |
| 2005/0283203 A1 | 12/2005 | Flaherty et al. |
| 2006/0005845 A1 | 1/2006 | Karr et al. |
| 2006/0030872 A1 | 2/2006 | Culbert et al. |
| 2006/0089652 A1 | 4/2006 | Eckman |
| 2006/0095035 A1 | 5/2006 | Jones et al. |
| 2006/0111767 A1 | 5/2006 | Olson et al. |
| 2006/0173522 A1 | 8/2006 | Osorio |
| 2006/0184143 A1 | 8/2006 | Jolly et al. |
| 2006/0195154 A1 | 8/2006 | Jaax et al. |
| 2006/0206165 A1 | 9/2006 | Jaax et al. |
| 2006/0212087 A1 | 9/2006 | Haller et al. |
| 2006/0212090 A1 | 9/2006 | Lozano et al. |
| 2006/0212091 A1 | 9/2006 | Lozano et al. |
| 2006/0234279 A1 | 10/2006 | Miller et al. |
| 2006/0235279 A1 | 10/2006 | Hawkes et al. |
| 2006/0241600 A1 | 10/2006 | Ensign et al. |
| 2006/0241717 A1 | 10/2006 | Whitehurst et al. |
| 2006/0264942 A1 | 11/2006 | Lim et al. |
| 2006/0264962 A1 | 11/2006 | Chin et al. |
| 2007/0016188 A1 | 1/2007 | Boehm, Jr. et al. |
| 2007/0016198 A1 | 1/2007 | Boehm, Jr. et al. |
| 2007/0016199 A1 | 1/2007 | Boehm, Jr. et al. |
| 2007/0021800 A1 | 1/2007 | Whitehurst et al. |
| 2007/0032718 A1 | 2/2007 | Shults et al. |
| 2007/0032839 A1 | 2/2007 | Parramon et al. |
| 2007/0073294 A1* | 3/2007 | Chin ............... A61B 17/7091 606/86 A |
| 2007/0078460 A1 | 4/2007 | Frigg et al. |
| 2007/0078503 A1 | 4/2007 | Kuzma et al. |
| 2007/0088417 A1 | 4/2007 | Schouenborg |
| 2007/0093814 A1 | 4/2007 | Callahan, II et al. |
| 2007/0100393 A1 | 5/2007 | Whitehurst et al. |
| 2007/0106143 A1 | 5/2007 | Flaherty |
| 2007/0123954 A1 | 5/2007 | Gielen et al. |
| 2007/0135867 A1 | 6/2007 | Klosterman et al. |
| 2007/0167954 A1 | 7/2007 | Sicvol et al. |
| 2007/0173733 A1 | 7/2007 | Le et al. |
| 2007/0191840 A1 | 8/2007 | Pond, Jr. et al. |
| 2007/0219554 A1 | 9/2007 | Landry et al. |
| 2007/0219854 A1 | 9/2007 | Mueller et al. |
| 2007/0233079 A1 | 10/2007 | Fallin et al. |
| 2007/0233097 A1 | 10/2007 | Anderson et al. |
| 2007/0233158 A1 | 10/2007 | Rodriguez |
| 2007/0239159 A1 | 10/2007 | Altarac et al. |
| 2007/0239259 A1 | 10/2007 | Boylan et al. |
| 2007/0265582 A1 | 11/2007 | Kaplan et al. |
| 2007/0270815 A1 | 11/2007 | Johnson et al. |
| 2007/0282395 A1 | 12/2007 | Maltan et al. |
| 2007/0282396 A1 | 12/2007 | Overstreet et al. |
| 2007/0299443 A1 | 12/2007 | DiPoto et al. |
| 2007/0299444 A1 | 12/2007 | DiPoto et al. |
| 2008/0004676 A1 | 1/2008 | Osypka et al. |
| 2008/0009864 A1 | 1/2008 | Forton et al. |
| 2008/0009920 A1 | 1/2008 | Gibson et al. |
| 2008/0015582 A1 | 1/2008 | DiPoto et al. |
| 2008/0039838 A1 | 2/2008 | Landry et al. |
| 2008/0045957 A1 | 2/2008 | Landry et al. |
| 2008/0071274 A1 | 3/2008 | Ensign |
| 2008/0071323 A1 | 3/2008 | Lowry et al. |
| 2008/0077139 A1 | 3/2008 | Landry et al. |
| 2008/0086130 A1 | 4/2008 | Lake et al. |
| 2008/0097457 A1 | 4/2008 | Warnick |
| 2008/0097519 A1 | 4/2008 | Calderon et al. |
| 2008/0119849 A1 | 5/2008 | Beardsley et al. |
| 2008/0119850 A1 | 5/2008 | Sicvol et al. |
| 2008/0119862 A1 | 5/2008 | Wicker et al. |
| 2008/0125788 A1 | 5/2008 | Cohen et al. |
| 2008/0125817 A1 | 5/2008 | Arnett et al. |
| 2008/0140075 A1 | 6/2008 | Ensign et al. |
| 2008/0140120 A1 | 6/2008 | Hestad et al. |
| 2008/0140132 A1 | 6/2008 | Perez-Cruet |
| 2008/0140154 A1 | 6/2008 | Loeb et al. |
| 2008/0177269 A1 | 7/2008 | Seelig |
| 2008/0183241 A1 | 7/2008 | Bedenbaugh |
| 2008/0208074 A1 | 8/2008 | Snyder et al. |
| 2008/0208302 A1 | 8/2008 | Alexander et al. |
| 2008/0218472 A1 | 9/2008 | Breen et al. |
| 2008/0262318 A1 | 10/2008 | Gorek et al. |
| 2008/0312716 A1 | 12/2008 | Russell |
| 2009/0018599 A1 | 1/2009 | Hastings et al. |
| 2009/0082819 A1 | 3/2009 | Blain et al. |
| 2009/0112278 A1 | 4/2009 | Wingeier et al. |
| 2009/0118804 A1 | 5/2009 | Moffitt et al. |
| 2009/0171392 A1 | 7/2009 | Garcia-Bengochea et al. |
| 2009/0187220 A1 | 7/2009 | Hamada |
| 2009/0216278 A1 | 8/2009 | Song |
| 2009/0221878 A1 | 9/2009 | Gorek |
| 2009/0221879 A1 | 9/2009 | Gorek |
| 2009/0222044 A1 | 9/2009 | Gorek |
| 2009/0222045 A1 | 9/2009 | Gorek |
| 2009/0222046 A1 | 9/2009 | Gorek |
| 2009/0234392 A1 | 9/2009 | Dziedzic et al. |
| 2009/0259137 A1 | 10/2009 | Delic et al. |
| 2009/0287061 A1 | 11/2009 | Feigenbaum et al. |
| 2010/0049206 A1 | 2/2010 | Biyani |
| 2010/0145176 A1 | 6/2010 | Himes |
| 2010/0249844 A1 | 9/2010 | Durrani |
| 2011/0022088 A1 | 1/2011 | Forton et al. |
| 2011/0077692 A1* | 3/2011 | Jackson ............. A61B 17/7037 606/304 |
| 2011/0196426 A1 | 8/2011 | Peukert et al. |
| 2011/0238117 A1 | 9/2011 | Geist et al. |
| 2011/0282390 A1* | 11/2011 | Hua ............... A61B 90/92 606/264 |
| 2011/0301647 A1* | 12/2011 | Hua ............... H04N 5/46 606/279 |
| 2011/0319938 A1 | 12/2011 | Piza Vallespir et al. |
| 2012/0016422 A1* | 1/2012 | Hua ............... A61B 17/7085 606/264 |
| 2012/0065693 A1 | 3/2012 | Lim et al. |
| 2013/0184763 A1 | 7/2013 | McClintock et al. |
| 2014/0039556 A1 | 2/2014 | Rutschmann et al. |
| 2015/0066088 A1 | 3/2015 | Brinkman et al. |
| 2015/0374354 A1* | 12/2015 | Boyd ............... A61B 17/3423 600/204 |
| 2016/0331410 A1* | 11/2016 | Tsuang ............. A61B 17/7037 |
| 2018/0000372 A1 | 1/2018 | Hua |
| 2018/0070987 A1 | 3/2018 | Su et al. |
| 2019/0069930 A1* | 3/2019 | Su .................. A61B 17/7032 |
| 2019/0090918 A1* | 3/2019 | Jackson ............ A61B 17/702 |
| 2019/0216453 A1* | 7/2019 | Predick ............ A61B 17/025 |
| 2019/0231394 A1* | 8/2019 | Bechtel ............ A61B 17/025 |
| 2019/0290332 A1* | 9/2019 | Tsuang ............. A61B 17/7032 |
| 2020/0107865 A1* | 4/2020 | Lu ................. A61B 17/7085 |
| 2021/0000510 A1 | 1/2021 | Hua |

FOREIGN PATENT DOCUMENTS

| | | |
|---|---|---|
| CN | 101022848 A | 8/2007 |
| CN | 201157401 Y | 12/2008 |
| EP | 2 777 573 A1 | 9/2014 |
| EP | 2 892 452 B1 | 8/2018 |
| GB | 2330078 A | 4/1999 |
| JP | H10-080431 A | 3/1998 |
| JP | 2005-516697 A | 6/2005 |
| JP | 2005-324017 A | 11/2005 |
| JP | 2006-504505 A | 2/2006 |
| JP | 2007-520319 A | 7/2006 |
| JP | 2006-518655 A | 8/2006 |
| JP | 2007-502662 A | 2/2007 |
| JP | 2007-524463 A | 8/2007 |
| JP | 2008-509759 A | 4/2008 |

(56) References Cited

FOREIGN PATENT DOCUMENTS

| | | | |
|---|---|---|---|
| JP | 2008-539029 A | 11/2008 |
| RU | 2285483 C2 | 10/2006 |
| SU | 1771717 A1 | 10/1992 |
| WO | WO 2003/066153 A2 | 8/2003 |
| WO | WO 2004/041100 A1 | 5/2004 |
| WO | WO 2004/075768 A2 | 9/2004 |
| WO | WO 2006/019723 A2 | 2/2006 |
| WO | WO 2008/039247 A2 | 4/2008 |
| WO | WO 2008/136802 A1 | 11/2008 |
| WO | WO 2010/039817 A2 | 4/2010 |
| WO | WO 2010/039817 A3 | 7/2010 |
| WO | WO 2010/085782 A2 | 7/2010 |
| WO | WO 2010/039817 A4 | 9/2010 |
| WO | WO 2011/040986 A1 | 4/2011 |
| WO | WO 2011/084788 A2 | 7/2011 |
| WO | WO 2011/123580 A1 | 10/2011 |
| WO | WO 2021/092495 A1 | 5/2021 |

OTHER PUBLICATIONS

"MANTIS® Spinal System Surgical Technique", Stryker Spine, MIMAN-ST-2_Rev-3, 2015, (Brochure) in 48 pages.

2009 K2M Complex Spine Innovations, "Serengeti Minimally Invasive Retractor System, A Simple Approach to Complex Spine", 2 pages 2009.

2010 K2M Complex Spine Innovations, Mesa Spinal System Lumbar Products for Surgeons Treating Spinal Disorders, 1 page. Downloaded May 6, 2010.

Buchholz, A. et al., "Deformity Correction Through the Use of Reduction Towers: 2-Dimensional Operative Video", Operative Neurosurgery, Aug. 2020, vol. 19, Issue 2, pp. E157-E158.

Buell. T. et al., "Surgical correction of severe adult lumbar scoliosis (major curves > 75°): retrospective analysis with minimum 2-year follow-up", Journal of Neurosurgery Spine, Jun. 2019, vol. 21, pp. 1-14.

Carbunaru, R. et al., "Rechargeable Battery-Powered bion® Microstimulators for Neuromodulation," Proceedings of the 26th Annual International Conference of the IEEE EMBS San Francisco, CA, USA, Sep. 1-5, 2004. 0-7803-B439-3/04/$20.00©2004 IEEE, in 4 pages.

Demura, S. et al., "Influence of Rod Contouring on Rod Strength and Stiffness in Spine Surgery", Orthopedics, Jun. 2015, vol. 38(6), pp. e520-e523.

Ezzyat, Y. et al., "Closed-loop stimulation of temporal cortex rescues functional networks and improves memory", Nature Communications, vol. 9, Feb. 2018, in 8 pages. URL: https://www.nature.com/articles/s41467-017-02753-0.

Giles, Jim, "Electric currents boosts brain power" in Nature, Oct. 26, 2004, in 2 pages.

Kokabu, T. et al., "Identification of optimized rod shapes to guide anatomical spinal reconstruction for adolescent thoracic idiopathic scoliosis", Journal of Orthopaedic Research, Jul. 2018, pp. 3219-3224.

Loeb, G. et al., "The BION Devices: Injectable Interfaces with Peripheral Nerves and Muscles." Neurosurg Focus. 2006;20(5) ©2006 American Association of Neurological Surgeons Posted Aug. 15, 2006, in 12 pages.

Medtronic Sofamor Danek METRx System Surgical Technique "Minimal Access Spinal Technologies" article, 2004, 22 pages.

Mims, C., "A Hardware Update for the Human Brain", The Wall Street Journal, Jun. 5, 2017, in 4 pages. URL: https://www.wsj.com/articles/a-hardware-update-for-the-human-brain-1496660400.

Santoni, B.G. et al., "Cortical Bone Trajectory for Lumbar Pedicle Screws", The Spine Journal, vol. 9, pp. 366-373.

Simonite, Tim. "Brain blanket boosts mind control" in New Scientist. Feb. 15, 2008, posted online, in 3 pages.

Singer, Emily, "Want to Enhance Your Brain Power? Research hints that electrically stimulating the brain can speed learning," MIT Technology Review, Jun. 26, 2008, in 2 pages.

International Search Report and Written Opinion dated Mar. 12, 2021, from PCT Application No. PCT/US2020/059547.

International Search Report and the Written Opinion dated May 25, 2010, from PCT Application No. PCT/US2009/059004.

International Preliminary Report on Patentability dated Apr. 14, 2011, from PCT Application No. PCT/US2009/059004.

International Search Report and Written Opinion dated Oct. 18, 2010, from PCT Application No. PCT/US2010/029199.

International Preliminary Report on Patentability dated Apr. 3, 2012, from PCT Application No. PCT/US2010/029199.

International Preliminary Report on Patentability dated Jul. 5, 2012, from PCT Application No. PCT/US2010/061531.

International Search Report and Written Opinion dated Sep. 8, 2011, from PCT Application No. PCT/US2010/061531.

International Search Report and Written Opinion dated Jun. 6, 2011, from PCT Application No. PCT/US2011/030612.

International Preliminary Report on Patentability dated Oct. 2, 2012, from PCT Application No. PCT/US2011/030612.

* cited by examiner

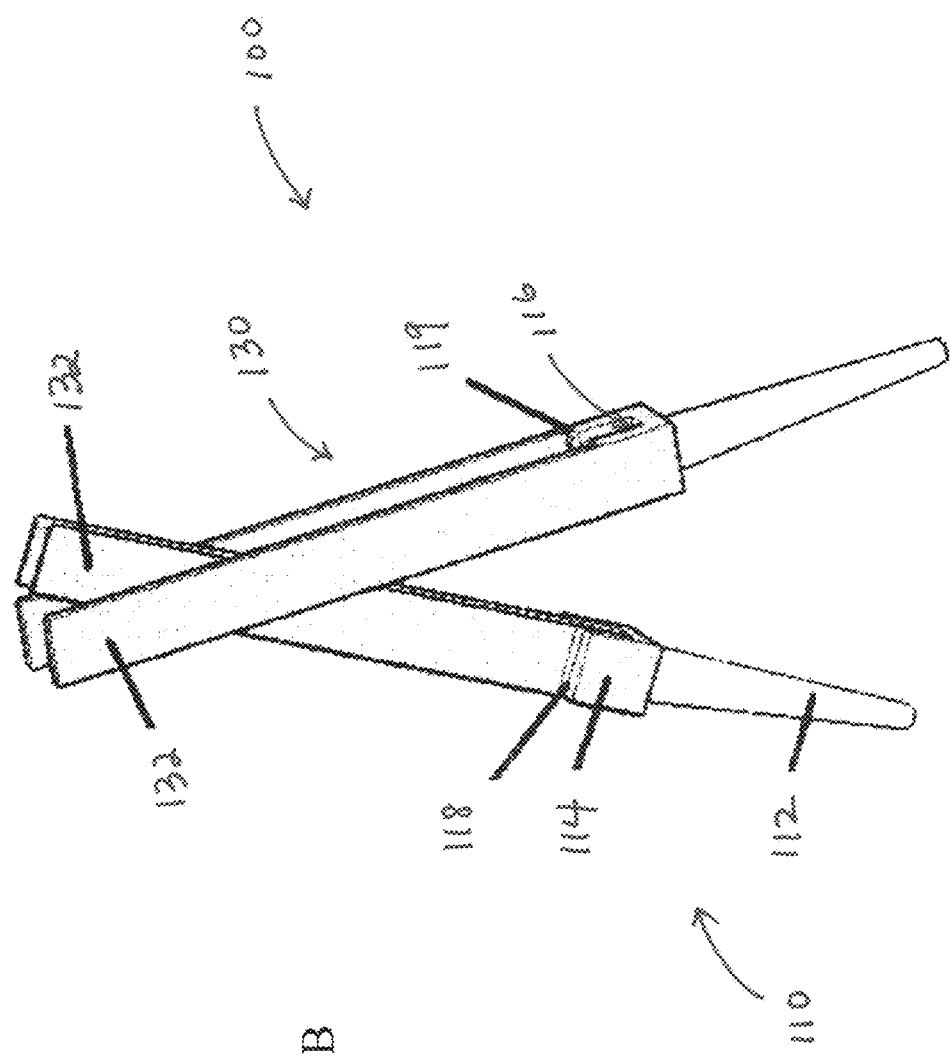

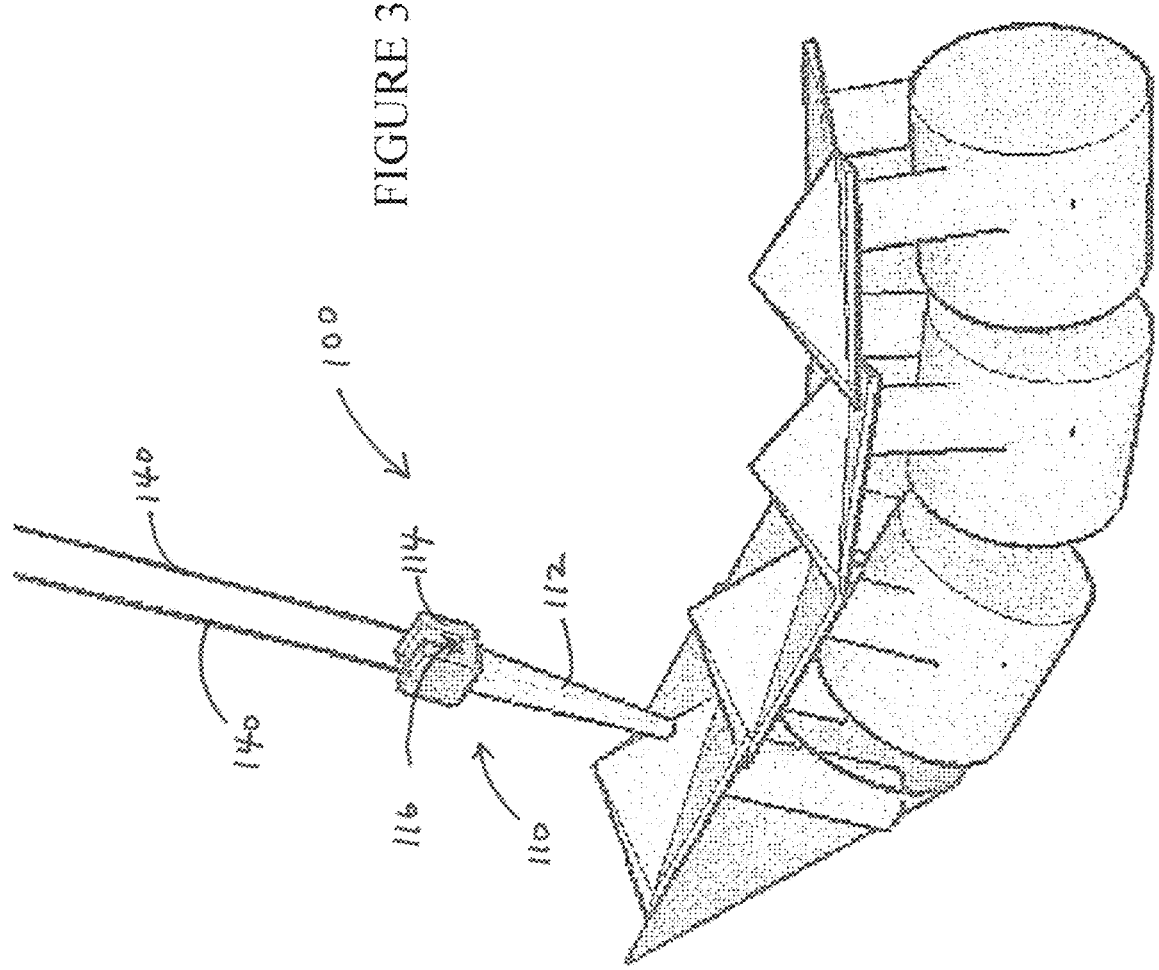

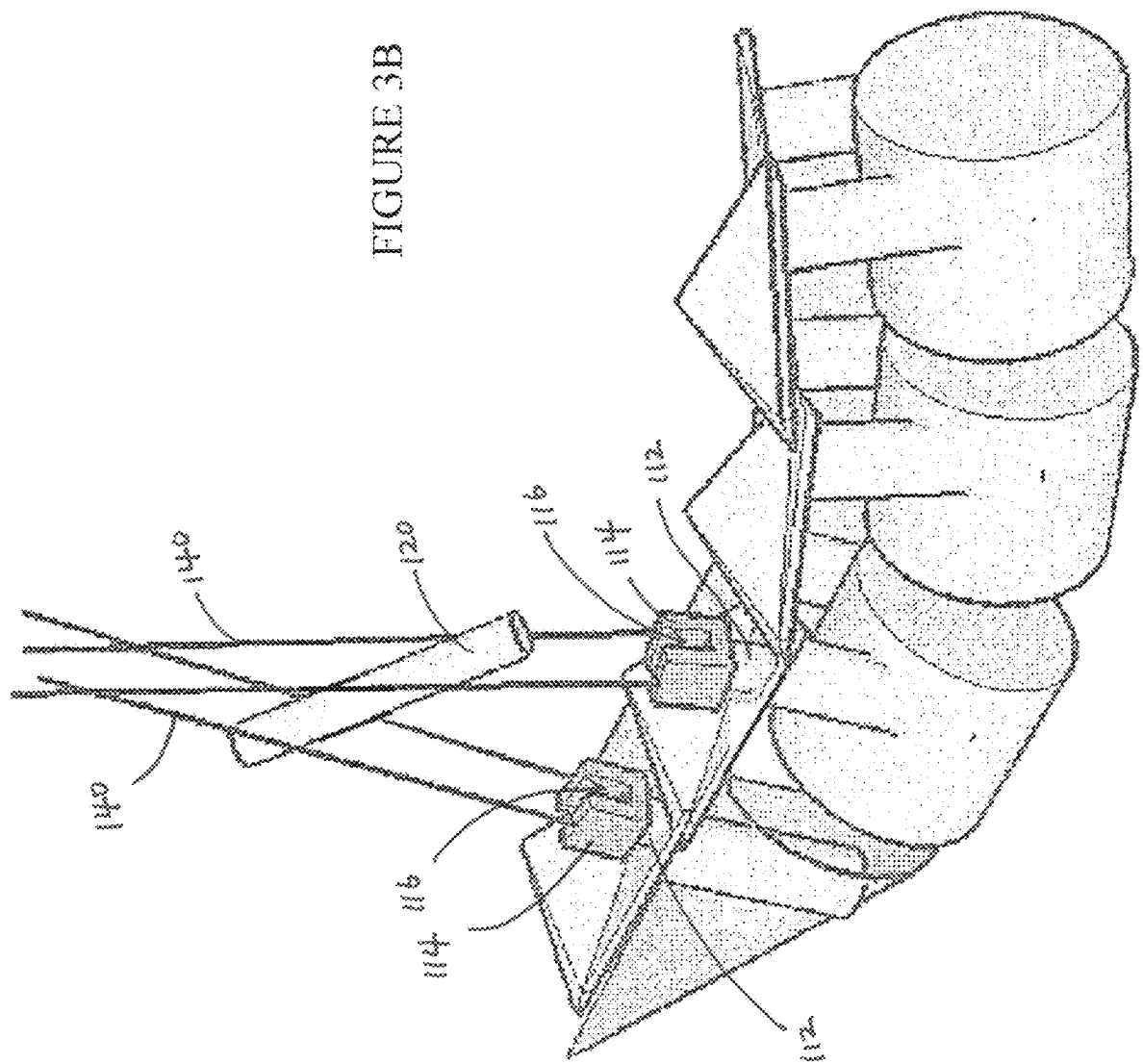

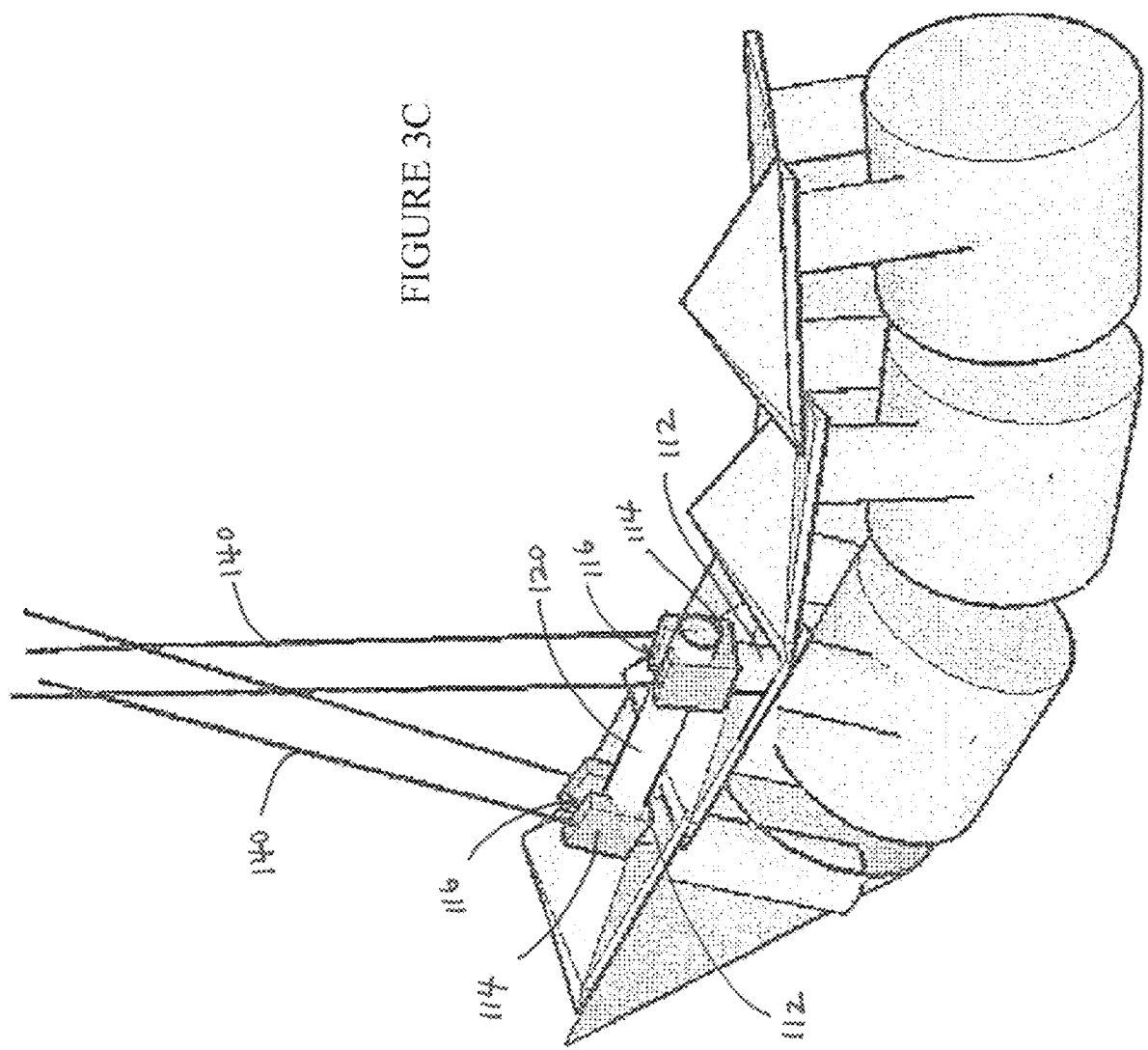

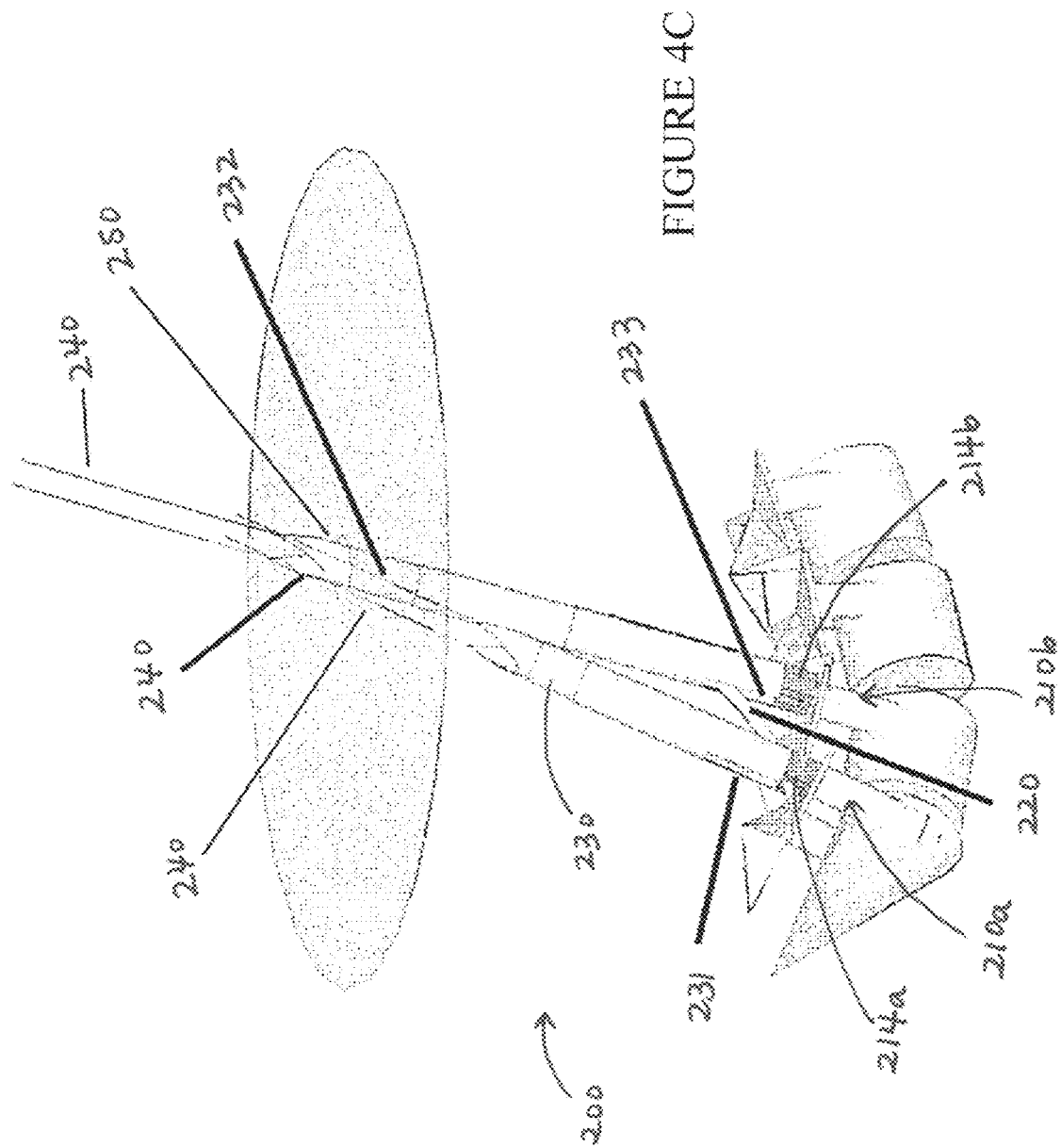

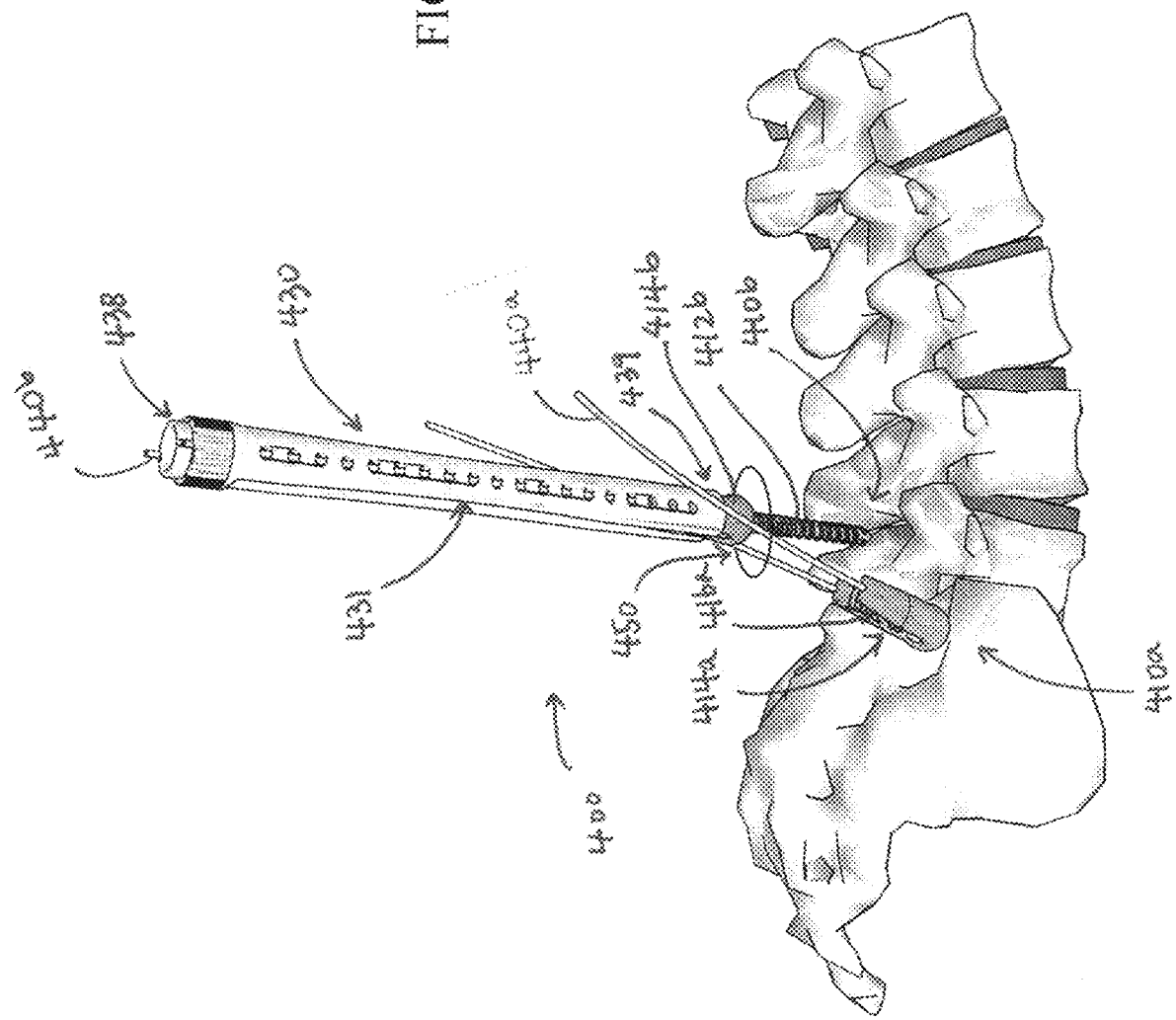

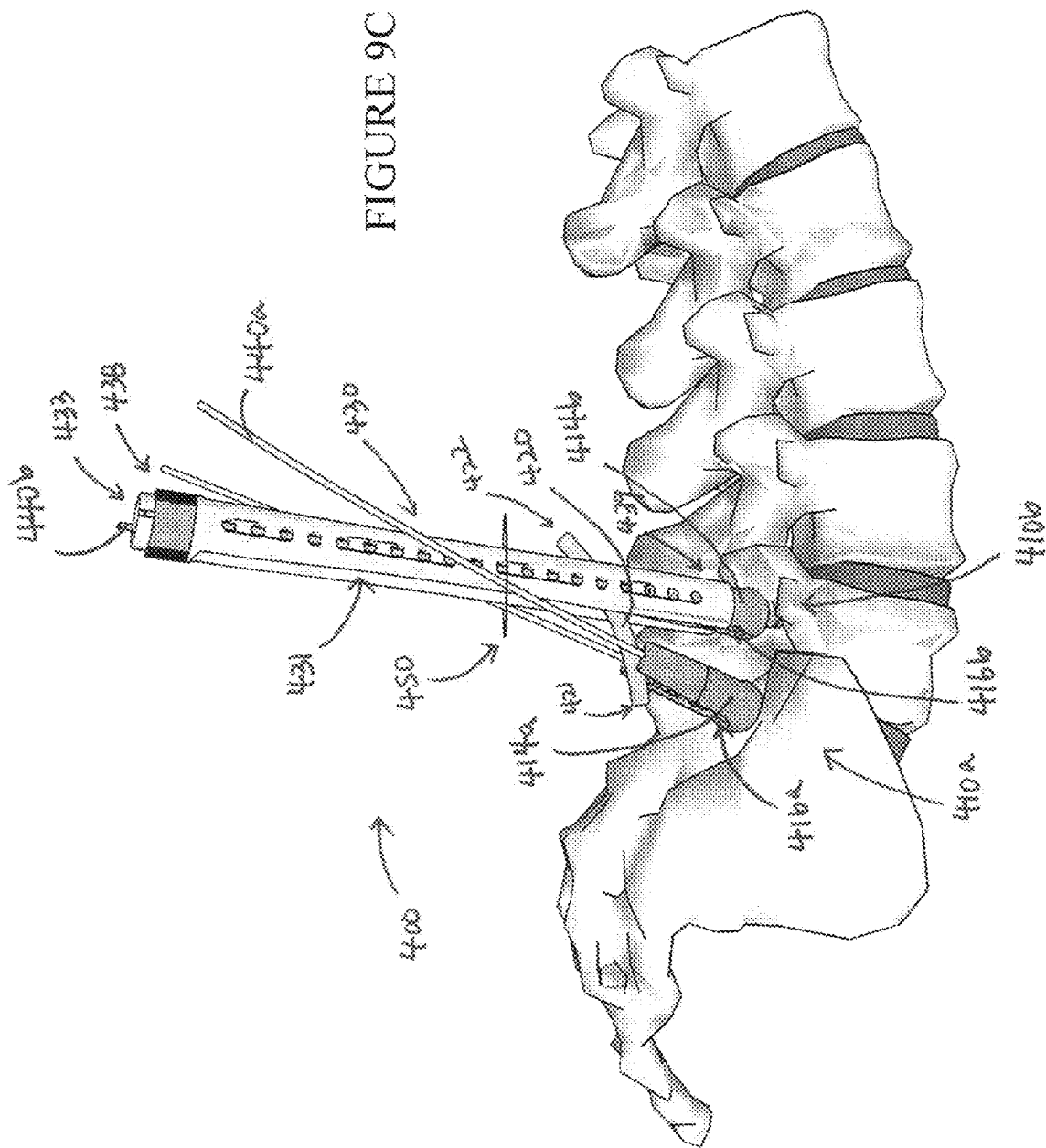

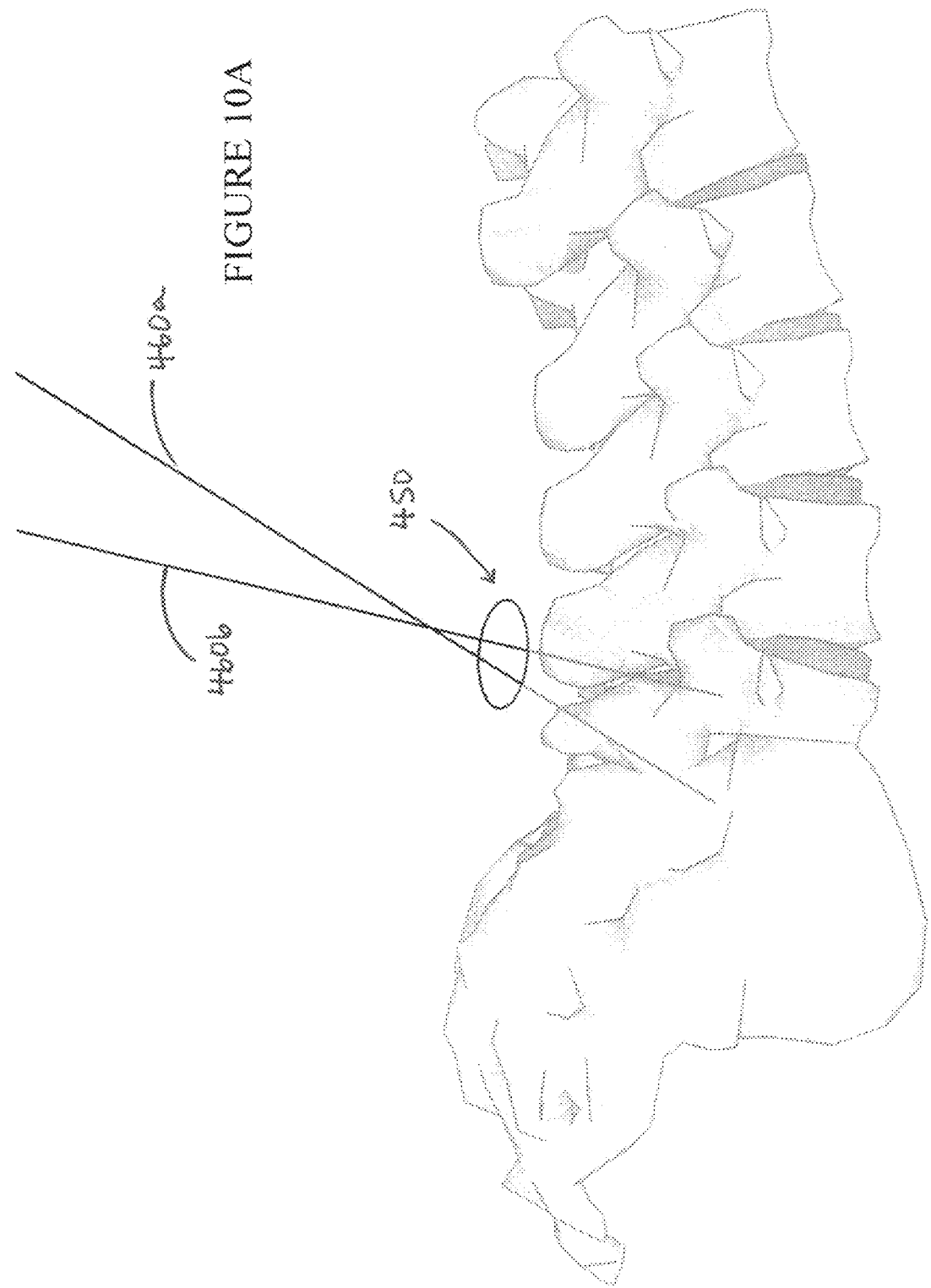

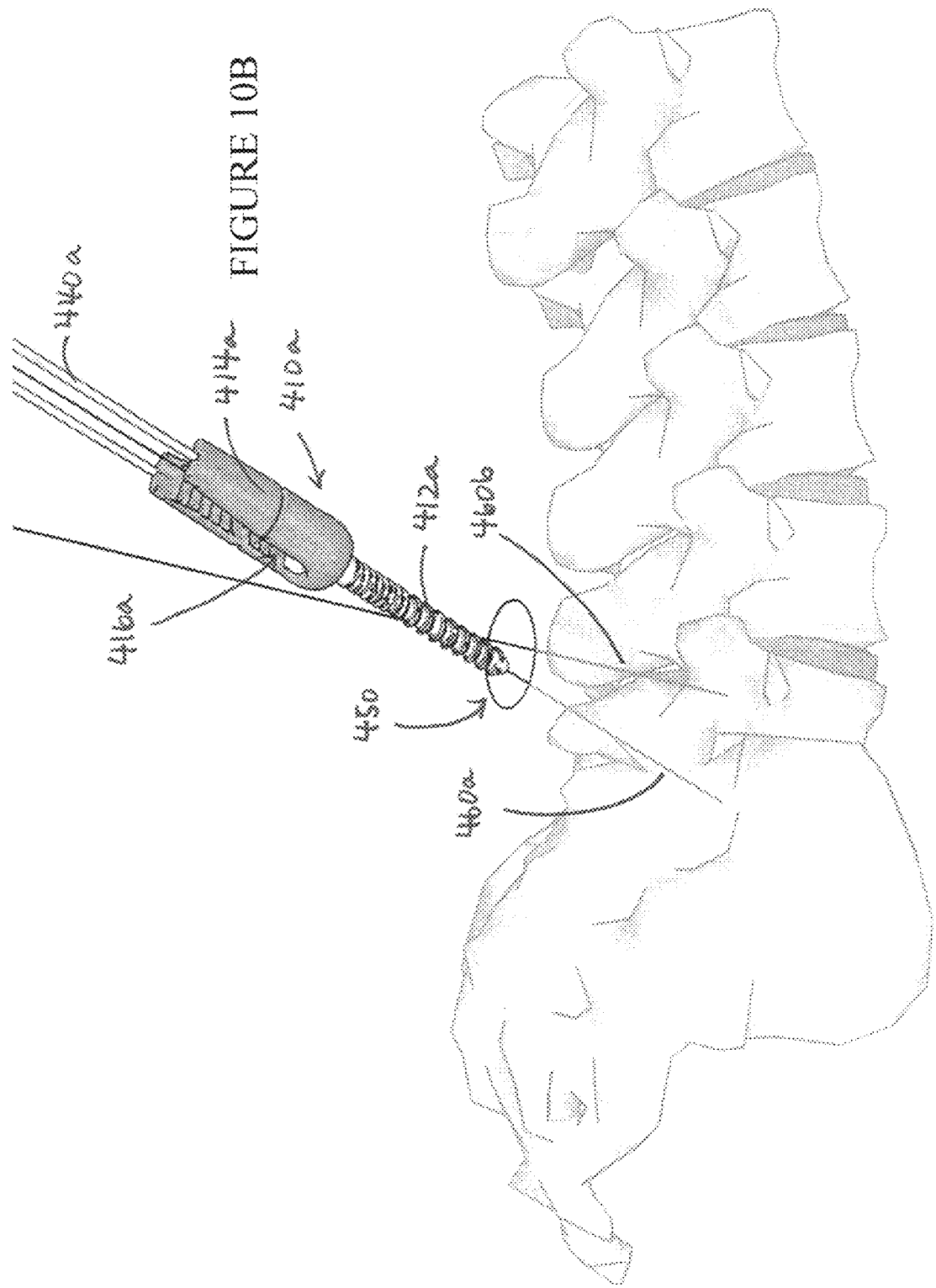

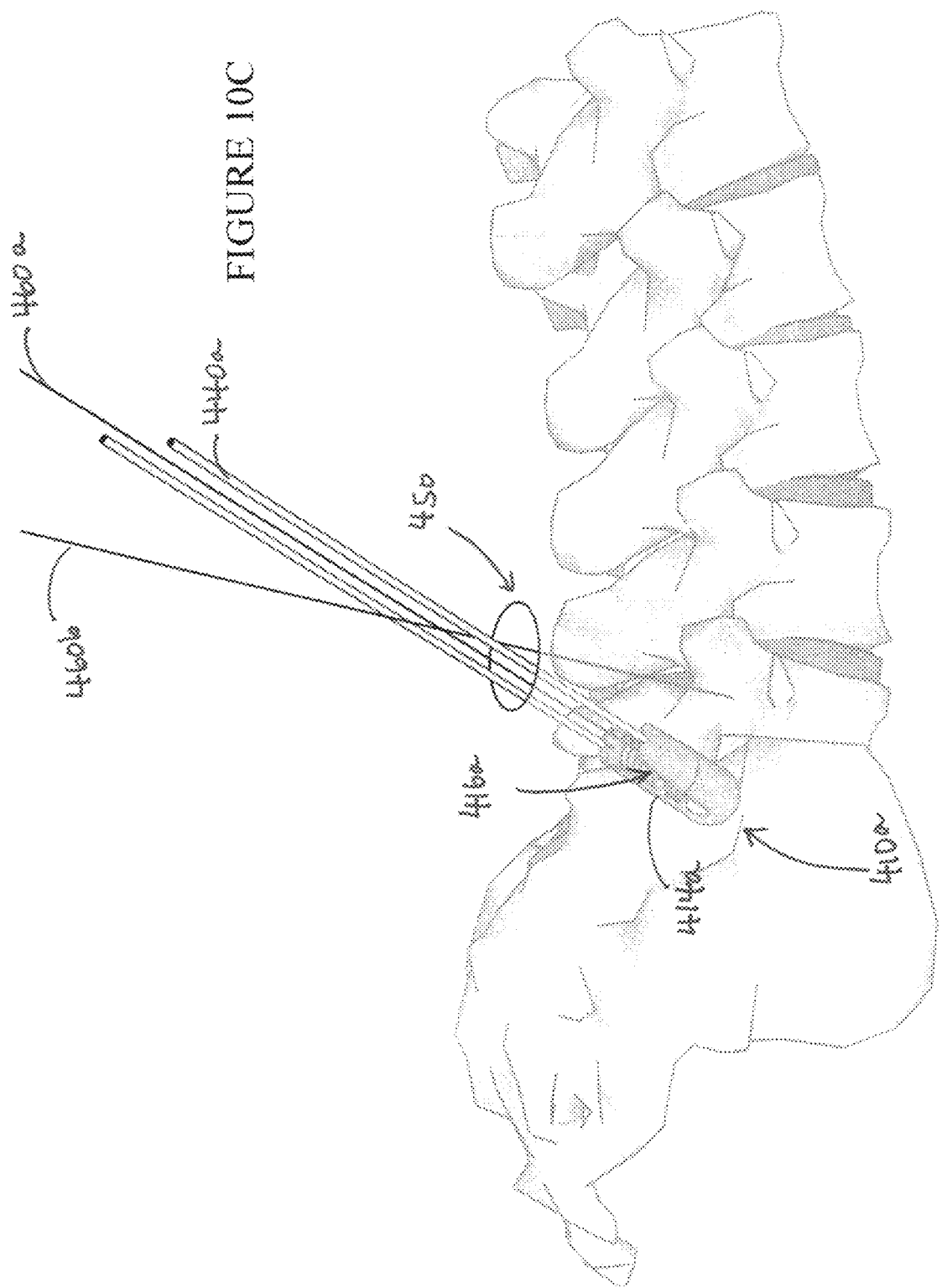

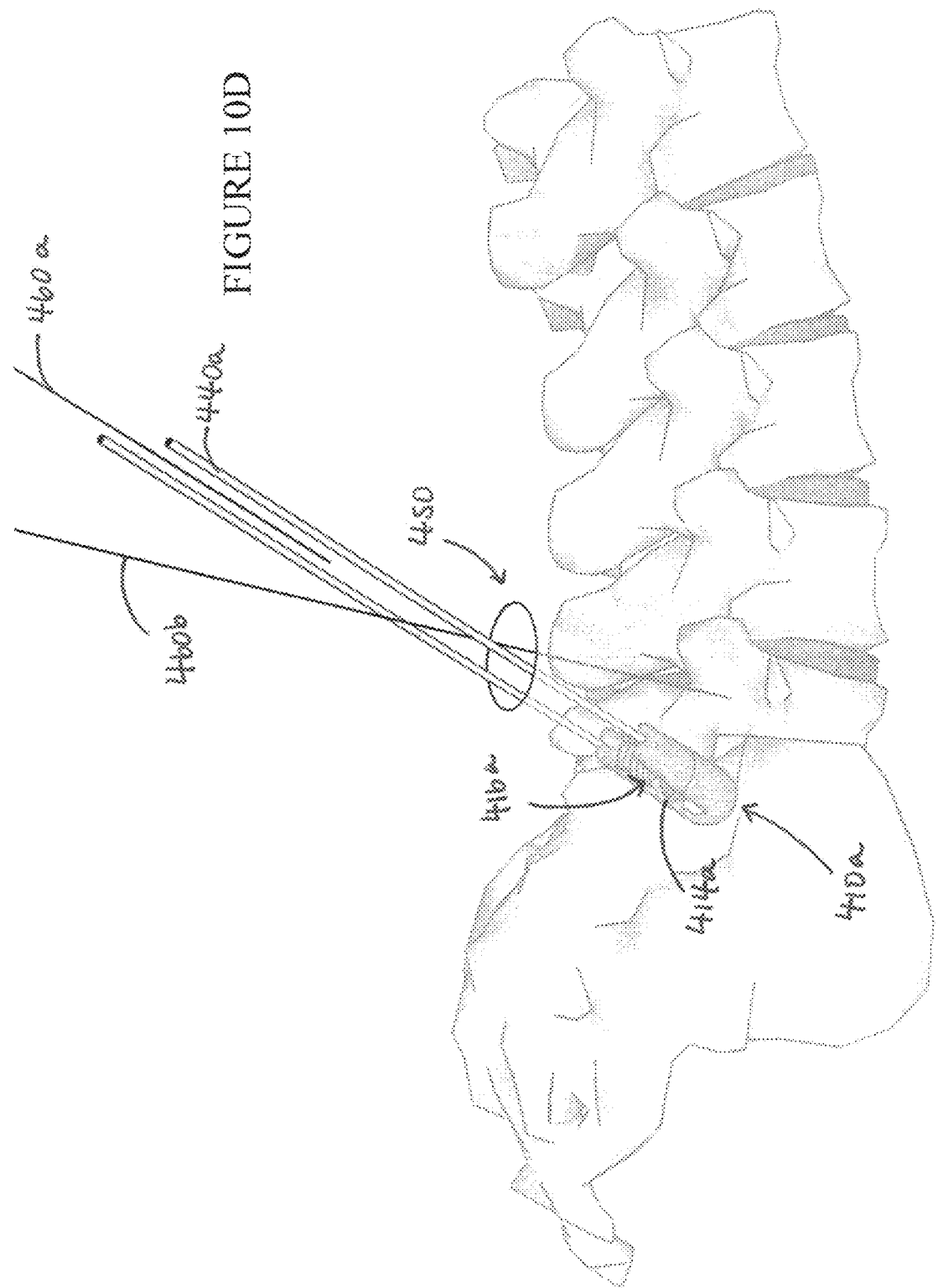

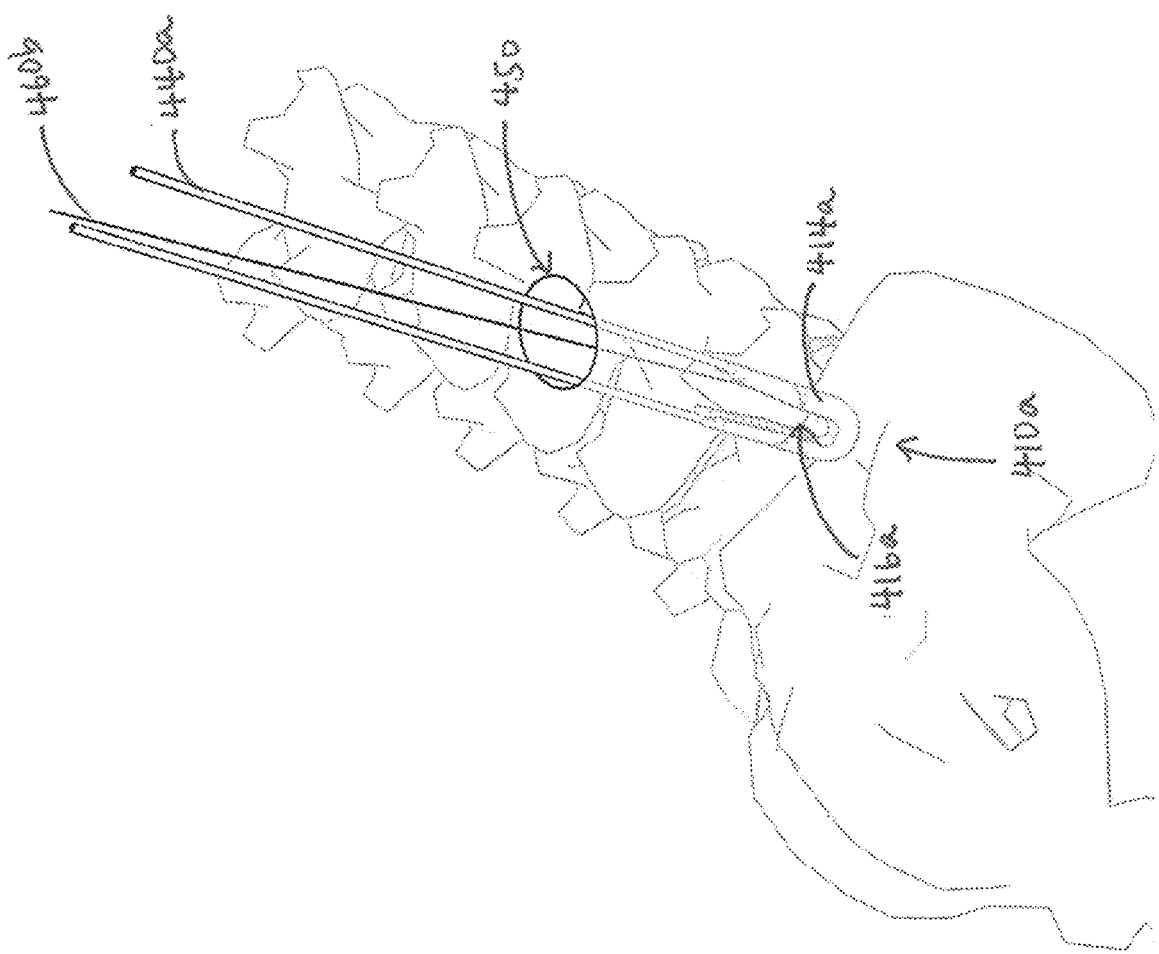

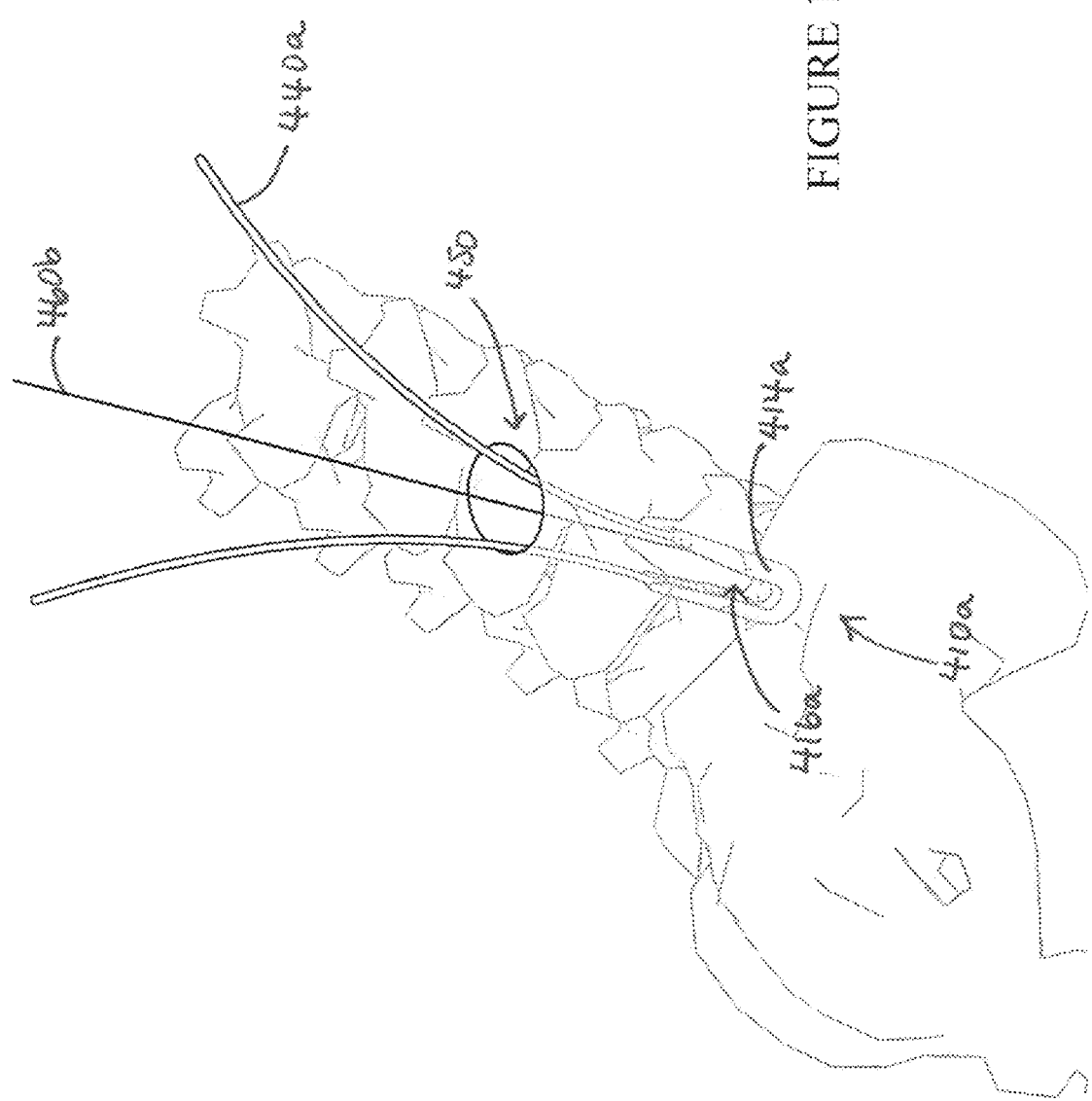

SYSTEMS AND METHODS FOR PEDICLE SCREW STABILIZATION OF SPINAL VERTEBRAE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present invention relates to medical devices, systems and methods for bone fixation. Specifically, embodiments of the invention are related to stabilizing adjoining vertebrae in the cervical, thoracic, and lumbosacral spine. In addition, embodiments of the invention are related to fusion or stabilization of vertebrae in the lumbar spine to alleviate axial back pain and radicular pain. Embodiments of the invention are also related to improving minimally invasive surgical (MIS) approaches to pedicle screw fusion by reducing the number and size of incisions and the size of the medical instruments inserted therein. Further embodiments of the invention specifically relate to improving the efficiency of percutaneous lumbar pedicle screw fusion for the surgeon while minimizing the surgical trauma to the patient's tissue.

Description of the Related Art

While some lower back conditions can be ameliorated with non-surgical approaches, spinal fusion is recommended for certain conditions when non-surgical approaches fail. Non-surgical approaches include medications, physical therapy, chiropractic treatment, traction, epidural steroid injections, facet blocks or rhizotomy, weight loss, smoking cession, and acupuncture. Conditions that commonly serve as indications for spinal fusion or stabilization surgery can be divided generally into three categories: (i) trauma induced, (ii) curvature, and (iii) degenerative.

Trauma induced conditions include fractures and ligamentous injuries. Fractures typically result from an unfortunate incident involving an extraneous force or fall but may also arise from pathologic conditions, such as cancer or osteoporosis. Fractures are often compressive in nature and typically lead to a pathological curving of the spine resulting in a loss of the natural lordotic curvature in the lumbar and cervical spine, known as kyphosis. Fractures of the spine also occur with translational or rotational forces perpendicular to the axis of the spine. These forces result in fractures of the facet or pars interarticularis (pars). If the external forces are large enough, vertebrae can collapse resulting in a burst fracture that can injure all three (3) columns of the vertebrae (anterior, middle, and posterior columns). Many traumatic injuries can heal without surgery, but unstable injuries that pose a risk for neurologic injury and/or pain require stabilization through a procedure such as fusion.

A condition called spondylolisthesis characterized by slippage of the spine bones or vertebrae relative to one another can result from fractures of the pars interarticularis (pars fracture) known as spondylolysis. Spondylolisthesis can also develop from malformation of the facet joints by degenerative arthritis as well as congenital malformation and pathologic conditions such as tumors. If the pars on both sides are fractured, then the spinous process and lamina are essentially completely disconnected from the pedicle and vertebral body. This large fragment is called the Gill body. Pars fractures are actually common in people of all ages (often acquired in the teenage years). While, many of these patients are mildly symptomatic and do not require surgery, those with progressive symptoms may require surgical decompression with or without fusion. Spondylolisthesis results in misalignment of the spine and increases the risk of a nerve becoming entrapped. Nerves travel within the spinal canal bounded by the vertebrae and their roots protrude from the curved openings in the sides of the vertebrae called foramina (singular is foramen). These spinal nerves are suspected to be the source of back and radicular pain when they become entrapped or when the nerve endings become irritated by irregular or abrasive motion around a disc, bone, or joint. Spondylolisthesis can also aggravate or be accompanied by degeneration of disc or facet joint which can lead to axial back pain.

The normal curvature of the lumbar and cervical spine is lordosis, where the posterior aspect of these spinal levels forms a concave curve. The thoracic spine normally has a kyphotic or convex curve. Curvature conditions include straightening of the natural curvature as well as abnormal lordosis, abnormal kyphosis or lateral/rotational bending called scoliosis. Curvature conditions can occur idiopathically during adolescence, e.g., adolescent idiopathic scoliosis, or develop as a secondary problem in situations where spinal muscle activation is abnormal such as cerebral palsy, spina bifida, or tethered cord syndrome. Abnormal spinal curvature is common in spinal degeneration when the discs and joints degenerate asymmetrically leading to a progressive curvature (scoliosis, kyphosis, or lordosis) as the biomechanics of the spine are disrupted. Curvature conditions also occur after trauma with compression or burst fractures or with ligamentous injury. Additionally, curvature conditions can occur iatrogenically after previous spinal surgery where the anatomy and biomechanics of the spine have been altered. Such situations include the removal of the posterior tension band after laminectomy as well as the alteration of physiologic movement after spinal fusion leading to adjacent level compensation and degeneration. Curvature conditions lead to abnormal biomechanical stress on the discs and facet joints accompanied by compensatory measures such as facet or ligamentous hypertrophy. Patients can develop both axial back pain and radicular pain. In patients who have failed conservative therapy and bracing, surgery can be effective. Surgery in these conditions includes decompression of nerve or spinal cord compression as well as fusion or stabilization. Curvature can be corrected through surgery, and fusion prevents further curvature from developing.

Degenerative conditions include spinal arthritis and recurrent disc herniation. Spinal arthritis is the most common indication for fusion and may exist in the form of severe disc degeneration (also called Degenerative Disc Disease, DDD) or facet disease. Degenerative arthritis can also be a cause of spondylolisthesis in addition to traumatic fractures discussed above. Degenerative conditions are generally accompanied by nerve compression causing radicular pain in the distribution of the nerve's receptive field, which usually correlates with and is manifested in arm or leg pain. Pure nerve compression syndromes such as herniated nucleus pulposus (herniated discs) or foraminal stenosis (narrowing of the side foramina canals through which the nerves pass) can often be treated with decompression without fusion.

Pure disc degeneration syndromes can be treated with fusion without decompression of the nerves. However, most commonly disc degeneration occurs in combination with nerve compression causing both axial back pain and radicular limb pain. In these circumstances, fusion surgery is combined with nerve decompression surgery.

Fusion functions to eliminate motion in the disc space and facet joints between adjacent vertebrae. The vertebrae provide the rigid structural framework of the spine and the fibrocartilaginous disc space acts as a cushion or shock-absorber. Degradation of the disc space can distort alignment and alter the biomechanical cushion that the disc affords the adjacent vertebrae. This degradation alters the forces impacted upon the vertebrae and results in axial back pain. Fusion is designed to eliminate movement between adjacent vertebrae by either forming a solid bridge of bone across the disk space and/or creating new bone formation in the posterolateral space to provide stabilization, rigidity, and strength. Sometimes fusion involves a bone graft taken from another location in the body (e.g., autograft from the iliac crest in the pelvis) or from an external source, e.g., allograft. Physicians commonly refer to the level of a fusion. A single level fusion involves stabilizing the two vertebral bones adjacent to a diseased disc. A two-level fusion involves stabilizing three adjacent vertebral bones spanning two problematic disc spaces. Each vertebra makes contacts (joints) with adjacent vertebrae at three points, the paired facet joints located posteriorly and the intervertebral disc located anteriorly. Thus, lumbar fusion can be directed either at the posterior facet joints or at the anterior interbody/disc space or both. When an anterior interbody fusion is performed in combination with posterior fusion, the procedure is termed 360° fusion. One commonly used technique of posterolateral fusion is pedicle screw fusion where screws are directed into the pedicle portions and the bodies of adjacent vertebrae and then rods are connected to the screws across the disc spaces. The screws and rods hold the adjacent vertebrae motionless relative to one another and allow the bone graft that is placed either in the interbody (disc) space or in the posterolateral space to grow into solid bone. Conventional pedicle screws and rods are metal, typically titanium (Ti) alloy but have been made from stainless steel as well. Recently rods have been made from a minimally flexible polymer called polyetheretherketone (PEEK). Other metals have been used and can also be adopted. These can include, for example, cobalt, molybdium, and other metallic as well as nonmetal polymers.

A newer lumbar pedicle screw technique involves placing screws from a midline incision and placing screws superiorly and laterally instead of the typical trajectory of starting laterally and aiming medically through the pedicle into the vertebral body. This technique has been named Cortical Bone Trajectory (CBT) because the trajectory of the screw transverses more cortical bone in contrast to cancellous bone. Cortical bone is typically harder and thus provides greater pullout strength. Thus cortical bone trajectory allows smaller and shorter screws with a single midline incision instead of bilateral Wiltse style incisions. The issue with CBT screw trajectory is that the superior screw in a lumbar fusion such as L4 trajectory in a L4, L5 TLIF surgery, has a trajectory that is aimed more superiorly and laterally rather than a medical trajectory. The inferior screw can have a parallel trajectory or have a more straight-in trajectory in the sagittal plane (rather than superior direction). This configuration causes a natural crossing of the superior screw with the inferior screw in that the superior screw is aimed superiorly so a MIS screw attached to a tower has the tower directed inferiorly because the screw is directed superiorly. While the inferior screw is directed is a less superior trajectory so the towers attached to these two screws are bound to interfere. Furthermore since the incision is midline and the screws are directed from medial to lateral direction, then the screws from ipsilateral and contralateral sides also are bound to intersect. Thus cortical bone trajectory is a technique that would benefit from towers attached to screws that did not interfere with each other due to the fact that they have interfering trajectories.

Interbody fusion involves placing one or more spacers (typically pre-loaded with bone graft material) within the interbody (disc) space between bony vertebral bodies after the degenerated disc has been cleaned out and removed. Spacers are made from bone grafts, titanium, carbon fiber, or polymers such as PEEK. Interbody fusion can be performed through several approaches including: an anterior approach (anterior lumbar interbody fusion, ALIF), a posterior approach (posterior lumber interbody fusion, PLIF, or transforaminal lumbar interbody fusion, TLIF), or a lateral approach (direct lateral interbody fusion, DLIF™-Medtronic, or extreme lateral interbody fusion, XLIF™-Nuvasive). The aim of these approaches is to remove the degenerated disc and replace the disc with material that induces bony fusion. Alternatively, the disc can be replaced with an artificial joint/disc (discussed below). Each of these interbody approaches has advantages and disadvantages. Anterior procedures require a retroperitoneal dissection and risk injury to the large blood vessels anterior to the lumbar vertebrae. In addition, injury to the nerve plexus anterior to the vertebrae can result in sexual dysfunction. The lateral approach is promising but is limited to the upper and mid lumbar levels (rostral to L5, S1) because of obstruction by the iliac crest. The posterior interbody approach is more time consuming and typically requires more muscle dissection and retraction. However, the posterior approach allows the placement of the interbody graft, posterior pedicle screw fusion, and decompression of nerves all to occur through the posterior incision(s).

Although anterior and lateral approaches can be performed stand-alone (without posterior instrumentation), many surgeons will back-up or supplement anterior or lateral interbody fusions by placing pedicle screws posteriorly after the interbody cage or graft has been placed. This 360° fusion limits movement more than just an isolated anterior or posterior fusion, and fusion rates are increased. However, in ALT and lateral interbody (DLIF™, XLIF™) cases, two sets of incisions are required for a 360° fusion.

The posterior approaches (TLIF and PLIF) allow an interbody fusion, pedicle screw fusion, and neural decompression to be done all through the same posterior incision(s). In the TLIF, a single large interbody spacer is inserted on the side ipsilateral to the patient's symptomatic side after neural decompression is completed. If both sides are symptomatic then decompression is required on both sides. A PLIF is performed by placing two interbody spacers, one on each side. Posterior procedures may be done according to: (i) an invasive open procedure in which a large incision and/or several incisions are made, (ii) a percutaneous approach in which small incisions and/or few incisions are made, and potentially (iii) an endoscopic approach in which small incisions are made and all tools and devices are inserted through portals with visualization provided on an external monitor.

As an alternative to fusion, recent advances in interbody stabilization have resulted in the development of artificial disc technology. Artificial discs replace the degenerated discs and allow continued motion at the joint. Both cervical and lumbar artificial discs have been developed. Additionally, dynamic stabilization techniques have been developed for the posterior spine. These posterior techniques utilize pedicle screws and a dynamic rod. Typically the dynamic rod has a mechanism to bend under certain loads or forces, thereby absorbing some stress and strain that is applied to the spine. The advantage of dynamic stabilization is that motion is preserved in the spine. However, the durability of these systems may be an issue. In fusions, the bone graft (interbody or posterolateral) eventually fuses the vertebrae eliminating the need for the spinal instrumentation (screws and rods). However in dynamic stabilization, fusion does not occur, so the screws and dynamic rods will always be subjected to the strain and forces of the spine. Over time, the possibility of loosening of the pedicle screws or mechanical failure may increase. Sometimes the use of a slightly flexible rod such as a rod made of PEEK may actually increase fusion by reducing stress shielding. Stress shielding occurs when rigid fusion constructs shield the vertebral bone in contact with the bone graft from the stresses required to form and remodel bone.

Posterior lumber stabilization (fusion and dynamic stabilization) techniques have evolved into minimally invasive approaches because such minimized exposures reduce patient morbidity and facilitate patients' recovery to function. Blood loss and hospital stays are shorter. The process of performing a minimally invasive pedicle screw fusion is the same as that for dynamic stabilization and involves two basic parts. First, screws are placed percutaneously through the pedicle into the vertebral body. For minimally invasive systems, cannulated screws are placed percutaneously over a fluoroscopically (an X-ray that can be seen on a video screen) guided guidance element. Generally, two screws are used on each vertebral body being fused, one on a right side and the other on a left side. The second part of the process involves connecting the screws with a rod and locking the rod and screws together. In dynamic stabilization, the rod or rod-like device (flexible connector) is bendable, but the process of inserting this bendable rod is the same as that for fusion. For example, a rod-like device (flexible connector), like a rod, fits within the screw heads, but may also include an element (a shock absorber, a spring, etc.) that allows some motion. The variations between different minimally invasive systems mostly arise in the method of placing the rod and locking the rod with the screws through a minimal incision.

Before the intervertebral body spacer is inserted, the damaged or degenerated disc within the disc space must be removed. In the TLIF approach, the disc space is accessed through a facetectomy in which the foramen around the nerve roots is opened with a bone-cutting tool such as an osteotome or a high-speed drill. In the PLIF approach, laminectomies or laminotomies are performed to access the disc space. Both TLIF and PLIF allow for decompression of the spinal thecal sac and the nerve roots; however, the facetectomy in a TLIF allows the maximum decompression of the exiting nerve root on that side. With gentle retraction of the thecal sac, the disc space is easily accessed. Then the instruments used for clearing out the degenerated disc may be inserted into the disc space to complete the discectomy.

Following removal of the disc, the surgeon should prepare the bony surfaces, known as the end plates, of the vertebral bodies on each side of the disc that was removed. Peeling off the end plate with a tool such as a curette induces bleeding which stimulates healing and assimilation of the bone graft to be inserted into the interbody space. The spacer or cage that is to be inserted is typically constructed of bone, titanium, carbon fiber, or polymers such as PEEK. The spacer is usually hollow or at least porous to accommodate bone graft material therein. Bone inducing protein such as bone morphogenetic protein (BMP) is also commonly placed within the spacer. After placing the spacer and bone graft, the rods may be inserted into the pedicle screws and the screws can be tightened to lock the rods in place.

Pedicle screw fusions such as the TLIF can be done open through a single large incision or through a minimally invasive (MIS) approach in which the incision size(s) are smaller, and less tissue is damaged or injured. MIS TLIF typically uses percutaneous pedicle screws where each screw is placed through a small incision just about the side of the diameter of a single screw, screw head, or the largest screw insertion tool. Typically, the placement of the percutaneous screws is straightforward. This is because screws are long and thin and are screwed through the tissue into the bone over a guidewire that is placed through either fluoroscopic guidance or using stereotactic navigation. Whereas in the open approach the screws are placed using visually identified anatomic landmarks and fluoroscopic guidance. Because percutaneous pedicle screws are placed through small incisions that are barely large enough to fit the screw or screw insertion tools, virtually no visual landmarks are available. There are miniopen approaches where visual landmarks for placing pedicle screws can be identified through tiny incisions using either a microscope or endoscope through either a small tubular retractor or endoscope. The key is that once the pedicle screw tract is located and the guidewire is placed into the pedicle screw tract, then placing a percutaneous pedicle screw over the guidewire is relatively easy.

In most of the minimally invasive surgery (MIS) systems used today, a guidance element, such as a wire or guidewire, is placed percutaneously under fluoroscopic guidance through the pedicle. Percutaneous cannulated drills and screw taps are inserted over the guidance element/wire to prepare the tract through the pedicle and vertebral body for pedicle screw insertion. Dilating tubes and a guidance tube or a retractor system can often be used to dilate and hold open the path around the guidance element through skin and muscle to reduce injury to muscle and tissue when pedicle screws and insertion tools are inserted. Pedicle screws are inserted over the guidance elements either with or without passage through a guidance tube/retractor. Because of the development and wide spread use of intraoperative navigation to guide pedicle screw placement, some pedicle screws can be placed without the use of predrilling a hole and use of a guidewire. These systems use intraoperative navigation to directly place the pedicle screw through the tissue into bone without predrilling a hole or tapping the hole. Additionally robotic arms can now be used to also aid in the accurate placement of pedicle screws in addition and often combination with navigation systems.

In MIS pedicle screw fusion, after the pedicle screw has been inserted, there are still critical steps in connecting the screw heads and locking adjacent screws using a rod and locking cap. The insertion of rods that connect the screw heads and locking caps to lock the rod inside the screw heads are currently some of the most difficult steps while using a MIS approach through a minimal incision. In order to place the rod and locking assembly into the screw heads, each screw head is associated with blades or towers that extend upwards from the screwhead through the skin incision. The tower has to accommodate the rod and locking assemblies so it is typically the same size or larger than the maximum diameter of the screw head. Once the towers are in place, the rod is then inserted through one of a variety of methods. The leading MIS system is Sextant™ by Medtronic. In this system, the rod is placed by forming a pendulum like mechanism. The two or three towers (for one or two-level fusion, respectively) are coupled together to align the towers, and the rod is swung around through a separate incision superior or inferior to the towers in a pendulum fashion. Once the rod is swung in place, locking caps are placed through the towers and tightened. Alternatively, most of the existing systems insert the rod through one of the towers and then turn the rod approximately 90° to capture the other screws in the other towers. Inserting the rod through the screw heads in a minimally invasive system is done blindly, e.g., without direct visualization of the screw head. Thus, this process is sometimes tedious and frustrating.

The Sextant™ system and other existing systems that use towers are hindered by both the number of incisions required. The use of a separate tower for each screw requires a separate incision for each tower, or a single incision long enough to accommodate two towers. The Sextant™ system also requires an additional incision for the rod, equaling six incisions (three on each side) for a single level fusion and eight incisions for a two level fusion. The other existing tower systems that use the direct rod insert and turn mechanism still require one incision for each screw and each incision has to be larger than the size of a tower through which the screws are inserted. Typically, each incision is at least 15 mm in length. When the sum of the lengths of all incisions on both sides are totaled, the total length of the current leading minimally invasive systems often are longer than the single midline incision of a traditional "open" approach for a single or two level pedicle screw fusion.

Furthermore none of the current MIS pedicle screw systems has been designed to take advantage of the lumbar lordosis that is typically present in most patients. About 80% of lumbar pedicle screw fusions are performed at the lowest two levels L4 to L5 and L5 to S1. These lowest lumbar levels also typically exhibit the strongest lumbar lordosis such that pedicle screw tracts through L4, L5, S1 and even L3 often intersect near a single point often near the skin similar to spokes on a bicycle tire. For most pedicle screw systems, this lordotic curvature is a hindrance in which the towers of the pedicle screws all intersect and cross. Crossing of the towers make it difficult for these MIS screw systems to allow a rod to be placed through the channels of the towers.

U.S. Pat. No. 7,306,603 entitled "Device and method for percutaneous placement of lumbar pedicle screws and connecting rods" by Frank H. Boehm, Jr., et al. and assigned to Innovative Spinal Technologies (Mansfield, Mass.), the entirety of which is hereby incorporated by reference, discloses a system of connecting a rod to the pedicle screws using a pin and recesses within the screw heads. According to this system the rod can pivot about a longitudinal axis of the pin between a first position in which the rod is parallel to the longitudinal axis of the screw (e.g., vertically oriented) and a second position in which the rod is transverse to that axis in order to bridge screws on adjacent vertebrae. The '603 patent teaches various guide systems (see FIGS. 5 and 6), rod holder systems (see FIGS. 8, 9, 10, and 11), and a rod guide system (see FIG. 12) but does not include a sleek, detachable system among them. Rather, the systems illustrated are tower-like with rather bulky dilators (80 and 86 in FIGS. 6 and 8), sheaths (81 in FIG. 6), and/or outer housing (120 in FIGS. 11 and 12).

U.S. Publication No. 2008/0140075 entitled "Press-On Pedicle Screw Assembly" by Michael D. Ensign and assigned to Alpinespine, LLC (American Fork, Utah), the entirety of which is hereby incorporated by reference, discloses attaching the rod to screw heads indirectly via a tulip assembly. The tulip assembly has a housing with an inner diameter smaller than an inner diameter of the screw head such that it is easily pressed into position upon the screw head. The rod is then placed by attaching directly to the tulip assembly after connecting the assembly to the screw head. The publication mentions using a Kirschner guidance element (or K-guidance element) for inserting both the pedicle screws and the tulip member (see [0030], [0032], and [0045]) but does not disclose how the rods are guided into position.

U.S. Publication No. 2008/0097457 entitled "Pedicle screw systems and methods of assembling/installing the same" by David R. Warnick and unassigned, the entirety of which is hereby incorporated by reference, like the '075 Publication, also discloses using a tulip assembly as an intervening means to join a rod to the screws. In this system, rather than a press-on locking mechanism, the structure is tightened by rotating an inner member and outer housing of the tulip assembly relative to one another.

U.S. Pat. No. 7,179,261 entitled "Percutaneous access devices and bone anchor assemblies" by Christopher W. Sicvol, et al. and assigned to Depuy Spine, Inc., the entirety of which is hereby incorporated by reference, describes one of the several tower systems for placement of pedicle screws percutaneously. The patent describes a situation where the angle of the screws intersect, and the towers may interfere with each other. This situation is rather typical in the lordotic lumbar spine, especially the lumbo-sacral (L5, S1) junction. In order to solve this problem, they describe cutouts in the tubes so that two tubes can intersect. Given that the angles of the vertebrae are variable from patient to patient and the depth of the vertebrae from the skin is also highly variable, the variations on the cutouts would have to be numerous. Additionally, when two tubes intersect at the cutout as shown in FIG. 22B in the '261 patent, the edges of the cutout of one tube interferes or blocks off the lumen of the other tube, and vice versa. This occurs because the muscle and tissue surrounding the tubes will push the tubes together at the section of the cutouts thereby significantly reducing the lumen through which the rod and other elements are inserted. The only way to avoid this interference or blockage of the lumens is to keep the tubes separate that would necessitate a larger incision and would eliminate the need for cutouts in the first place. Additionally a 2 or 3 level fusion requiring 3 or 4 screws that may be intersecting would be problematic if the towers on the screws were intersecting.

SUMMARY

Embodiments of the present disclosure are directed towards, but not limited to, improving minimally invasive (optionally adaptable for use with the percutaneous or endoscopic approach) TLIF and PLIF approaches and backing up the ALIF, DLIF™, and XLIF™ approaches. TLIF provides several advantages including: (i) stabilization of both the anterior and posterior portions of the spine through one or more posterior incision(s); (ii) the ability to fill with bone graft material a greater volume and diversity of spaces (front disc space with the spacer, amongst the screws and rods on the sides, and in the back of vertebrae) increasing the chances of a successful stabilization through the development and solidification of bone; (iii) the spacer placed within the front disc space maintains the natural interbody disc height to reduce pressure on nerve roots (from bone spurs, thickened, ligaments, etc.); and (iv) enhanced safety because the spinal canal is accessed from one side only and this reduces the risk of pinching, stretching, or otherwise agitating the spinal nerves.

Embodiments of the disclosure provide a system, device and/or method for performing a minimally invasive posterior and/or transforaminal lumbar pedicle screw fusion or stabilization procedure. Hereinafter references to "fusion" implicitly include stabilization which offers somewhat greater motion short of completely fusing the bone. Likewise, hereinafter references to "stabilization" implicitly include fusion. The main situations in which a surgeon can use the disclosed system can include a minimally invasive TLIF procedure with either: (i) a micro-lumbar interbody fusion, MLIF™, or (ii) mini-open TLIF on the symptomatic side to decompress the neural compression, and a pedicle screw fusion through a minimally invasive incision on the contralateral side. Similarly, the system disclosed herein would be used bilaterally in a PLIF approach with the decompression and interbody spacer placement performed bilaterally. Alternatively, the disclosed system is ideal for "backing up" (with a minimal posterior incision) anterior interbody fusions (ALIF) and lateral interbody fusions (XLIF™ and DLIF™). MLIF™ collectively encompasses (i) transforaminal lumbar interbody fusions and stabilizations, (ii) posterior lumbar interbody fusions and stabilizations, (iii) anterior lumbar interbody fusions and stabilizations, and (iv) lateral lumbar interbody fusions and stabilizations through a minimally invasive "micro" approach using the guidance system described herein, and (v) posterolateral instrumented fusions where only pedicle screws are placed for posterolateral fusion without using interbody spacers or implants. Since the lateral fusions such as the XLIF or DLIF are truly minimally invasive, a minimal posterior incision for backing up the lateral interbody spacer with pedicle screw fusion would be very complementary. Lateral interbody fusions are becoming more popular and more spine companies are coming out with their own lateral interbody fusion systems. It will be appreciated that although certain embodiments described herein are directed to minimally invasive procedures through a single skin incision, the systems and methods may also be used in open surgery or mini-open procedures through openings in the skin of a patient as desired by the practicing surgeon.

The lumbar spine has a lordotic curvature such that the lowest levels, L4, L5 and S1, have a posteriorly concave orientation or alignment, while the upper levels, L1-L3, are less lordotic. This curvature sets up a unique situation in which the trajectories through the pedicles (the trajectories to insert the pedicle screws) from L2 to S1 are not parallel. Rather, the trajectories commonly intersect at a point around the level of the skin. This configuration is similar to the spokes of a wheel in which the spokes (trajectories) meet at a common center point (a hub). Given that many patients have such a lordotic configuration of the lumbar spine, it is possible to insert pedicle screws through a single incision centered in the middle of the lumbar curvature. However, if each screw required a separate tower (or tube) (as in conventional tower/tube systems) in order for multiple screws to exist simultaneously, then the sum cross sectional area of the towers/tubes does not permit a single small incision. The towers/tubes interfere with each other and get in the way of one another due to their size. It is also difficult to place the rod through the channels of the towers and into the seats of the pedicle screws when the towers of the pedicle screws are crossed and not aligned in a straight line.

An alternative method is necessary in order to minimize the number and size of incisions. Reducing the number and size of incisions minimizes the tissue trauma needed to place pedicle screws for lumbar stabilization or fusion. An ideal system and procedure would take full advantage of the natural curvature of the lumbar spine in order to provide this reduction. However, the apparatuses and methods of the present application described and claimed herein are not limited to applications in the lumbar vertebrae and may also find use for fusing, stabilizing, or otherwise treating vertebrae in other regions of the spine such as the cervical spine where lordotic curvature is again the typical anatomical alignment.

The number of osteoporotic spinal patients requiring surgical intervention is increasing. Historically this complex group of patients has had complications with bone-screw fixation due to the nature of the bone and types and projection geometries of the screws used, along with their methods of insertion. These complications include implant failure, screw loosening and pullout. Recent research suggests new cortical screws that project in an anteromediolateral direction have advantages over traditional screws projecting in an anteromedial direction. Embodiments of the present disclosure take this research into account and can be used in guiding and placing new cortical screws to project in an anteromediolateral direction in order to overcome many problems of traditional screws in osteoporotic patients. Further, embodiments of the present disclosure can be used to place multiple new cortical screws through a single incision, minimizing trauma to already sensitive osteoporotic patients.

One objective of certain embodiments the present disclosure is to provide a simple method and associated apparatus to place two or more pedicle screws through one small hole. This provides a better cosmetic and functional result with just a single skin incision of small size (approximately 0.5 to 4 cm in length, approximately 0.5 to 3 cm in length, or approximately 1 to 2 cm in length) regardless of the number of screws used. In one embodiment, the single incision is smaller than the sum of the maximum widths of two respective largest elements for each screw that is inserted through the single incision, where an element includes the screw, screw head, rod, locking assembly and associated tools.

Another objective of certain embodiments of the present disclosure is to be able to insert, position, and manipulate a spinal implant such as a rod and a locking assembly through the same small incision in order to lock the rod within the screws. Certain embodiments provide novel ways to insert a rod into the heads of pedicle screws and ways to lock the rod within the screws through a single small incision. The systems and methods involve in certain embodiments the attachment of guide elements consisting of the following: one or more flexible wires, flexible yet firm extended blades, extended tabs, or towers attached to each pedicle screw head to be used to guide the rod down to the screw. The guide elements are configured and combined so that they can overlap or intersect at or below the skin incision, thereby enabling the use of a small, single skin incision. The screws, rods, and locking assemblies can all be placed through a single small incision and yet still be appropriately interconnected within because of the natural lordotic curvature of the lumbar spine. By attaching at least one guidance element on each side of the screw head, the guidance elements assist to align the screw head. The guidance elements also trap or restrict displacement of the rod, forcing it to fit between them and directly into the screw head.

Compared to U.S. Pat. No. 7,179,261 to Sicvol described above, embodiments of the present disclosure eliminate the need for "cut-outs" where the guide elements intersect. For example, in embodiments utilizing extended tabs or blades, these extended tabs or blades do not have a proximal, distal, or any lumen, and the configuration of guidance elements (extended tabs or blades) for screws at adjacent levels allow the tabs to intersect and overlap completely for any patient with any relative geometries. Thus interference between adjacent guidance elements on adjacent vertebrae is not a problem. Also, in the cut-out tubes taught by the '261 patent, a rod or other element would still have to be inserted through the tube at some point. The cut-out tubes require that the rod (or other inserted element) is oriented longitudinally parallel to the long axis of the tube as it is directed into the body until it reaches a section with side wall openings or slots distal to the cut-out section, at which point it may optionally be turned perpendicularly to the long axis and directed out of the side wall through the opening or slot. In embodiments of the present disclosure by using guidance elements such as extended blades or extended tabs (from the screw head), the element that is guided by them and inserted along them (e.g., a rod, a locking assembly etc.) does not have to be inserted through any lumen. When a rod is inserted using the blades, the blades can simply be fed through the outer edges of the rod body, through a retaining element or clasp attached to the rod body, or between the outer edges of the rod body and a retaining element (retention thread). Thus, it is possible for the inserted rod or other elements to be oriented perpendicular to the long axis or oriented in any other manner or at any angle during the entire entry pathway. This provides greater flexibility for avoiding interference between adjacent stabilization system pieces and eliminates the need for a surgeon to identify the cut-out sections before turning the screw/rod perpendicularly and/or reorienting it. Furthermore, since there are no lumens proximally or distally with the extended tabs, blades from adjacent levels may overlap and intersect without the need for cutout therefore allowing all blades to exit a single small minimal incision.

The guidance elements can also be used to guide the locking assemblies down to the screw heads for embodiments in which the locking assembly is not part of the screw head itself (and already down there).

Another embodiment is a hybrid system where each screw is placed through short towers or tubes that do not come to the skin surface. Wires, blade or tab extensions are attached to the top of the towers or tubes so that the screw, rod, locking assembly, and tools used for insertion, adjustment, locking, compression, distraction, and removal are guided by the extensions close to the skin but through individual towers or tubes close to the bone and pedicle screw. This hybrid system offers both the advantages of the wires/extended blades/tabs in which many guidance elements can overlap in a single incision at the skin level and the advantages of a tower or tube system are preserved at the bone level. Some surgeons who are comfortable with the tower system but who want the advantages of the blade/tab system may want to use this hybrid system.

Making some of the guidance elements telescopic allows for more guidance elements to fit through a single incision smoothly, thereby advantageously reducing the need to have a larger incision and/or multiple incisions. After insertion, the various guidance elements may be deployed telescopically as needed. Using telescoping components as part of the upwardly directed extended guidance elements allows a rod for stabilizing vertebrae to be inserted into the body through the telescoping components and through the same singular incision, minimizing invasiveness of the procedure.

All combinations and arrangements of towers, tubes, blades, arms, tabs, wires, and other upwardly directed extended guidance elements, either as described herein or in hybrid systems which combine conventional tower/guidance elements as described in the prior art (such as described in the references incorporated by reference throughout this specification) are contemplated as within the spirit and scope of the present disclosure. As used herein, the term guiding or guidance element is intended to include one or more components extending between a screw and a skin incision, preferably directly or indirectly coupled or detachably connected to a screw head, and includes both conventional towers or tubes such as those made of rigid or semi-rigid materials as described in the patents and publications incorporated by reference throughout this specification, as well as the additional embodiments of guiding or guidance elements as described herein. The most suitable selection and arrangement is for the surgeon to determine in each particular case. For example, in one embodiment, there may be telescoping tubes at one level, wires at the next level, and blades at the next level on one side (of the slot for the rod) with blades attached to wires on the other side (of the slot for the rod). Different variations may be selected for each side (medial, lateral) in order to introduce more components through the same incision. The goal is to provide enough guidance elements to properly guide the stabilization rods, locking assemblies, tools, etc. to the pedicle while minimizing the number of incisions and preventing overcrowding Eliminating overcrowding permits proper visualization so that the surgeon can work comfortably and efficiently.

In some embodiments, a system is provided for performing spine stabilization through an opening in skin of a patient. In some embodiments, the opening may be a single, minimally invasive skin incision. The system comprises a first screw having a screw head and a first guiding element comprising a height component detachably connected to the first screw, the first screw being configured for implantation in a first vertebra. The system also comprises a second screw having a screw head and a second guiding element detachably connected to the second screw, the second screw configured for implantation in a second vertebra. The first screw with the first guiding element and the second screw with the second guiding element can be delivered into the first and second vertebra.

Other objectives and advantages of embodiments of the disclosure will be set forth in the description which follows. Implicit modifications of the present disclosure based on the explicit descriptions will be, at least in part, obvious from the description, or may be learned by practice of the disclosure. Such subtle, predictable modifications and adaptations are taken to be within the scope of the present disclosure. Additional advantages of the disclosure may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIGS. 1B and 1C illustrate how the offset extended blades/tabs function in operation to intersect/cross without interference as the blades/tabs extending from one screw head pass inside/outside the blades/tabs extending from another adjacent screw head such that the two could pass through the same incision. FIG. 1B is a side view and FIG. 1C is a head-on perspective view.

FIG. 3A illustrates the pedicle screw being inserted into the pedicle portion of a vertebra on the anatomical right side of the central lamina.

FIG. 3B illustrates two pedicle screws in position on two adjacent vertebrae on one side of a vertebral column, with the screw shafts buried within the vertebral bones and the U-shaped screw heads protruding from the pedicles' surfaces. Also shown is a rod being guided down (at an angle) to the screw heads, between each of two sets of two guidance elements, one for each screw.

FIG. 3C illustrates the rod in a proper final position fully inserted within the screw heads of the pedicle screws in adjacent vertebrae along one side of a vertebral column for a partial (half-finished, the other side having yet to be stabilized) one-level stabilization. The locking assemblies are not shown here but may also be guided by the guidance elements down to the screw heads.

FIG. 4C illustrates a rod inserted through a first plurality of telescopic tubes being guided out of a first window in a first lowermost tube and into a second window in a second lowermost tube of a second plurality of telescopic tubes.

FIGS. 9A-9E illustrate an embodiment of a system for stabilizing spinal vertebrae comprises a hybrid combination of guidance elements. As illustrated, each of the pedicle screws in the illustrated system comprises a plurality of wires, wherein the plurality of wires are configured to guide a cannulated tower to the inserted pedicle screw.

DETAILED DESCRIPTION OF THE EMBODIMENTS

Overview

Figure 1A:
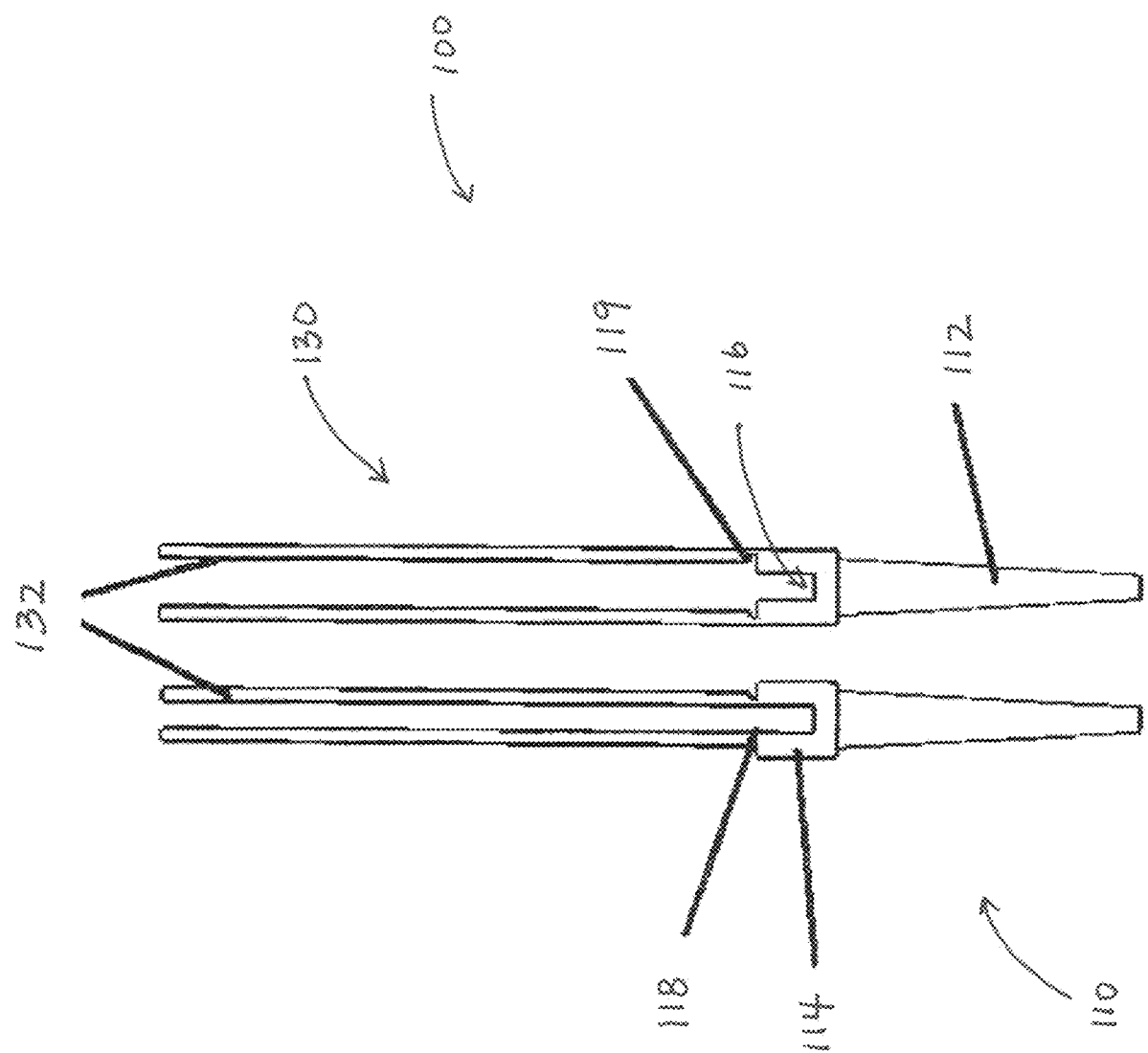
FIG. 1A illustrates an embodiment of guidance elements as offset extended blades/tabs attached to screw heads with the extended blades attached to the outside of one screw head and the inside of another screw head.

The present disclosure involves improved systems, apparatuses and methods for guiding one or more screws, rods, and locking assemblies down to the vertebrae and for securing a rod or other spinal implant to stabilize the vertebrae. An embodiment of a system for stabilizing spinal vertebrae 100 is illustrated in FIG. 1A. In some embodiments, the system for stabilizing spinal vertebrae 100 can include pedicle screws. As illustrated in FIG. 1A, in some embodiments, the screw 110 can include a bone engaging shaft 112 and a screw head 114. In some examples, the bone engaging shaft 112 is threaded. The bone engaging shaft 112 may be relatively moveable to different angles relative to the screw head 114. In some embodiments, the screw head 114 has generally a U-shape, as shown in FIG. 1A, defining upwardly extending arms that form a channel for receiving a rod 120 (illustrated below in FIGS. 3A-3C). The rod 120 may either sit on the head of the bone engaging shaft 112, or may sit on an insert 116 placed in the screw head 114 for receiving the rod 120. U.S. Pat. No. 8,721,691 entitled "Systems and Methods for Pedicle Screw Stabilization of Spinal Vertebrae" by Sherwin Hua and unassigned, the entirety of which is hereby incorporated by reference, discloses related embodiments of various spinal stabilization systems.

A locking assembly may be built into or attached onto the screw head or be a separate element. Locking assemblies that are separate elements include (but are not limited to) those reliant on caps and set screws. Locking assemblies integrated with the screw head can include (but are not limited to) rotatable mechanisms in which a turn of the screw head traps the rod. The locking assembly may be guided down to the screw before or after insertion of the rod depending upon the details of the locking mechanism used to secure the rod. In some embodiments, the locking assembly is already present on the screw head before the rod is received. In some examples, the rod is inserted into the screw head 114 first and the locking assembly follows. In some embodiments, the upwardly extending arms of the screw head 114 may be internally threaded to receive an externally threaded cap screw that is rotated into the screw head 114 to apply a downward force to a rod 120 sitting in the channel of the screw head 114. This downward force may also then lock the position of the screw head 114 relative to the rod 120.

The guidance elements for directing the rod 120, various locking assembly components (e.g., screw head caps), surgical insertion and manipulation tools, and other components into position may be any type of upwardly directed, extended guidance elements. These guidance elements are preferably detachably connected to the screw heads or screws so that they can be easily removed once a procedure is completed. Suitable guidance elements include: tubes, towers, blades, arms, extended tabs, wires, string, etc. In some embodiments, the guidance elements extended tabs or extended blades run from a site adjacent the screw head up through the incision site. FIG. 1A illustrates a system for stabilizing spinal vertebrae 100 having guidance elements 130 including a plurality of blades 132. In some examples, the guidance elements can be curved (along one or more axis) or bent (along one or more axis) to accommodate the cap and other components. The guidance elements may also be curved or bent in order to be offset from adjacent elements such that they do not interfere if and when they cross. The curvature may be a permanent rounded shape or they may be flexibly curveable or comprised of foldable panels. The curves and bends may be permanent and pre-formed or adjustable in situ. The extended guidance elements may also be tapered, threaded and/or notched to assist in stabilizing the cap or other components as they are lowered down to the screw head.

In some embodiments, the guidance elements comprise two or more blades that may be offset from each other. In some examples, the offset configuration of the two or more blades allows the two or more blades to cross as the two or more blades do not interfere with each other. FIG. 1B illustrates the system for stabilizing spinal vertebrae 100 wherein the plurality of blades 132 of the guidance elements 130 of each of the screws 110 is configured to cross and/or overlap as described above. In some examples, the guidance elements can be offset in any functional manner, and can assume different positions around the screw heads (e.g., for staggered crossing), bending at different positions (e.g., straight to bent), curvatures that are non-intersecting with adjacent elements (blades from adjacent screw head), etc.

The extended tabs/blades or other guidance elements on adjacent screws may be offset such that they do not interfere with one another when they intersect. Rather, as they cross one another, the extended tabs/blades (or other guidance elements) can be configured to smoothly pass by one another. Therefore the extended tabs/blades on adjacent screws can be inserted through the same small incision and manipulated within that incision. This may be achieved by tabs/blades, or other guidance elements, on the inside of one screw and the outside of the other screw. In some embodiments, the tabs/blades for adjacent screws can simply be staggered or misaligned. In some examples, one screw can have a single tab/blade on the medial side while another screw has a single tab/blade on the lateral side. In some embodiments, one screw can have extended tabs, while one or more of the other screws can have flexible wires as guidance elements.

In some embodiments, some of the extended guidance elements (tabs, blades, etc.) on some screw heads may be straight while those on others are bendable or angled, such that the bendable or angled elements cross over the straight ones to exit the body through the same skin level incision. In other embodiments, a first screw is connected to a first extended guidance element in the form of a plurality of blades and a second screw is connected to a second extended guidance element in the form of a plurality of blades. As illustrated in FIG. 1B, the plurality of blades of the first extended guidance element can overlap and/or intersect with the plurality of blades of the second extended guidance element. Advantageously the first extended guidance element and the second extended guidance element can intersect or overlap at or near a skin level incision. By intersecting or overlapping at or near a skin level incision, this allows both of the guidance elements to extend through a single, small incision.

The extended tabs/blades or other guidance elements are configured to easily detach from the screw head upon completion of directing rods, caps, instruments, and other components precisely to the screw head. This detachment process may occur by any number of means, including break-off along a pre-perforated or notched line, burning or melting at the base of the tabs/blades with an instrument, releasing a mechanical clamp, etc. In some embodiments, the extended guidance elements (e.g., extended tabs, extended blades, etc.) for adjacent screws may be attached to their respective screw heads at different positions along the screw head to produce the offset configuration. In some examples, the extended guidance elements may be attached to their respective screw heads at the same location and bent at different angles to form different configurations that are offset with respect to one another when crossed. For example, the extended guidance elements may be bent to come out of the screw head at different lateral displacements such that they do not interfere with one another. In some embodiments, for a two level fusion, three offset extended guidance elements (tabs, blades, etc.) attached to three adjacent screws can be used. In some examples, for a three level fusion, four offset extended guidance elements attached to four adjacent screw can be used. In some embodiments, for a level four fusion, five offset extended guidance elements attached to five adjacent screws can be used. In a level four fusion, potentially all of the five offset extended guidance elements can be configured to come through the same skin level incision and crossing at some point at or near the same level skin incision.

In some embodiments, the extended tabs/blades/arms and wires can work together in a "hybrid" concept. For example, a first tab/blade/arm can be attached to the screw head and is configured to be easily detachable. Additional tabs/blades/arms between the screw head and distal wires protruding from the skin can be added and/or removed as needed to lengthen or shorten the distance of the guidance trajectory. In some embodiments, the guidance element can include a multitude of breakoff tabs/blades/arms that are attached to one another in series to create a long extended blade. The blade can then be tailored to the appropriate length, such as at the level of the skin incision, by breaking the tabs off at the closest breakoff point to the desired length. In some embodiments, one or more of the breakoff tabs can be attached to a proximal wire to keep track of and locate the tab within the patient.

In some embodiments, flexible guidance wires can be used to direct other guidance element features (e.g., tabs, blades, arms) during insertion and removal. The guidance wires can serve as a guide to direct add-on tab elements into place within the patient. In some examples, a plurality of flexible guidance wires can serve alone as guidance elements to guide rods, tools or locking assembly components to a desired location at or near the spine. In some embodiments, the flexible guidance wires can be part of a "hybrid" concept and can work in conjunction with tabs/blades/arms to guide elements to a desired location. The rods, tools or locking assembly components can be delivered via the guidance elements by hand, or in some embodiments, using a stereotactic guidance mechanism and/or by a robot.

Additional embodiments of systems and methods for pedicle screw stabilization of spinal vertebrae are also disclosed in U.S. Pat. No. 8,721,691," the entire contents of which are hereby incorporated by reference in its entirety.

As used herein, distal is defined as a space farther from a particular location, and proximal is defined as a space closer to the particular location. In some embodiments, a portion of a tab or blade that extends out beyond an incision can be considered a proximal portion, while a portion of a tab or blade that is beneath the incision can be considered a distal portion.

Stabilization System With Guidance Elements Comprising A Plurality of Blades

Figure 1C:
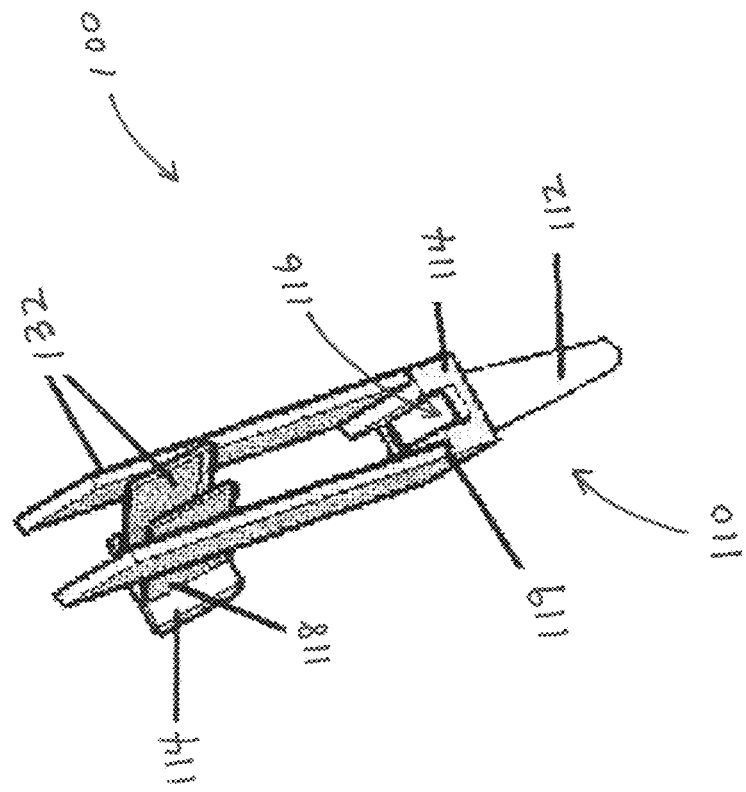

As described above, FIG. 1A illustrates a system for stabilizing spinal vertebrae 100. In some embodiments, the system for stabilizing spinal vertebrae 100 is configured to deliver a rod through an incision to a desired location in a patient. In some examples, the system for stabilizing spinal vertebrae 100 can include a first screw 110 having a screw head 114 with a pair blades 132 connected to an inside wall perimeter 118 of the screw head 114. In some embodiments, the system for stabilizing spinal vertebrae 100 can include a second screw 110 having a screw head 114 with a pair of blades 132 connected to an outside wall perimeter 119 of the screw head 114. In some embodiments, each of the pair of blades 132 form a different sized passageway or channel through which an implant (e.g, a rod member) or guide tool can be delivered. For example, the pair of blades 132 attached to the first screw head 114 creates a narrower passageway than the pair of blades 132 attached to the second screw head 114. Moreover, the system is configured such that the blades or tabs in an inside wall perimeter 118 attached to the first screw 110 can advantageously criss-cross or intersect with the blades or tabs on the outside wall perimeter 119 of the second screw 110 (as shown in FIGS. 1B and 1C). The criss-crossing of the pair of blades 132 of the first screw 110 and the pair of blades 132 of the second screw 110 can occur at a single incision of small size, or near the single incision of small size.

In some embodiments, the system for stabilizing spinal vertebrae 100 is configured such that when the pair of blades 132 attached to an inside wall perimeter 118 of the first screw head 114 are criss-crossed at or near a single small incision with the pair of blades 132 attached to an outside wall perimeter 119 of the second screw head 114, an implant such as a rod member can be guided down the narrower passageway created by the pair of blades 132 connected to the first screw head 114. As will be discussed and illustrated below, the rod member can be guided such that one end of the rod is seated in a seat of the first screw head. The other end of the rod member can pass through the passageway created by the pair of blades 132 connected to the second screw head 114 and can be seated in the insert 116 of the second screw head 114. While other conventional systems allow for rod placement across two screw heads, the present system using criss-crossing blades at or near a small incision allows for a smaller, less minimally invasive incision in order to achieve the desired result. The criss-crossing blades can reduce the amount of trauma to the patient and reduce the amount of time required for healing.

FIGS. 1B and 1C illustrate how the extended blades 132 are offset (e.g. as they are attached on the inside wall perimeter 118 and the outside wall perimeter 119) such that in operation upon intersection (shown in both FIG. 1B from the side and in FIG. 1C head-on) they smoothly pass one another without interference. As such, adjacent extended blades 132 can pass through the same skin level incision and be manipulated easily through a range of geometries for final positioning. Further, the same devices can be used generally on all patients with different anatomical dimensions.

Stabilization System with Guidance Elements Comprising Wires

Figure 2:
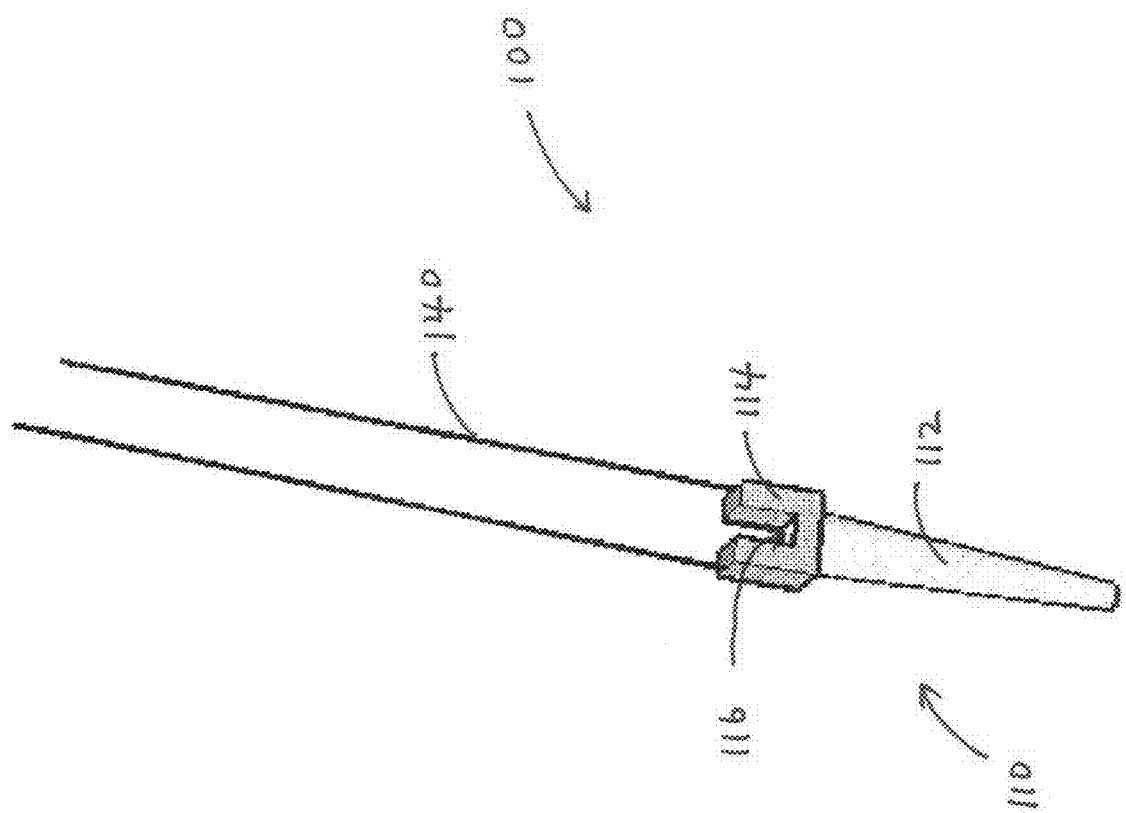
FIG. 2 illustrates a pedicle screw with a tapered shaft directed downwards and with a concave U-shaped screw head and detachable elongated guidance elements directed upwards (one on each side of the head). The elongated guidance elements may attach directly to the screw head. This configuration forces the screw head and the rod to align with each other as the rod is lowered into the seat of the screw head.

In some embodiments, the disclosed systems and methods are configured to use a guidance element 140 on each side of a screw head 114 (as shown in FIG. 2) such that there are two guidance element 140 per screw rod 120 to securely trap a rod 120 over the screw bone engaging shaft 112 within the screw head 114. This embodiment is believed to provide a very high degree of rod 120 stability, while maintaining a very low volume of stabilizing elements (thereby enabling a very small incision without stressing it). The guidance elements 140 can be part of the screw head 114 as an extension of the screw head 114 itself. Or, the guidance elements 140 can be independent elements attached to the screw head 114 through (i) the guidance element itself, (ii) an extension of the guidance element that is formed of a material that is the same as a material from which the guidance element itself is derived, (iii) a thread material thinner than the guidance element, (iv) a short tower, or (v) an intermediate element including an extensor/extended tab, flexible sheet, flange, or mechanical device/clamp as discussed further herein, among other possibilities. A single guidance element 140 may be attached to a screw head 114 at a single location or in two or more locations as illustrated in FIG. 2. If the screw head has edges or corners, guidance elements attached to those corners will eliminate the possibility that a rod or locking mechanism is caught on the edge or corner during insertion of the same.

As illustrated in FIG. 2, in some embodiments, a single guidance element 140 illustrated in the form of a single wire is attached to the screw head 114 having a first wire portion extending from one side of the screw head and a second wire portion extending from the other side of the screw head 114. In some embodiments, the two wire portions in one embodiment may be separate wires.

Method for the Placement of Pedicle Screws and Rods Using Wires

FIGS. 3A-3C illustrate the steps for the placement of the pedicle screws and rods using a screw 110 including a plurality of guidance elements 140. First, using fluoroscopy or stereotactic guidance, a single small skin incision 1-4 cm lateral to a midline that will accommodate all pedicle screws is localized. Next, using either a percutaneous Jamshedi/Kirschner-guidance element (K-guidance element) approach, a Wiltse muscle splitting approach, or tube system, the pedicle screws are placed (see FIG. 3A). In some embodiments, the pedicle screw inserter may have loop attachments that hold the side guidance elements of the pedicle screw during placement. In some examples, the insertion tool or device that positions the pedicle screw may have protrusions (or slots/grooves) that mate with corresponding slots/grooves (or protrusions) on the upwardly directed extended guidance elements. Once the pedicle screw is placed, the insertion tool or device can be removed to make room for the placement of the other screw(s), the rod, and optionally, a separate locking assembly.

After each pedicle screw is placed, the side guidance elements are pushed to the side(s) of the incision to make room such that additional screws can be placed around or between the guidance elements already in place. In some embodiments, it is preferable to insert additional screws in between the guidance elements of the first screws for cases where pairs of wires, blades, or tabs are used. After all screws are placed, a screw head turner is inserted and guided down to the screw heads along each pair of guidance elements to align the heads of the screws in preparation for receiving the rods. As illustrated in FIG. 3B, each of the screw heads 114 are aligned.

Once each of the screw head 114 are aligned, the guidance elements 140 are split between the medial and lateral sides. As shown in FIG. 3B, a rod 120 is slid in between the medial and lateral guidance elements 140 into the first and second screw heads 114. In some examples, the rod can be sized and bent before insertion. In some embodiments, the plurality of guidance elements 140 include markers at predefined distances from the tip of the guidance elements can help guide the surgeon in correctly sizing and bending the rod.

In some embodiments, the plurality of guidance elements 140 extending out of a single incision are similar to light rays that have been focused by a convex lens. These light rays converge at a point and then create a mirror virtual image on the other side of the focal point. As shown in FIG. 3C, a similar concept can be used to create a mirror image of the rod to guide the sizing and bending of the rod to accurately fit into the screw heads. The depth of each guidance element 140 relative to the intersection point near the skin incision is reflected outwardly on that same guidance element and equal distance away from the intersection point. By connecting the reflected points on the guidance elements 140 proximal to the intersection point, a virtual image of the curvature and length of the rod is accurately estimated. The rod 120 can then be lowered through the guidance elements 140 by one or a combination of mechanisms including retention threads, rod holders that are guided by the guidance elements, and rod wires. After each end of the rod 120 is properly positioned within a screw head, locking nuts or caps are screwed on the screw heads to secure it in place. In some embodiments, a compressor that is guided by the guidance elements 140 are used to compress pedicle screws on adjacent levels. Subsequently, final tightening can be done during compression. Other instruments can also guided by the guidance elements, such as to compress, distract, or move one vertebra relative to another (e.g., for spondyloisthesis or scoliosis). The guidance elements are then removed by any means including cutting, twisting, wagging, burning, radiating, dissolving, unscrewing, etc. Once the screws and rods in all vertebrae to-be-fused along one side of the vertebral column are stabilized, the contralateral side can be similarly stabilized if indicated.

Embodiments of the present disclosure can be used to dynamically stabilize or fuse vertebrae while at the same time removing a defective intervertebral disc and inserting a spacer in its place. The spacer may include bone graft material or bone inducing material incorporated therein to encourage healing. Example bone inducing materials include bone morphogenetic protein, tricalcium phosphate, hydroxyapatite, and collagen.

The various elements (guidance elements, screws, screw heads, rods, retention threads, locking assemblies, etc.) may be provided in a range of sizes, shapes, strengths, flexibilities, and other physical characteristics to best accommodate individual patients and particular applications. Other embodiments include combining two or more of the elements mentioned so that the combined elements can be inserted together instead of one at a time. For instance a locking assembly that is attached to a rod or that is placed downwards together with a rod will save one separate step of placing the locking mechanism after the rod is placed. Similarly, a rod that is attached to the second screw head vertically by a hinge can then be swung down into the guidance element and screw head of the first screw after the second screw has been placed. A rod wire will further ensure that the tail end of the rod stays within the guidance element of the first screw. This combination saves the separate step of placing the rod into the incision.

While the illustrated guiding elements and accompanying disclosure discuss the delivery of a rod via the guiding elements, the guiding elements can also be used to deliver guiding tools designed to compress, reduce a spondylolisthesis, and/or provide counter-torque when locking the a rod member in place. In addition, various other tools can be provided to assist in stabilization, such as dynamic stabilization.

Stabilization System with Guidance Elements Including Wires

Figure 4A:
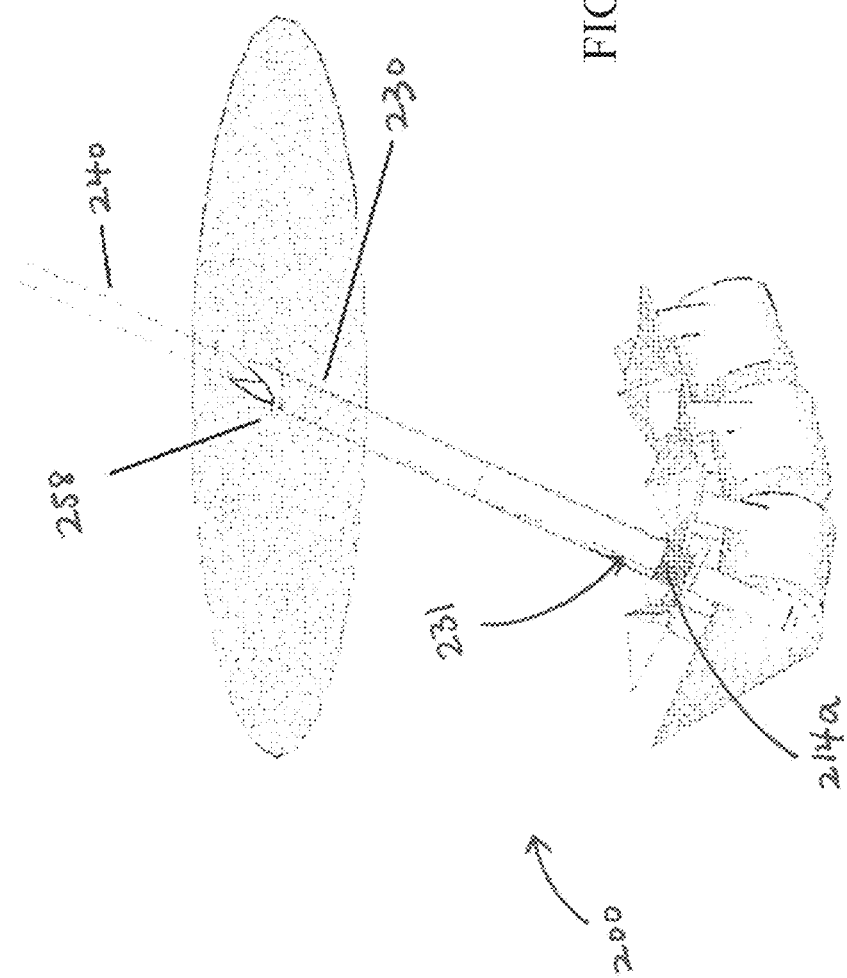
FIGS. 4A and 4B illustrate various arrangements of guidance elements comprising guidance elements connected to wires at the skin level incision. The guidance elements go from wider to narrower along a trajectory extending from the pedicle of the vertebra to the incision.

In some embodiments, the system for system for stabilizing spinal vertebrae 200 can include one or more assemblies of guiding elements that are disposed over and/or operably connected to a plurality of extension members. The embodiments illustrated and described in FIGS. 4A-4C disclose a plurality of telescopic guiding elements, however the guiding elements can be non-telescoping and can have any configuration (e.g., telescoping towers, tubes, blades, arms, or extended tabs). FIG. 4A illustrates an assembly comprising a telescopic guiding element 230. The distal end of the telescoping guiding element 230 is positioned closest to the screw head 214a of the screw 210 of a vertebra and is wider than the proximal end of the telescoping guiding element 230, which is positioned closer to the incision 250. In some embodiments, the incision 250 is at skin level.

The telescoping guiding elements may progress from wider near the vertebrae to narrower near the skin. For example, in some embodiments, the distal end of the guiding element 230 includes an internal width or diameter that is greater proximal end of the guiding element 230. In some embodiments, this can allow a portion of the proximal end of the guiding element 230 to "telescope" within the distal portions of the guiding element 230. The telescoping feature allows for adjustment of the height of the assembly of telescopic guiding elements, which advantageously results in less crowding closer to the incision 250 in order that more guidance elements from a greater number of vertebrae can fit through a single incision. In some embodiments, at the skin level incision 250, guidance elements from different vertebrae all converge on one another. In some embodiments, away from the skin level incision 250 and closer to the vertebrae the guiding element 230 diverge.

In some embodiments, as shown in FIG. 4A, the guiding element 230 can include a plurality of cylindrical tubes that can "telescope" (e.g., slide into and/or relative to one another) and assume various heights as an assembly. In some embodiments, each of the plurality of cylindrical tubes can move along a longitudinal axis relative to one another. In other embodiments, the guiding element 230 can include other shapes as well, including non-cylindrical elements. In the illustrated embodiment, the guiding element 230 includes three different tubular members; however, different embodiments can include any number of telescoping members. For example, a guiding element 230 can include only an upper guiding element and a lower guiding element, or in other cases, more than three telescoping guiding members. In addition, each of the telescoping guiding elements can have various internal widths or diameters, such that they can each be inserted individually through the single incision. In some embodiments, one or more tubes have a diameter of between about 14 mm and 25 mm and are capable of fitting through an incision of between about 14 mm and 25 mm.

As shown in FIG. 4A, one or more extension members 240 can be operably connected to the guiding element 230. In the illustrated embodiment of FIG. 4A, the extension members 240 comprise wires or threads operably attached to the proximal end of the guiding element 230. In the event that the plurality of telescoping guiding elements assume a reduced height (e.g., as shown by the guiding element 230 and guiding element 232 in FIG. 4B positioned below a skin incision), the extension members 240 can be configured to extend through and outside the incision and allow a user to properly identify the location the plurality of telescoping guiding elements of reduced height. In some embodiments, the extension members 240 can also advantageously serve as guiding elements themselves, such that rod members or other implants can be guided toward the plurality of telescoping guiding elements.

Figure 4B:
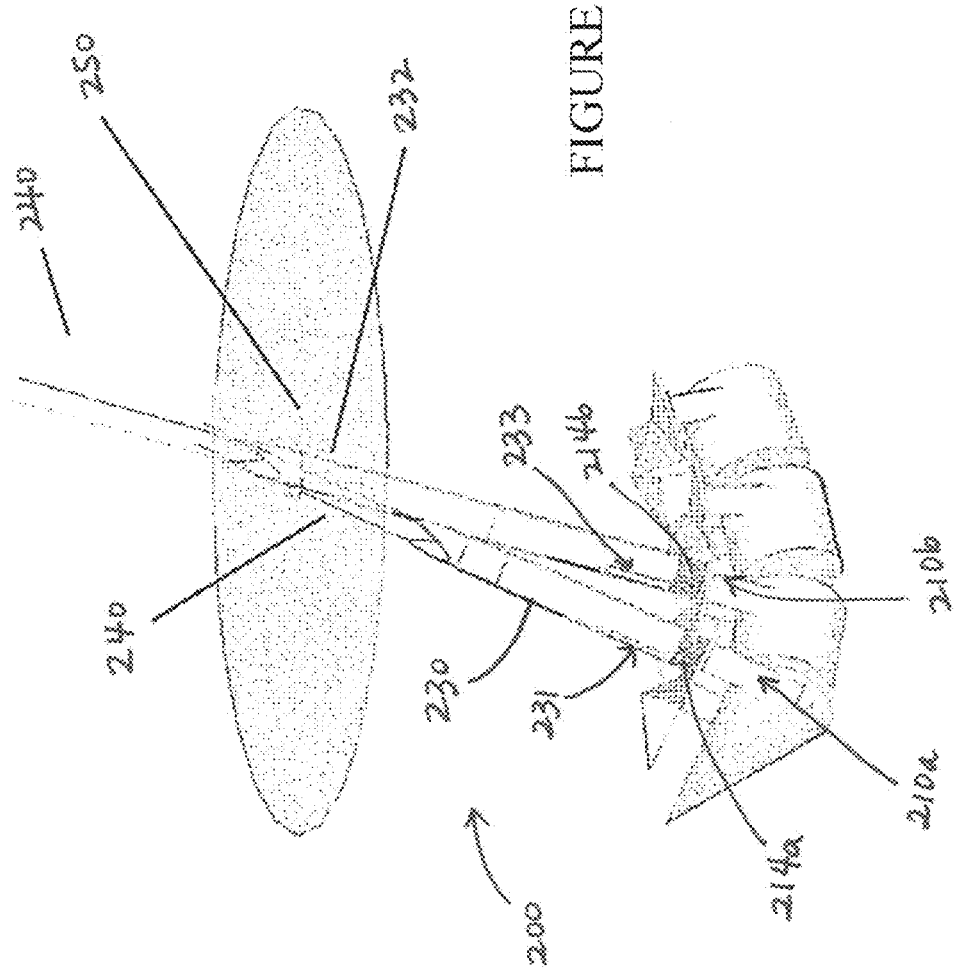

FIG. 4B illustrates the use of a first assembly comprising a guiding element 230 and a second assembly comprising a guiding element 232. As disclosed herein, the guiding element 230 and guiding element 232 are telescoping, however, the first and second assemblies illustrated in FIG. 4B can also be non-telescoping As discussed above, the first guiding element 230 can include extension members 240 in the form of wires that extend from the proximal end of the guiding element 230. Similarly, the second guiding element 232 includes can include extension members 240 in the form of wires that extend from a proximal end of the guiding element 232. As shown in FIG. 4B, after the screw 210a attached to the guiding element 230 is delivered into a vertebra, the height of the guiding element 230 can be reduced so that the proximal end of the guiding element 230 is positioned below the skin incision 250, but the wires of the extension members 240 extend out of the incision 250. In some embodiments, this can provide room for the screw 210b attached to the second guiding element 232 to be delivered into the vertebra. As shown in FIG. 4B, the second guiding element 232 can be inserted into a desired position via the same single incision 250, thereby reducing the amount of trauma to a patient compared to other guiding systems that require multiple or larger incisions.

FIG. 4C illustrates the delivery of a spinal implant in the form of a rod using telescopic guiding elements as discussed above. As shown in FIG. 4C, with the first guiding element 230 still reduced in height and the second guiding element 232 extending through the incision 250, a rod 220 or other implant can be inserted through the same singular incision as the guidance elements. The rod 220 can be inserted through a center of the guiding element 230 and guiding element 232. The rod 220 enters through an opening in a proximal end of the guiding element 232 as part of a second guidance element assembly attached to a second vertebra and is directed downwards to a distal end of the guiding element 232 as part of the same first guidance element assembly. The distal end of the guiding element 232 has a window 233 therein configured to permit passage of the rod 220 therethrough. In some embodiments, a first end of the rod 220 is passed through the window 233 of the distal end of the guiding element 232 of the second assembly of guidance elements and maneuvered until it enters a window 231 of a distal end of the guiding element 230 of a first guiding element 230 attached to a first vertebra. The first end of the rod 220 can be guided down the guiding element 230 and guiding element 232 until it enters a channel for receiving it in a first screw head 214a of a first screw 210a in the first vertebra (as shown in FIG. 32). Then the second end of the rod 120 is guided down the window 233 until it enters a channel for receiving it in a second screw head 214b of a second screw 210b in the second vertebra. In some embodiments, the height of the second guiding element 232 may be reduced such that the proximal end of the guiding element 232 is below the skin incision, with the extension members 240 extending through the incision 250. Using the extension members 240, the height of the first guiding element 230 may be increased to again extend through the skin incision 250. This first guiding element 230 may then be used to deliver instruments therethrough, for example to delivery a locking assembly to the pedicle screw. Further extensions and reductions in the height of the telescoping guiding elements may be employed as desired by the surgeon in order to perform appropriate procedures on the patient.

While the illustrated embodiment in FIG. 4C depicts the guidance of a rod implant down the telescoping guiding elements, the telescoping guiding elements can also help guide non-rod implants, as well as locking devices (e.g., cap members) and tools for compression, distraction, and various other spinal procedures.

Figure 5A:
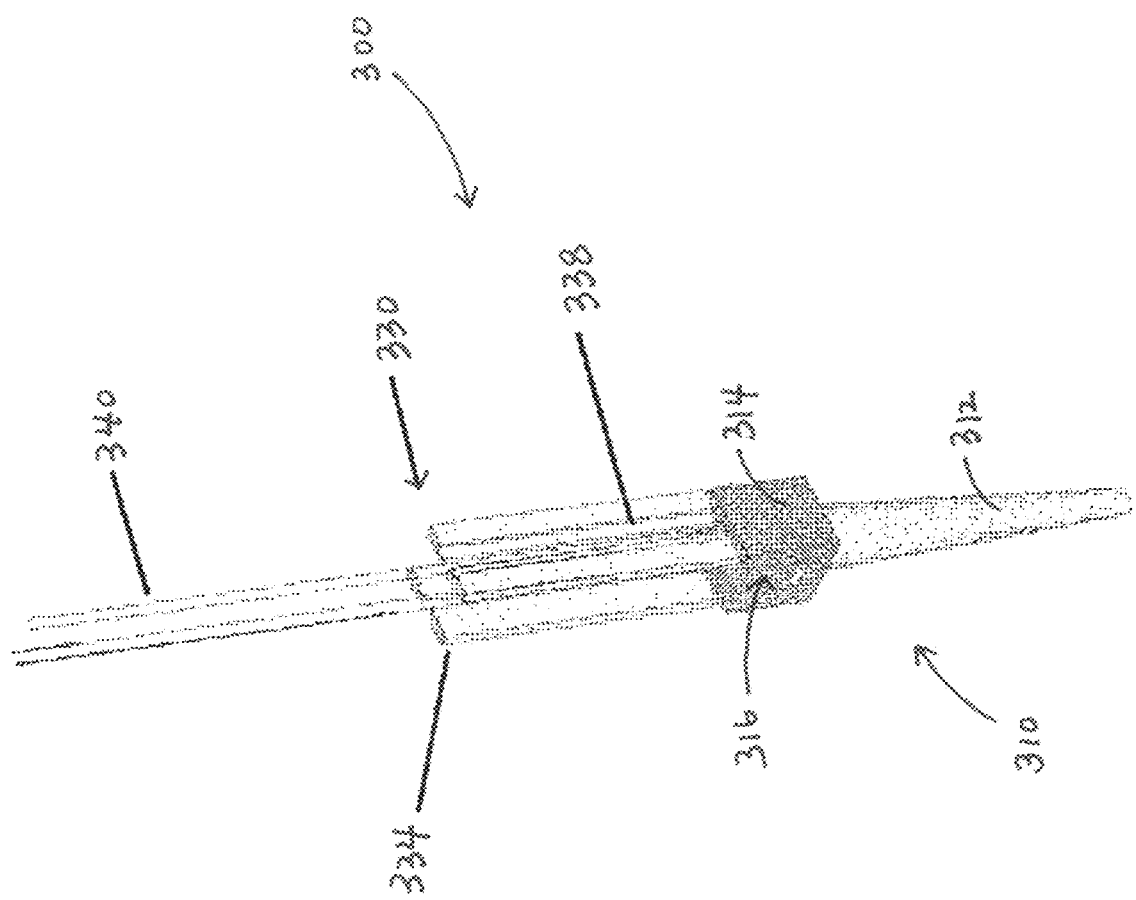
FIGS. 5A-5C illustrate another embodiment of guiding elements comprising guidance elements connected to wires, this time with guiding arms configured with an indentation that creates a groove or channel along the length thereof to receive a protruding portion of a locking assembly or other element, in order to guide the locking assembly down to the base of the arms, just above the rod.
Figure 5C:
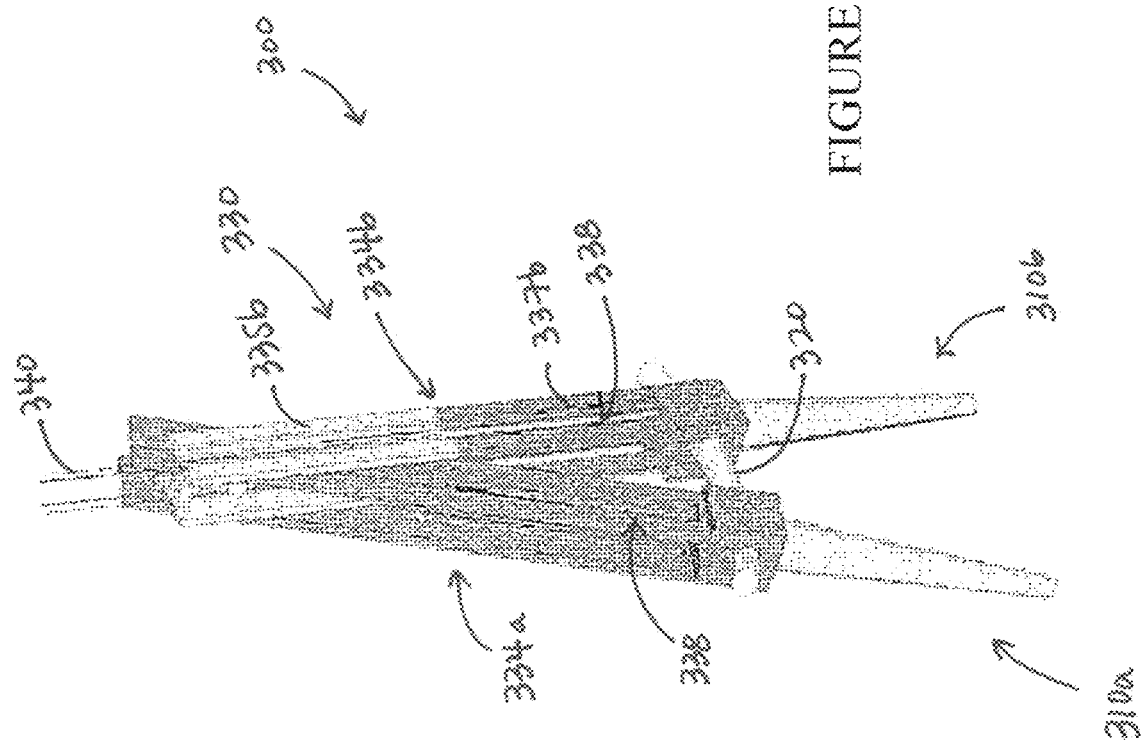
Figure 5B:
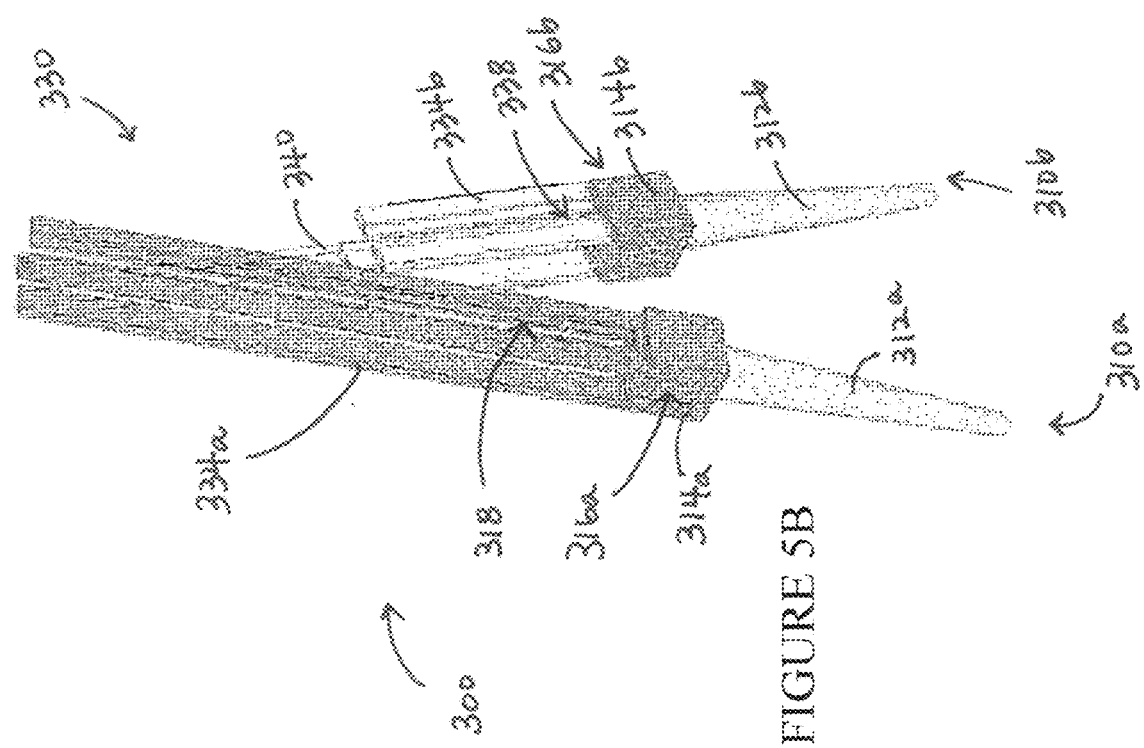

FIGS. 5A-5C illustrate an embodiment of a hybrid system utilizing at least one set of non-cylindrical telescoping guiding elements. As shown in FIG. 5A, the blades 330 can be a plurality of blades 334 that illustrate an example of a guiding element 330 that does not need to be cylindrical but can have other shapes. As illustrated in FIG. 5A, the blades 334 provide for a guiding element 330 that includes substantially rectangular arms or blades having squared edges that provide a channel or pathway for the delivery of a rod or other spinal implant therethrough. In some embodiments, the guiding element 330 may include wires 340 as described above. In some embodiments, the height of the guiding element 330 can be adjustable. For example, in some embodiments, one or more blades 334 can be adjusted by moving one segment of blades 334 relative to another. For example, as shown in FIGS. 5B and 5C, the blades 334b can be adjusted by moving an upper component 335b of the blades 334b relative to a lower component 337b of the blades 334b. In some examples, this can allow the height of the blades 334b to shorten or lengthen. In some embodiments, there is a friction mechanism that keeps the upper component 335b fixed at a specific position relative to lower component 337b. In some examples, the interior of the upper component 335b of the blades 334b is slightly larger than the interior of the lower component 337b of the blades 334b, thereby allowing relative sliding between the two members. In some embodiments, the guiding element 330 can include one or more groove 338 that are configured to provide a channel or pathway along the length of the blades 334. In some examples, the groove 338 is configured to receive a protrusion of a locking assembly, tool, or other element in order to guide it down to a delivered rod.

FIG. 5C illustrates the system for stabilizing spinal vertebrae 300 wherein the guiding element 330 can be extended using wires 340 that are configured to criss-cross or overlap with the blades 334a or blades 334b. As shown in FIG. 5C, a rod 320 can be guided and delivered to the screw 310a and the screw 310b using the blades 334a and the blades 334b respectively. With the blades 334a and the blades 334b extended, a screw cap locking assembly can be delivered to lock the rod 320 in place.

Similar methods as discussed above with respect to FIGS. 4A-4C are also applicable to the alternate embodiments of the guiding elements shown in FIGS. 5A-5C. Such methods can involve the use of one or more assemblies of guiding elements having adjustable height, whereby one assembly is at a height below an incision and the other assembly is at a height above the incision during use. In some embodiments, the assemblies of guiding elements are capable of crisscrossing or intersecting. Rod members or other implants can be delivered down the assemblies of guiding elements and into place into seats of the screw heads.

Stabilization System and Methods with a Hybrid Combination of Guidance Elements

In some embodiments, the system for stabilizing spinal vertebrae includes a hybrid combination of guidance elements. The goal is to minimize the incision size and tissue damage or disruption during the surgical procedure. The first screw placed into the first vertebrate uses flexible wires as guidance elements arising from extended tab screws. After this first screw is placed, the wires are bent laterally out of the way so that a second screw can be inserted through the same small incision. If a multilevel fusion is desired then the second screw can be configured to use flexible wires as guidance elements. Flexible wires are used for guidance elements until the last screw to be placed. This can allow the wires to bend out of the way of the final screw that is then placed with a removable or re-attachable tower. All MIS towers can be designed to be attached to pedicle screw heads prior to insertion of the screw into the vertebrate. However, with the use of wires as guidance elements, a tower can be attached or re-attached to the screw head through a percutaneous incision after the screw has already been inserted and implanted into the vertebrate.

In some embodiments, all screws on one side except the last screw can be configured to use wires as guidance elements while the last screw is configured to use a tower. The tower on the last screw can either be (1) a noncannulated tower that is attached to the screw head without a wire guidance element attached to the screw or (2) a cannulated tower that is guided over wire guidance elements after the wire is first attached to the screw. In some examples, if a tower that is not cannulated, embodiment (1), is used then once the tower is removed from that last screw, that tower can no longer re-attach to that screw because of the lack of wire guidance elements. This can be done, but this noncannulated tower on the last screw would have to stay on the screw until the rod is placed in all screw heads, and the locking cap is inserted into the last screw through the tower and final locked to the final locking torque. Then after final locking of the last screw the noncannulated tower can be removed. However once the noncannulated tower is removed, it would not be able to be re-attached through the same percutaneous incision.

In some embodiments, the last screw can be configured to use wire guidance elements and a cannulated tower utilizes these wire guidance elements to attach to the screw head (embodiment (2) above). This second embodiment allows the removal and then re-attachment of the tower for any of several reasons. There are many circumstances when the re-attachment of a tower may be necessary. These reasons include, for example: 1. if one of the screws need to be repositioned due to alignment issues (the screw heads cannot geometrically accept a rod because of malalignment). 2. If one of the screws need to be repositioned due to abnormal pedicle screw stimulation signifying that screw is too close to a nerve. 3. The rod was placed and decided after the tower was removed that the rod needs to be removed for rebending or replaced or trimmed due to wrong length. 4. The rod was placed and after the tower on the last screw was removed, one of the screws needed to be adjusted in depth or length, and thus the rod has to be removed and the screw needed to be adjusted. For these and other reasons, using a cannulated tower for the last screw is useful because the tower can be repeatedly re-attached to the screw as needed.

The key to successful placement of 2, 3, and even 4 screws for a 1, 2, or 3 level pedicle screw fusion, respectively, through a single incision on one side the size of the diameter of a single screw is that the screws use wire guidance elements and only one tower is to be inserted through the single incision at any one time. The rod can be placed without a tower, but rod placement may be facilitated by having one tower in the incision. After the rod is placed and the cap is placed through that one tower locking the rod in place, then the tower can be removed from that screw, and a cannulated tower can be placed through the wire guidance elements to dock onto another screw head. Once docked, the cap can be placed onto that screw and final locking can be performed for that screw and locking cap. For thin patients, locking caps can be placed without the tower as the wire guidance elements provide adequate tissue retraction. However in larger patients, the tower can be helpful in placement of the locking caps through a deep thickness of tissue.

An additional feature of the tower is that a docked tower can be used as the counter torque when final locking the cap to the final locking torque. Typically a counter torque has to be inserted over the screw head to prevent the screwhead from turning when a torque is applied to the locking cap. However a docked tower can be used as a counter torque so that a larger countertorque does not have to be inserted through the small incision for each screw in order to provide countertorque for the final locking of rod by the locking cap. The tower that is attached or re-attached in-situ (percutaneously) is guided to the screw by the wire guidance elements. Light mallet taps of the tower is usually enough to persuade the cannulated tower through tissue to attach or re-attach and dock onto the screwhead or extended tab. The tower then has threads inside the tower to allow for reduction of the rod into the seat of the screw for situations such as spondylolisthesis.

Attaching or re-attaching and docking the tower onto the screw has optionally a preferred embodiment of locking the tower onto the screwhead or extended tab after attaching or docking the tower onto the screw. Traditional towers that are not cannulated are always locked onto the screw by a locking mechanism. This locking mechanism typically consists of grooves or slots at the screw head or extended tab portions of the screw that allow locking of the tower by snapping locking ends into the holes or twisting portions of the tower that engage a locking portion of the tower to lock with the corresponding locking portion of the screw head. Other locking techniques include outer screw threads to screw the tower into position or ball and socket stops. These methods are commonly used to link pipes and tubes and joining parts in engineering. For the current preferred embodiment, cannulated towers are guided to the screw head or extended tab and locked onto the screw head through one of these locking mechanisms at the screw head.

Figure 6A:
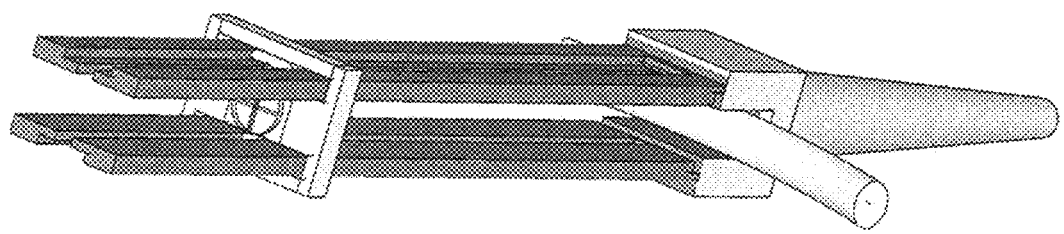
FIGS. 6A and 6B illustrate embodiments of locking mechanisms configured to removably engage the tower with the pedicle screw.
Figure 6B:
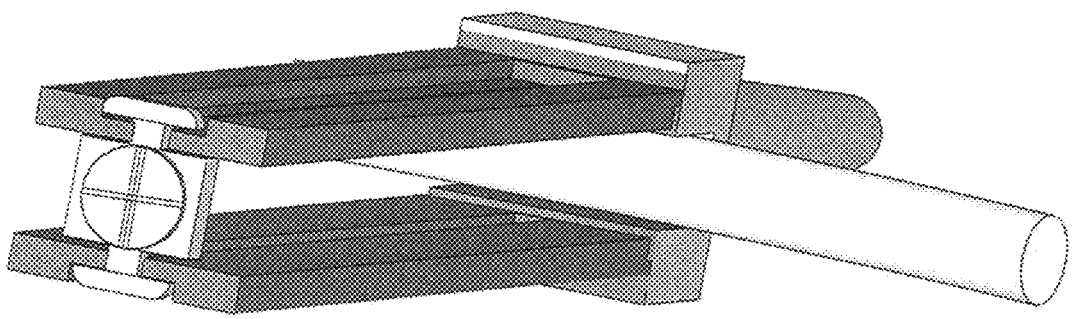
Figure 7B:
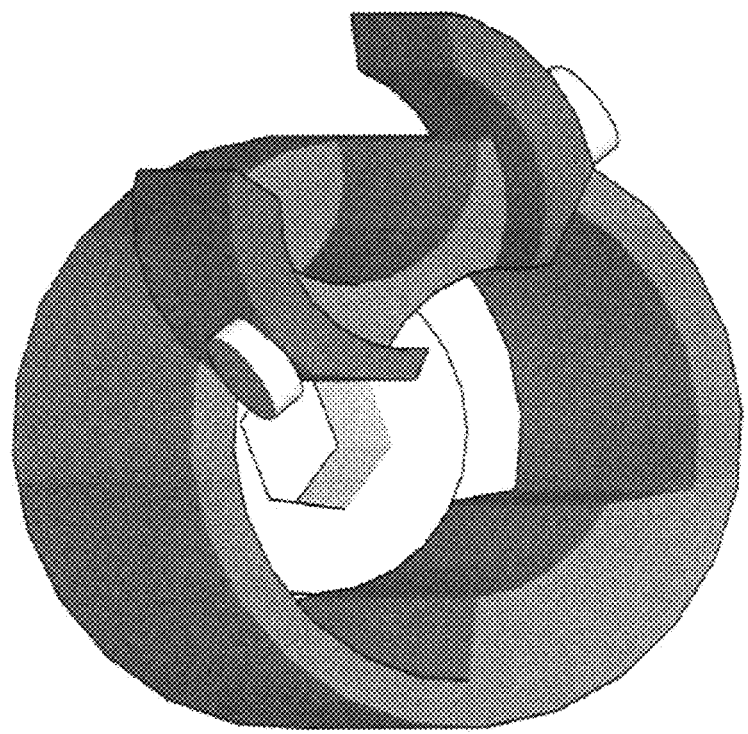
FIGS. 7A-7B illustrates an embodiment of locking mechanisms including a cap and rod holder configured to combine rod insertion with locking cap placement device.
Figure 7A:
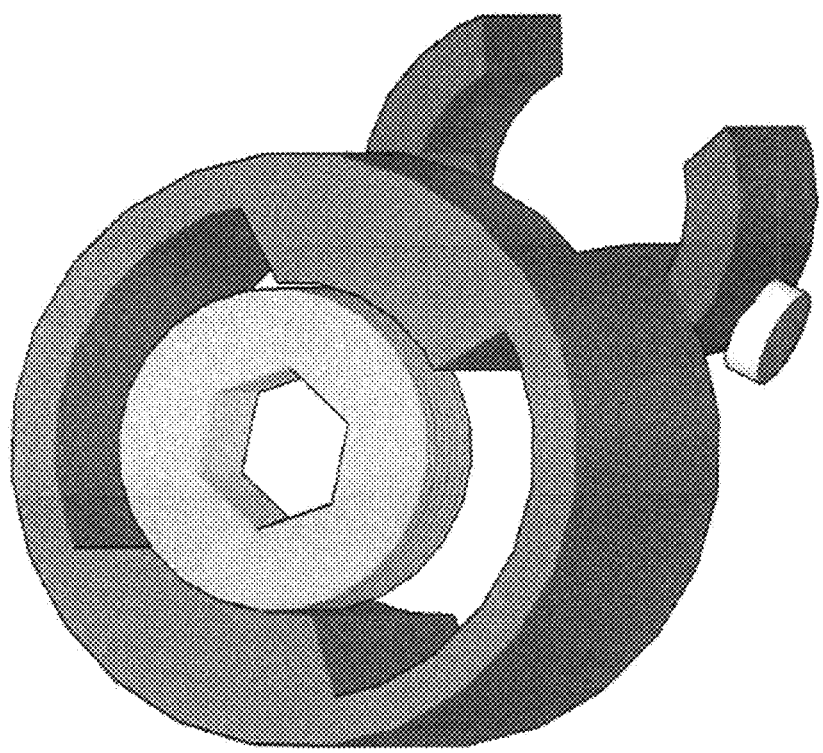
Figure 8D:
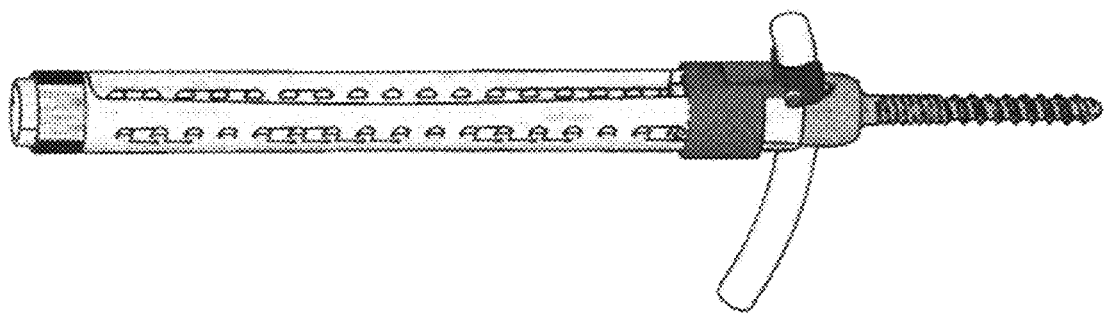
FIGS. 8A-8D illustrates the cap and rod holder of FIGS. 7A-7B engaging and locking a rod into a screw head of each of the pedicle screws.
Figure 8C:
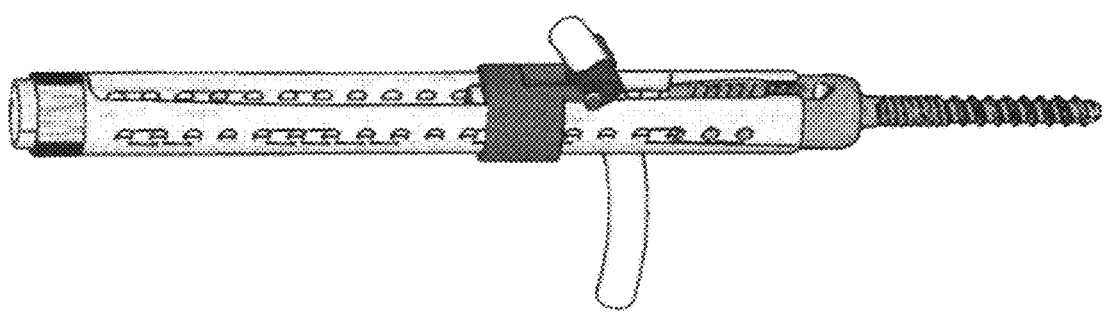
Figure 8B:
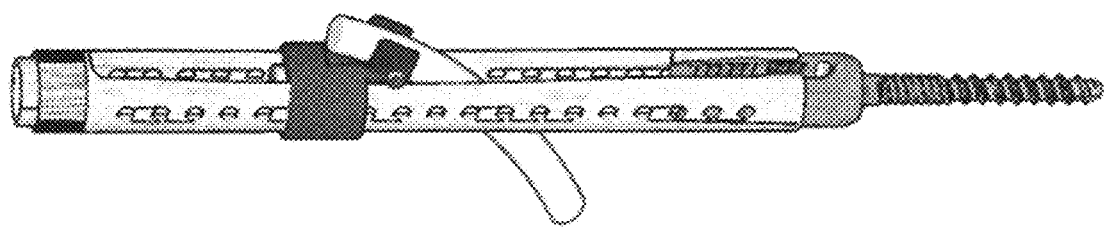
Figure 8A:
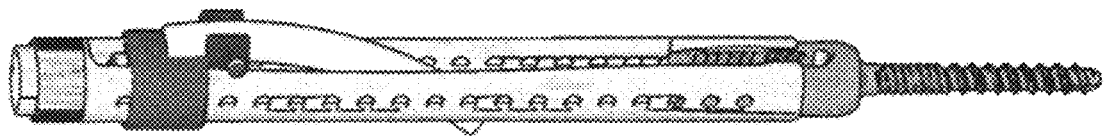

Alternatively a cannulated tower can also be locked onto the screw assembly by locking onto the wire guidance element. Typical embodiments of the locking mechanism include bending the wire at the top of the tower or attaching a clamp onto wire at the top of the wire where it exits the top of the tower. Simple wire clamping mechanisms are commonly seen in different clasps to hold earrings onto the ear lobes. Other wire clamping mechanisms somewhere in the cannulated tower wall where the wire guidance element passes include turning or sliding mechanisms that cause pressure clamping onto the wire. Towers do not need to be physically locked to the screw to provide countertorque capability, as traditional countertorques are not locked onto the screw heads. However locking the tower onto the screw assembly either at the screw head level or at the wire guidance element level does provide additional strength to the construct during rod reduction and final locking. Examples of locking mechanisms are illustrated in FIGS. 6A and 6B.

The sequence of screw insertion does not have to be sequential. For instance for a L4, L5, S1 screw fusion, the last screw does not have to be at the ends, i.e. either L4 or S1. In some embodiments, the last screw inserted may be the middle screw, L5.

Cannulated tower can be comprised of several pieces such as two blades and a connector between the two blades that turns the two blades into a functioning tower. This is used in the Viper system from Depuy as well as other systems. Thus a "tower" as described in the current disclosure can be actually formed from a number of parts including 2 cannulated walls or blades that each attaches to the wall of the extended tab of the screw as well as a joining piece that joins the two blades and locks the two blades into a fixed and rigid configuration, functionally equivalent to a rigid one piece tower.

In order to streamline the pedicle screw insertion process, consolidating the number of parts, components, instruments, and steps to insert the screw, insert the rod, lock the cap and all through the smallest incision possible with the least tissue disruption and damage possible is the key to successful lumbar fusion for the patient and surgeon. After the pedicle screw tract is found by either anatomical landmarks, fluoroscopy, or stereotactic navigation, guidewires are inserted into the pedicle screw tracts. Then the tracts are tapped to the correct size for each pedicle screw size. Then pedicle insertion is relatively straight forward over the guidewire using cannulated pedicle screws. The next difficult step is inserting the rod and locking the rod into the seat of the pedicle screws. Insertion of the rod has been one of the defining and differentiating characteristics of some pedicle screw systems. For instance the Medtronic Sextant MIS screw system uses a pedulum mechanism to swing the rod through a separate incision into the seat of each screw head.

As disclosed in the present application, the goal is to minimize incision size and the number of incisions to lessen tissue damage and foster faster recovery. The Medtronic Sextant MIS system requires a separate incision for each screw plus another incision for the rod insertion. In contrast the current disclosure allows 1, 2, and 3 level lumbar pedicle screw fusions to be done through a single incision the size of the width of a single pedicle screw. Wiltse approach will need one incision on each side while cortical bone trajectory would need only a single midline incision. In order to accomplish this, we had discussed above that the pedicle screws will use wire guidance elements to sequentially allow cannulated towers to dock onto each screw in succession in order to lock the locking caps into each screw, one at a time. This techniques essentially allows each screw and tower to "share" the single small incision by sequentially accessing the respective pedicle screws one at a time through the same incision.

After the screws have been placed, the rod is inserted into the seat of all the screws on that side and then locking caps are inserted one at a time into each screw and locked to the final tightening torque. In order to facilitate this final process of rod insertion and cap placement device, a streamlined and combined rod insertion and cap placement device has been developed. An example of the combined rod insertion and cap placement device is illustrated in FIGS. 7A-7B and 8A-8D. In addition the same mechanism serves part of the function of the counter torque to squeeze the screw head walls in order to not splay during final tightening of the locking screw to the final torque. This way a counter torque is not needed and the tower can be used as a counter torque during the final tightening of the locking screw.

In order to combine the rod insertion and cap insertion, a combined component of the tower is introduced that slides up and down with channels built in to allow the walls of the tower to pass through the rod and cap holder/introducer. The rod and cap holder slides up and down the tower with the blades and walls of the tower passing though the holder and the holder maintaining arms that reach around each wall or blade so that the anti-splay function can be performed by preventing the walls from splaying during the final tightening process.

The cap and rod holder has a central channel for the cap to pass and actually having threads for the cap to screw into and through. When the cap and rod holder is deployed all the way to the bottom of the tower after the tower is docked to the screw, then the central channel allows the cap to be screwed through the holder and into the threads of the walls or extended tabs of the screw smoothly without any interruption or chance of cross threading.

The cap and rod holder also has an extension off to one side that has two finger extensions that hold a rod. These finger extensions have a turning mechanism that allows the fingers and the rod to turn from a vertical orientation while first inserting through the skin incision and then turning to a perpendicular orientation when the rod is finally seated down into the seats of the screw heads. Thus as the cap and rod holder is lowered through the incision down the tower and towards the seat of the head of the screw, the rod is turned by the turning mechanism and articulation of the fingers with cap and rod holder. As the rod is turned and sits down into the seat of the screws, the rod and cap holder is deployed and lowered completely and docks with the top of the screw head or extended tabs. Then the cap is screwed down in the normal fashion through the threads within the cap holder and continuing into the threads within the screw walls/extended tabs. The cap then pushes on the rod that is already in the seat of the screw head and the cap is final tightened while holding the tower outside the skin without the need for the insertion of an additional counter torque.

The cap and rod holder is designed such that once the cap is screwed completely to the final tightening torque, the cap pushes the rod away from the cap and rod holder and to the bottom of the seat of the screw. This action by the cap pushes the rod out of the fingers of the rod holder and disengages the rod from the rod holder and the fingers. Then the cap and rod holder is now freed from both the cap and the rod and can be removed with the tower in one step.

After the first tower is removed after the rod is inserted and cap is final tightened, the other screws can be locked by inserting cannulated towers over wire guidance elements of the other screws in a sequential manner. The towers and inserted, caps are inserted and final tightened and then the tower is removed. This sequence is repeated for each screw until all the screws are locked.

In between each cap tightening, a compression mechanism is activated to squeeze that screw being locked and the previous screw that had already been locked. The compression mechanism can be a traditional instrument designed to squeeze the head of the two corresponding screws or else could be external compression. External compression can be performed by an operating bed capable of flexion and extension of the body during surgery. External compression is actuated by extending the bed causing extension to the body of the patient and thus compression of the posterior aspect of the spine, i.e. the pedicle screws.

FIGS. 9A-9E illustrate an embodiment of a system for stabilizing spinal vertebrae 400 including a hybrid combination of guidance elements. In some embodiments, the system for stabilizing spinal vertebrae 400 can include a plurality of screws 410(a, b). FIGS. 9A-9E illustrate a first screw 410a and a second screw 410b, but the system for stabilizing spinal vertebrae 400 can include any number of screws. In some embodiments, the screws 410a, 410b can include a bone engaging shaft 412a, 412b. In some examples, the bone engaging shaft 412a, 412b can be threaded. As illustrated in FIGS. 4C-4E, the bone engaging shaft 412a and the bone engaging shaft 412b can be inserted into the vertebrae and secure each of the screws 410a, 410b.

In some embodiments, the screw 410a, 410b can include a screw head 414a, 414b located on a proximal end of the bone engaging shaft 412a, 412b. In some examples, each of the screw heads 414a, 414b include an insert 416a, 416b that can be configured to receive rod 420 and a locking assembly (discussed in FIGS. 10A-10Z below). In some embodiments, the screw heads 414a, 414b can be configured to be relatively moveable to different angles relative to the bone engaging shaft 412a, 412b.

Figure 9B:
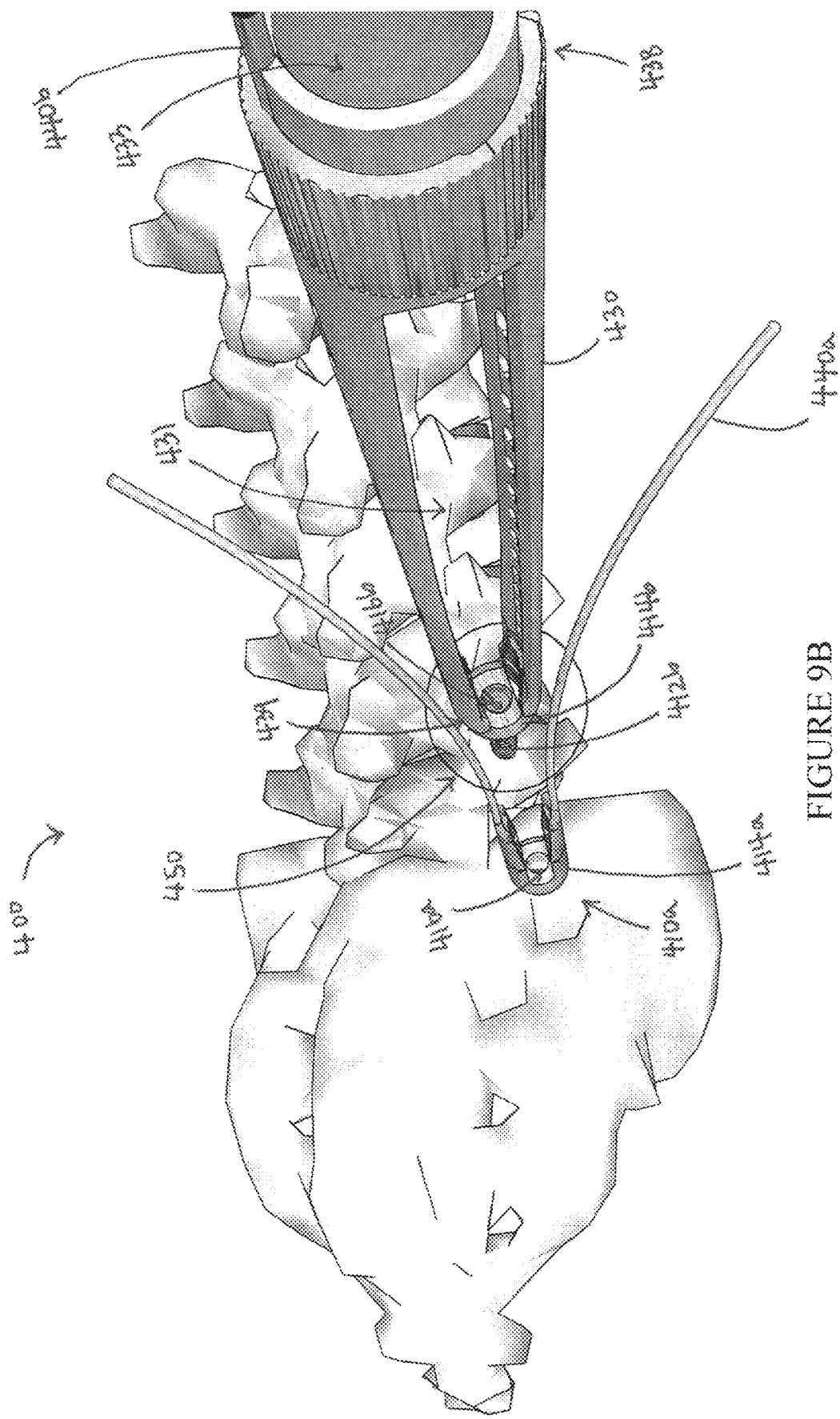
Figure 9D:
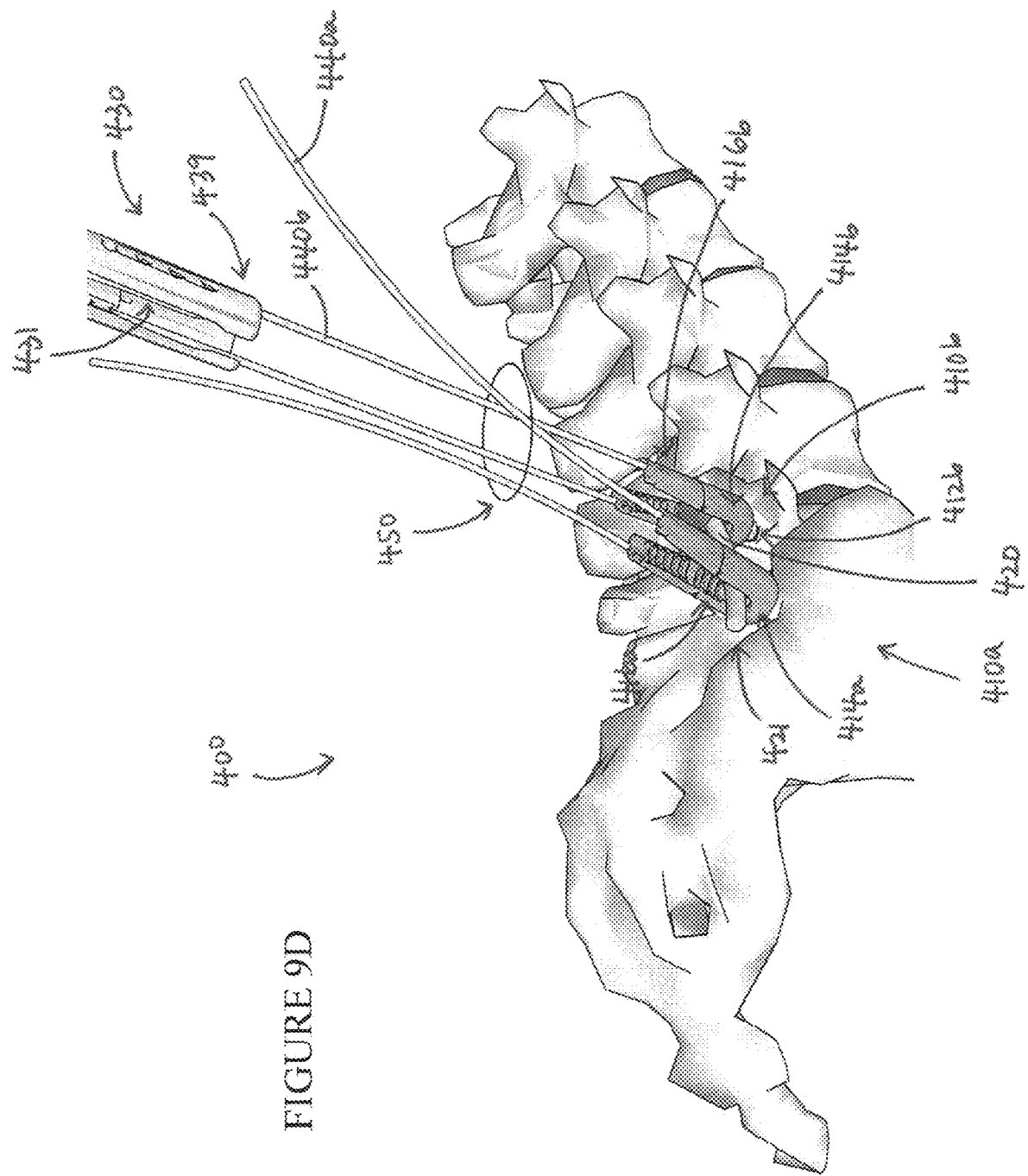
Figure 9E:
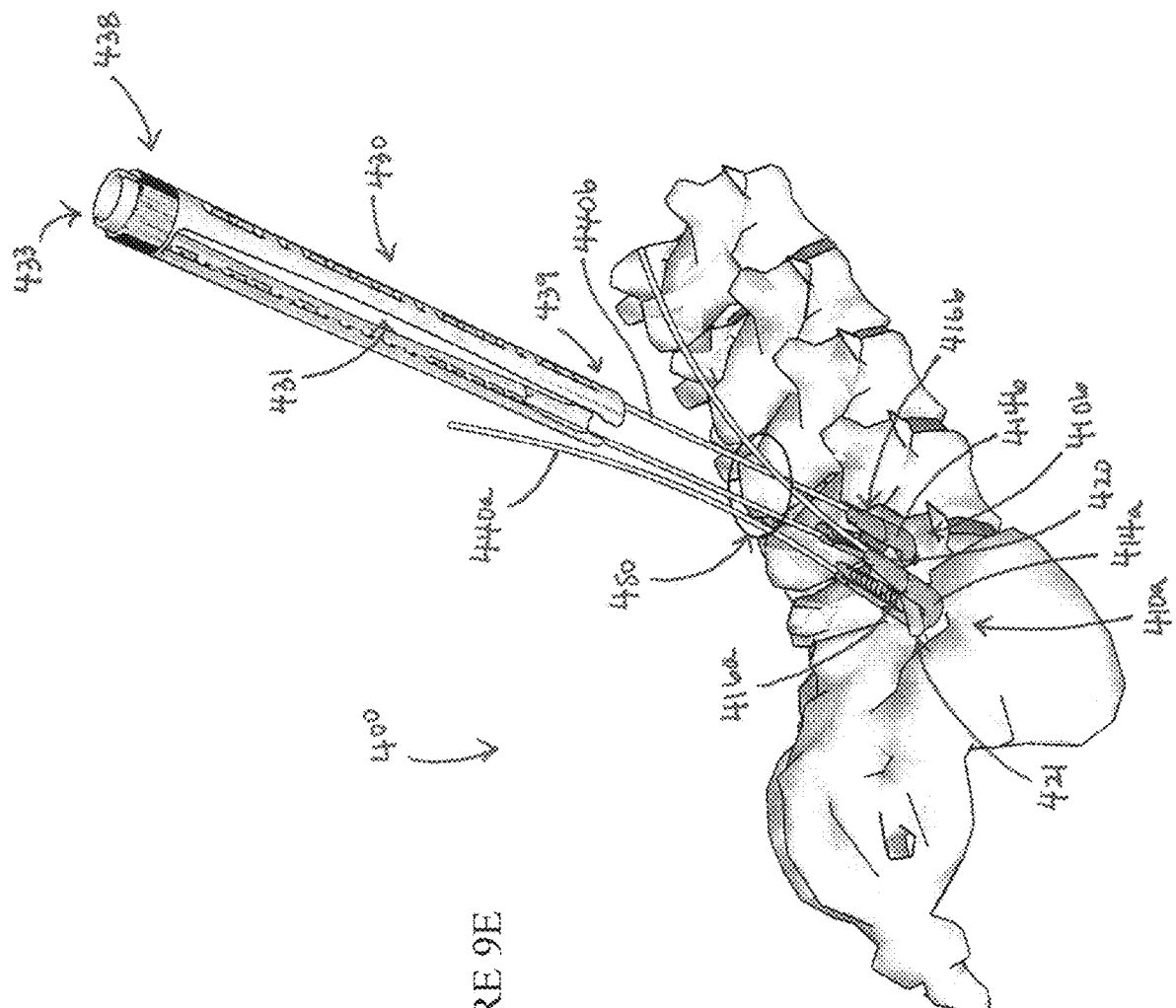

In some embodiments, the system for stabilizing spinal vertebrae 400 can include a plurality of guiding elements that are attached to a proximal end of the screw heads 414a, 414b. In some examples, the plurality of guiding elements are wires 440a, 440b. As illustrated in FIG. 9A, the screw head 414a of the screw 410a can include a plurality of wires 440a that extend from the proximal end of the screw head 414a. In some examples, the plurality of wires 440a are removably attached to the screw head 414a. In some embodiments, the wires 440a are screwed into the screw head 414a. In some examples, the wires 440a can be snapped off the screw head 414a. In some embodiments, one wire of the plurality of wires 440a is located on opposite sides of the screw head 414a such that a wire is located on either side of the insert 416a. As will be discussed in more detail below, the pair of wires 440a can securely trap the rod 420 over the bone engaging shaft 412a within the insert 416a of the screw head 414a. As discussed above, in some examples, the wires 440a extend from a distal end that is attached to the screw head 414a and out through an incision 450 on the proximal end. This can help a surgeon or other user conducting the surgery to locate and access the inserted screw 410a without being able to see it. FIG. 9D illustrate the screw 410b, like the screw 410a, that includes a pair of wires 440b that is attached to a proximal end of the screw head 414b and extends through the incision 450 at a distal end. As will be discussed in more detail below, wires 440b can help a surgeon or other user conducting the surgery to locate and access the inserted screw 410b without visually locating it.

In some embodiments, the system for stabilizing spinal vertebrae 400 can include a tower 430. As illustrated in FIGS. 9A-9E, the tower 430 can include a window 431 that extends from a distal end 439 of the tower 430 to the proximal end 438 of the tower 430. In some examples, the window 431 separates the two curved arms of the tower 430 such that a rod 420 or other structure (e.g., locking assembly, tools, etc.) can be guided to the plurality of screws in the vertebrae. In some embodiments, the proximal end 438 of the tower 430 includes a circular opening 433 that facilitates the delivery of a structure (e.g., a locking assembly, rod, etc.) to the implanted screws. As shown in FIG. 9C, in some examples, the distal end 439 of the tower 430 is disposed about a proximal end of the screw head 414b. This can allow the tower 430 to be stabilized and retained on the screw 410b such that a surgeon or other user can access the retained screw. As is also illustrated in FIG. 9C, in some embodiments the proximal end 438 of the tower 430 is configured to extend out of the incision 250. Like the plurality of wires 440a, 440b discussed above, the distal end 439 of the tower 430 can allow a surgeon or other user to access the screw below the incision 250 without visually locating it. In some examples, as will be discussed in more detail below, the tower 430 are configured to be disposed about the wires (e.g., the wires 440a and wires 440b) such that the tower 430 can be guided to the screw head (e.g., screw head 414a and screw head 414b) of the implanted screws. By allowing the tower 430 to be slid down the wires attached to the proximal end of the screw heads such that the distal end 439 of the tower 430 is retained about the proximal end of the screw head, the tower 430 can be easily removed and re-attached to each of the implanted screws. This can provide easy accessibility to perform the method of stabilizing the vertebrae and to potentially repair any components of the system as for reasons described in more detail above.

Figure 10G:
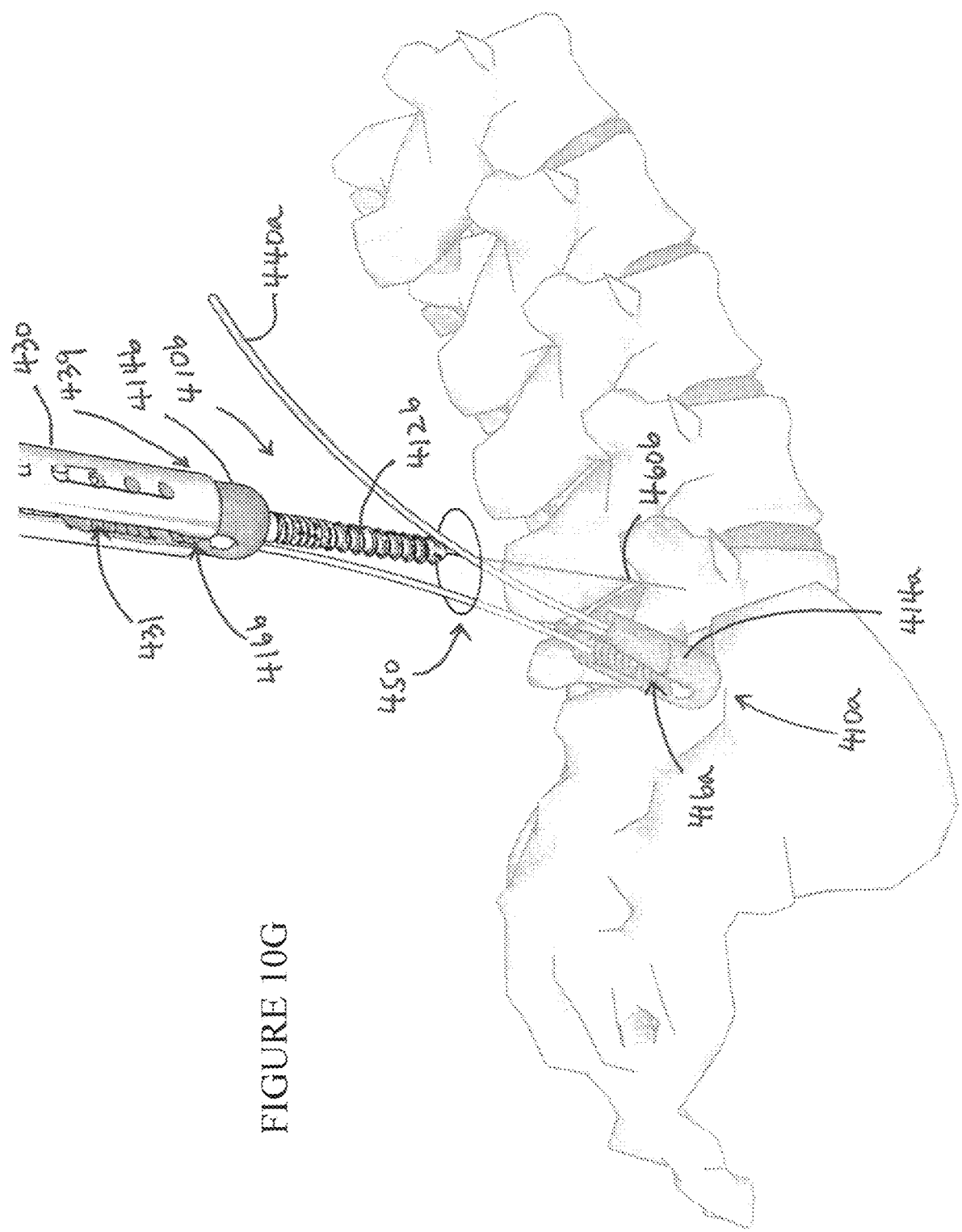
FIGS. 10A-10Z illustrate an embodiment of a method for stabilizing spinal vertebrae comprising pedicle screw including hybrid guidance elements.
Figure 10H:
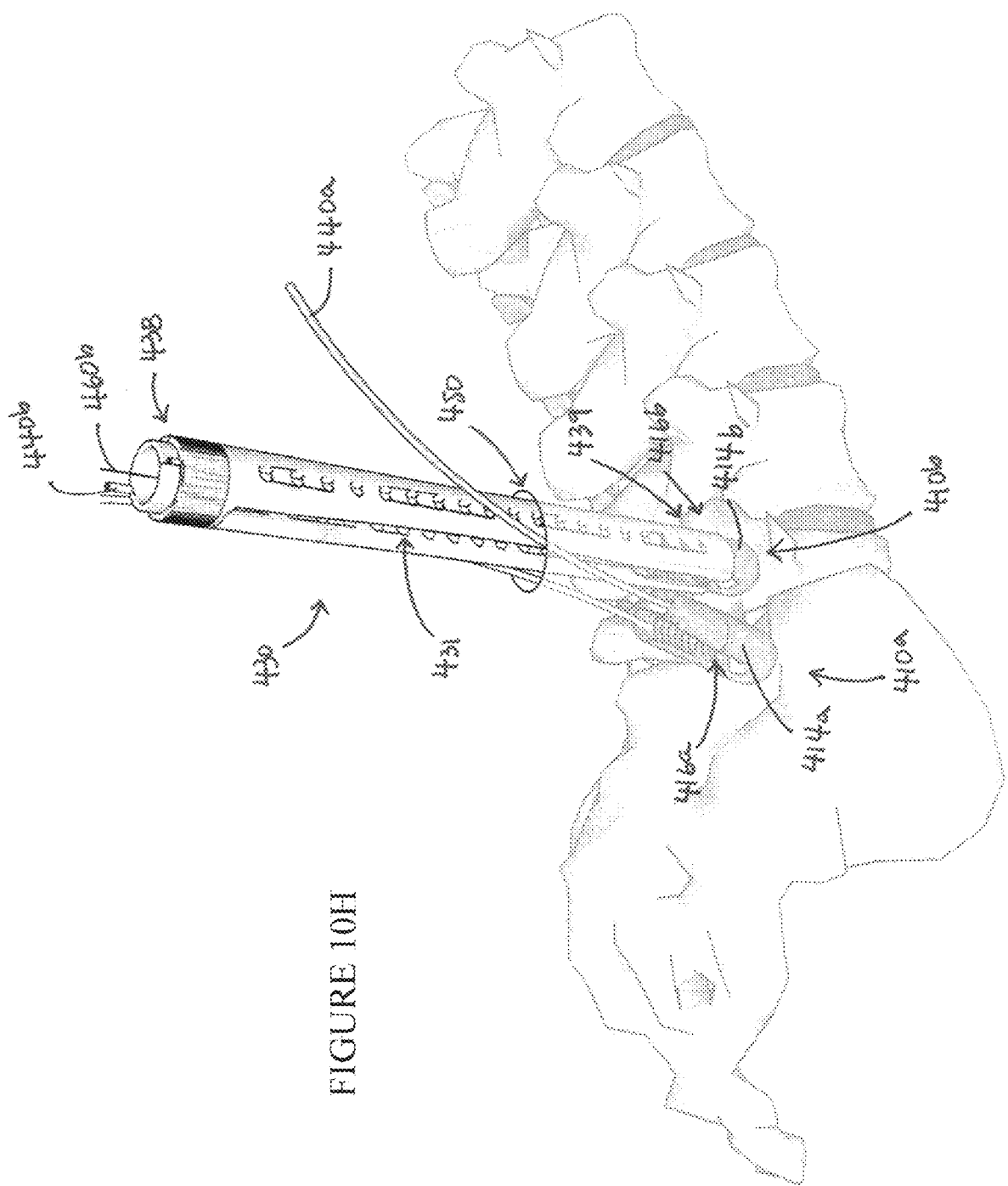
Figure 101:
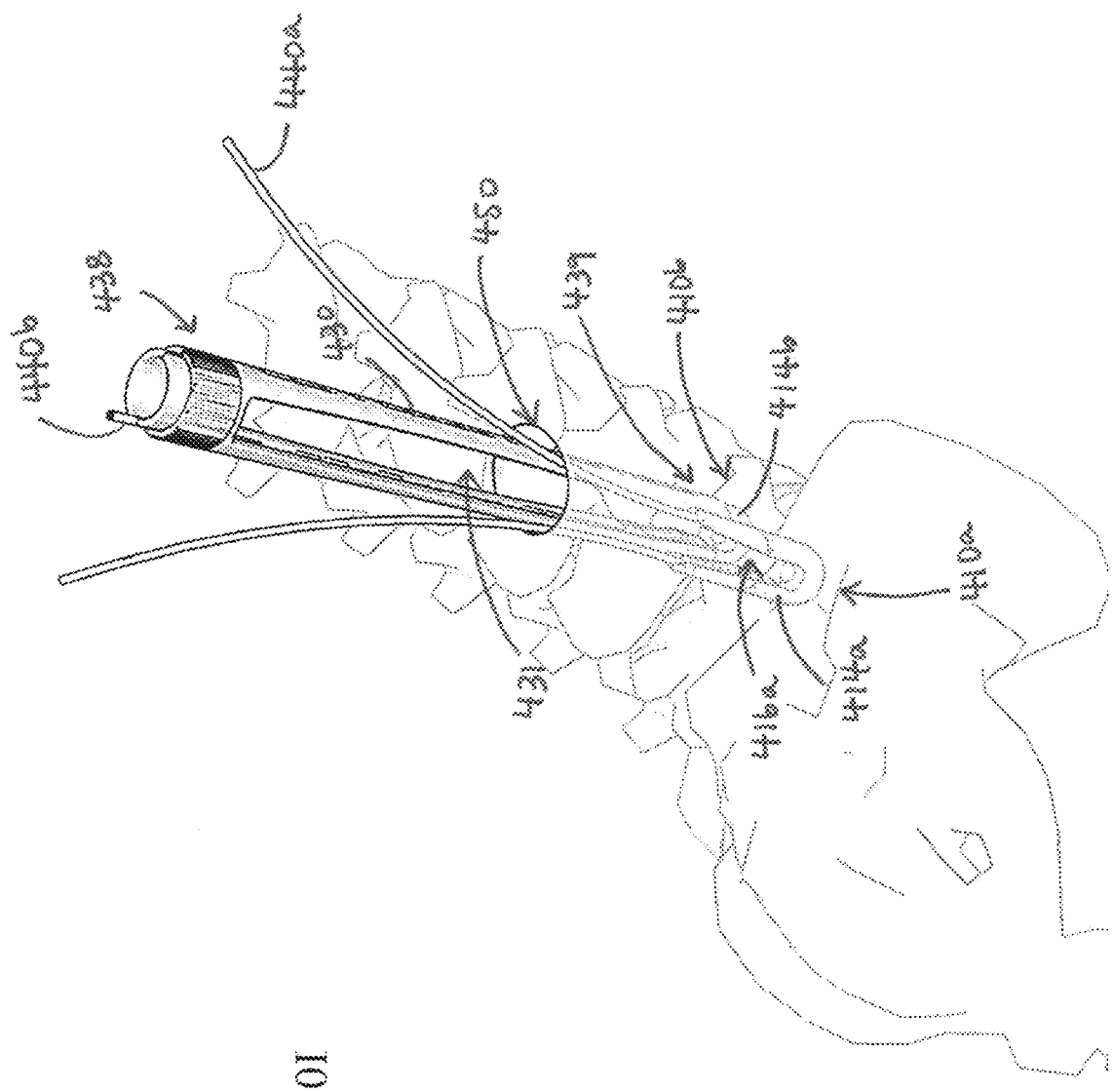
Figure 10J:
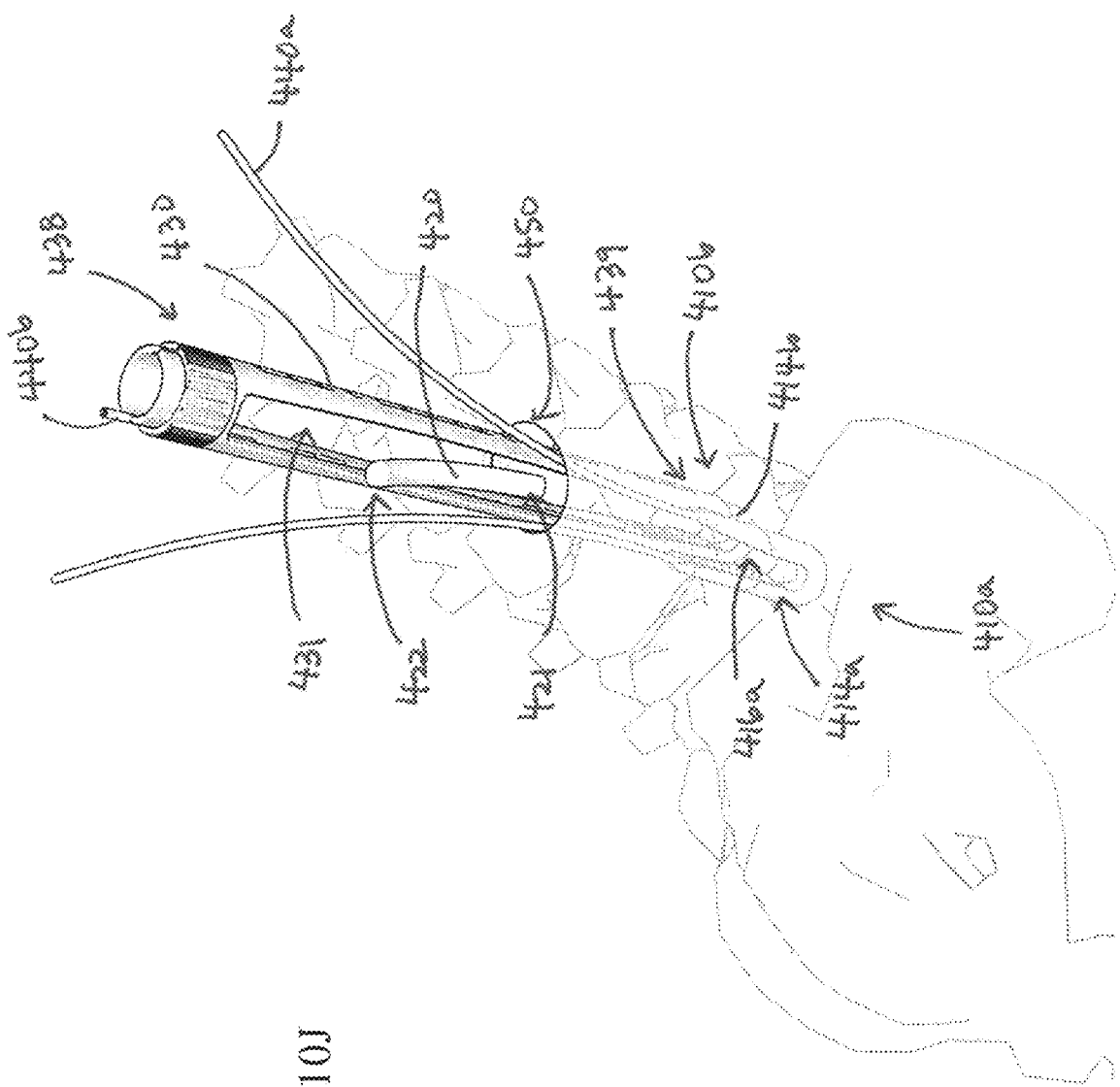
Figure 10K:
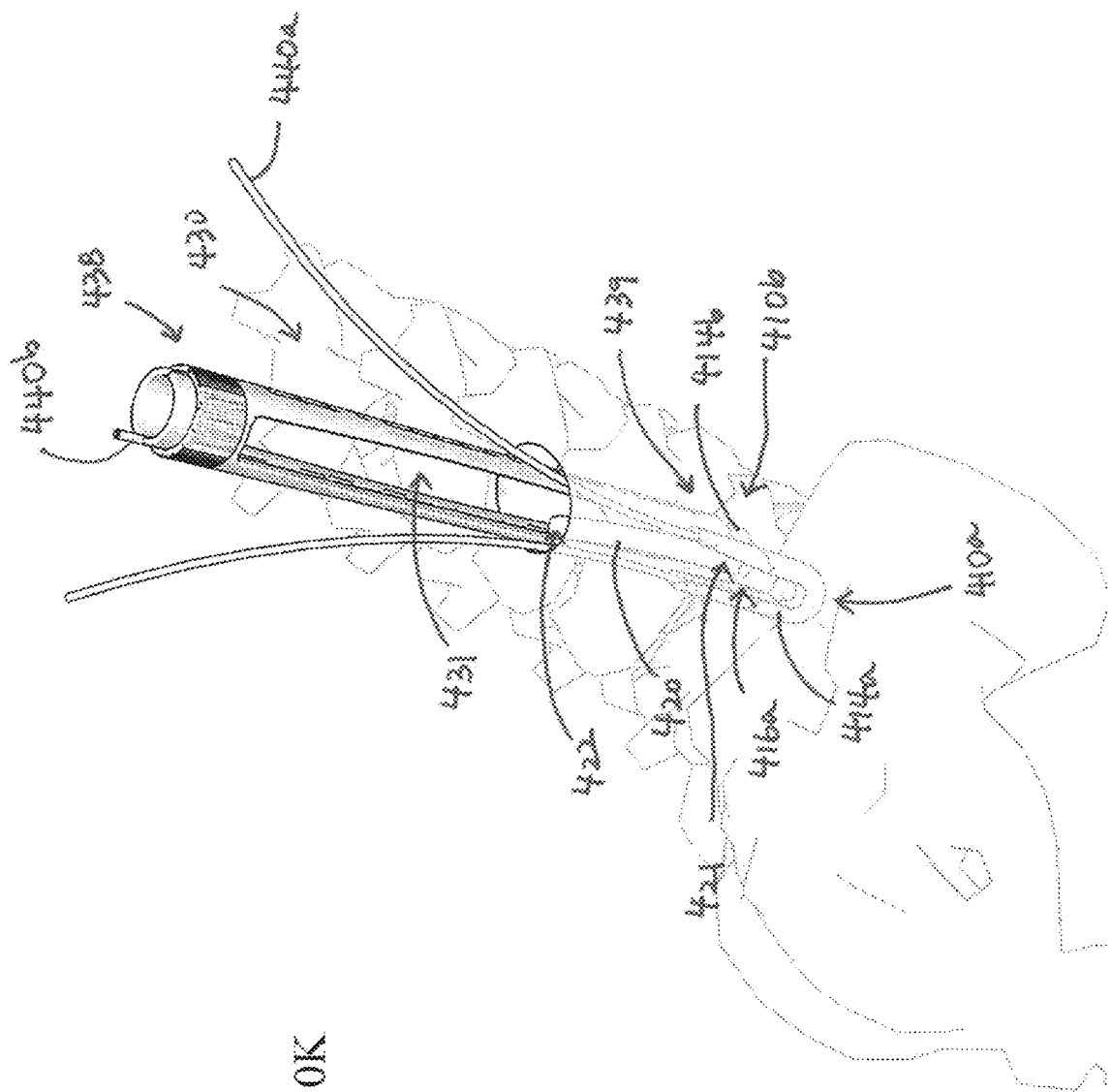
Figure 10L:
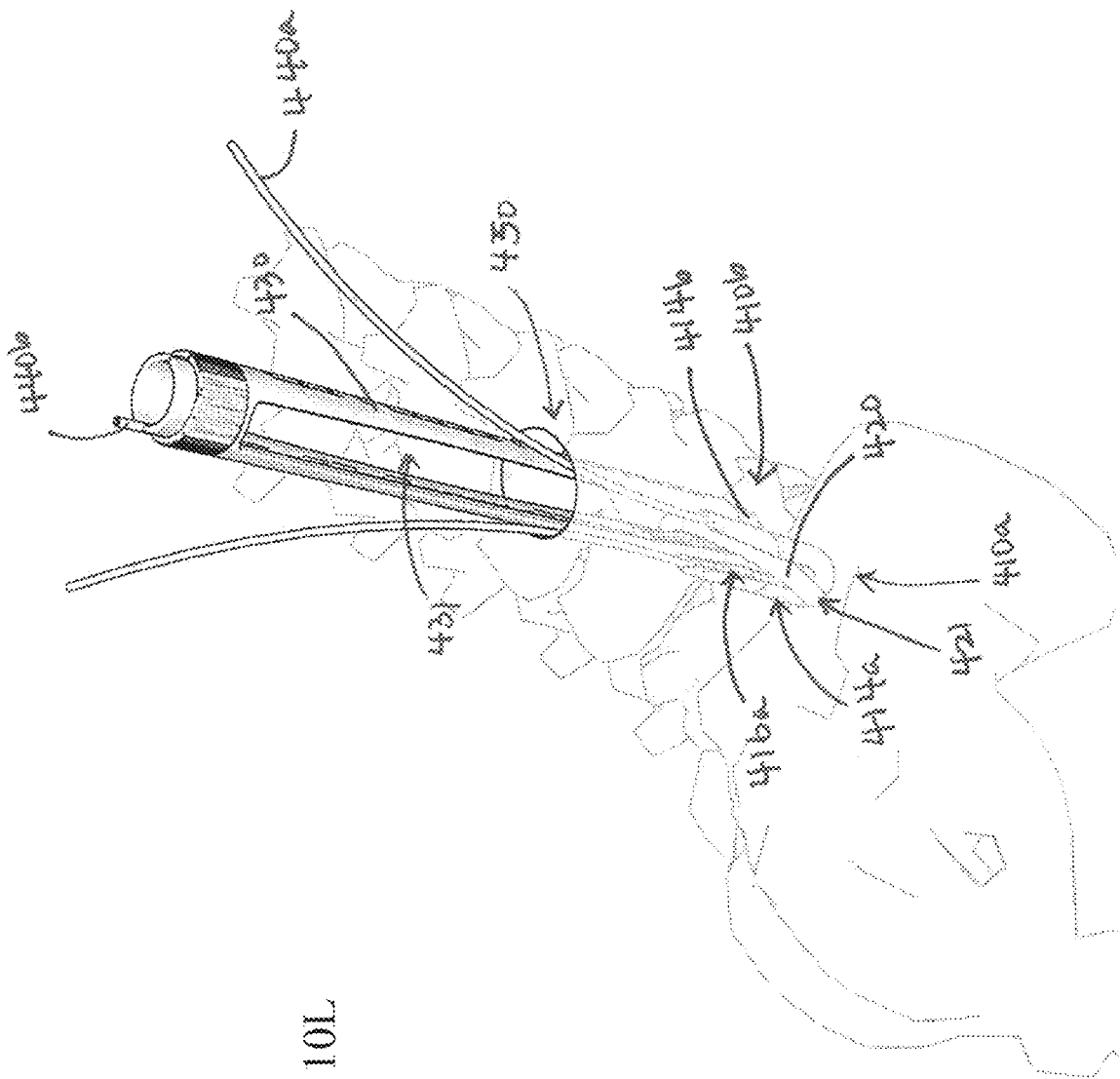
Figure 10M:
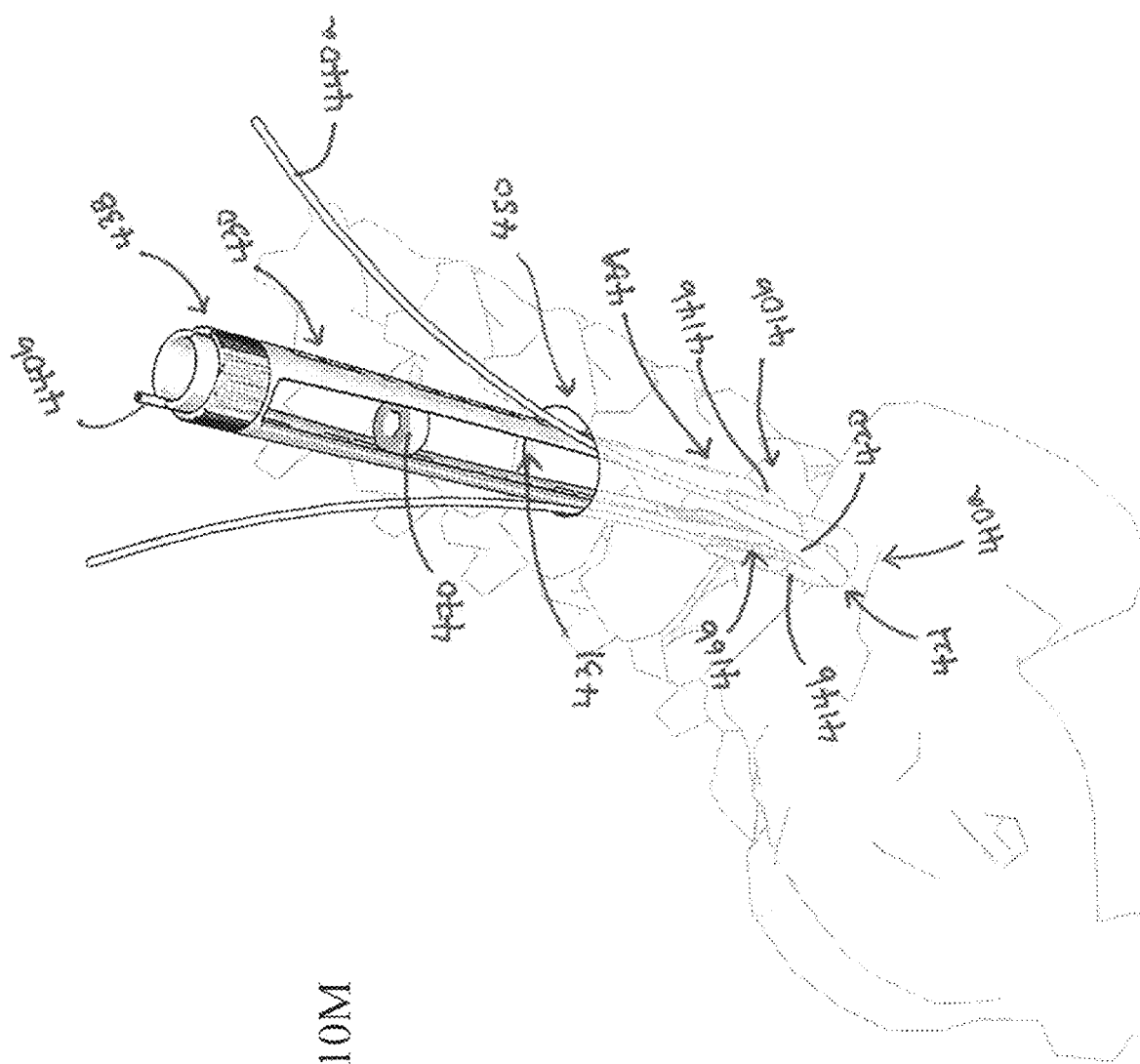
Figure 10N:
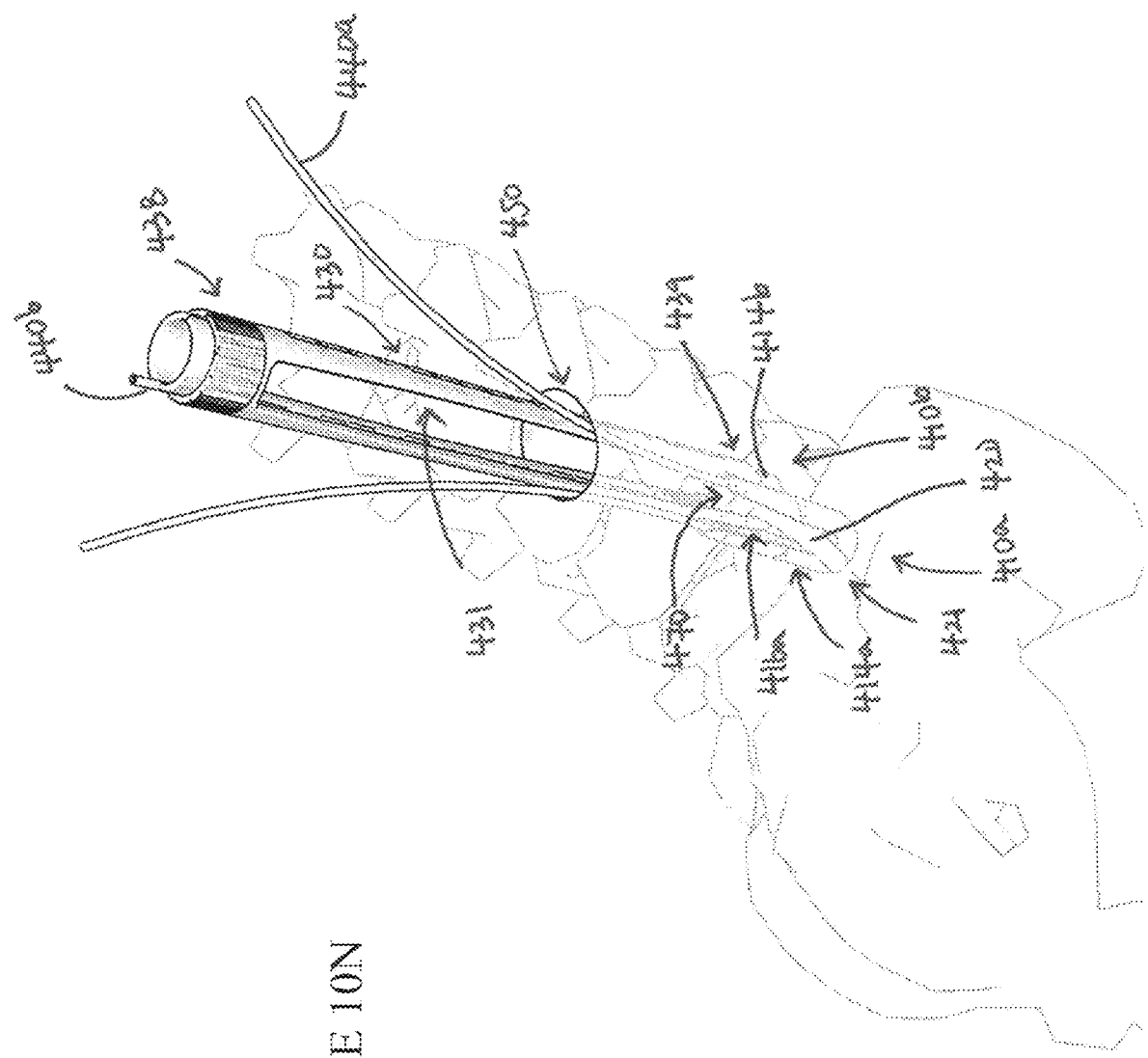
Figure 100:
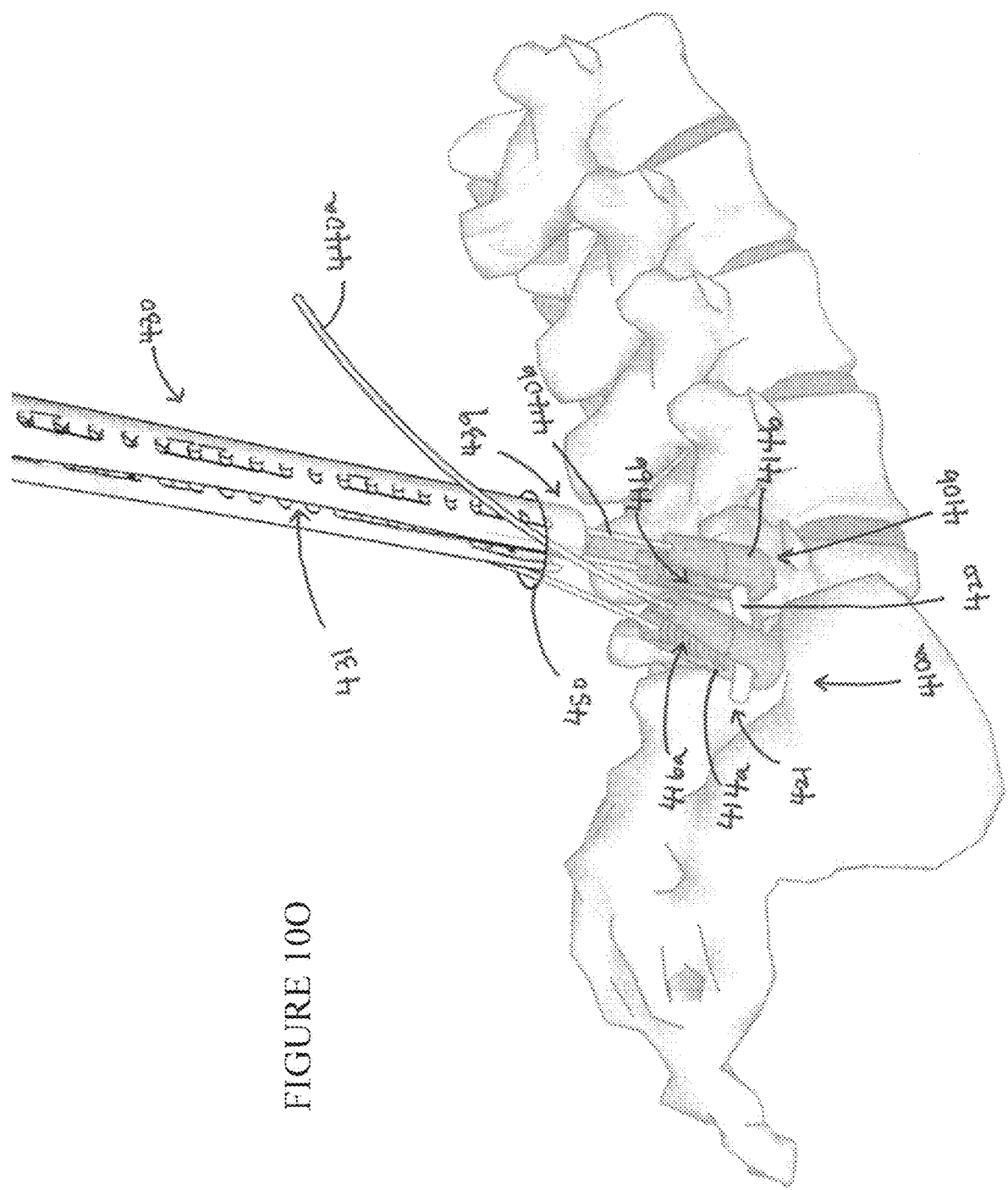
Figure 10P:
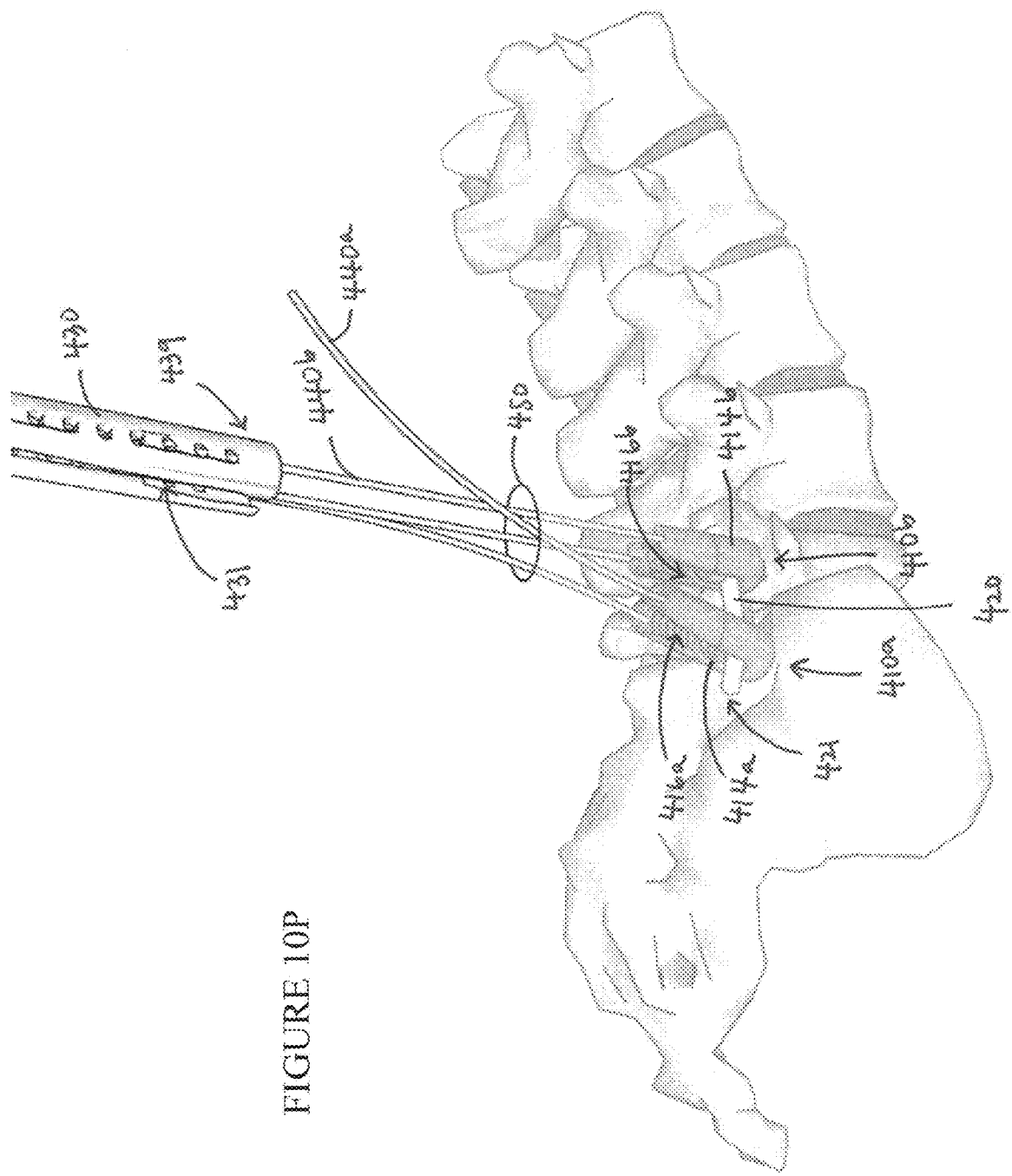
Figure 10Q:
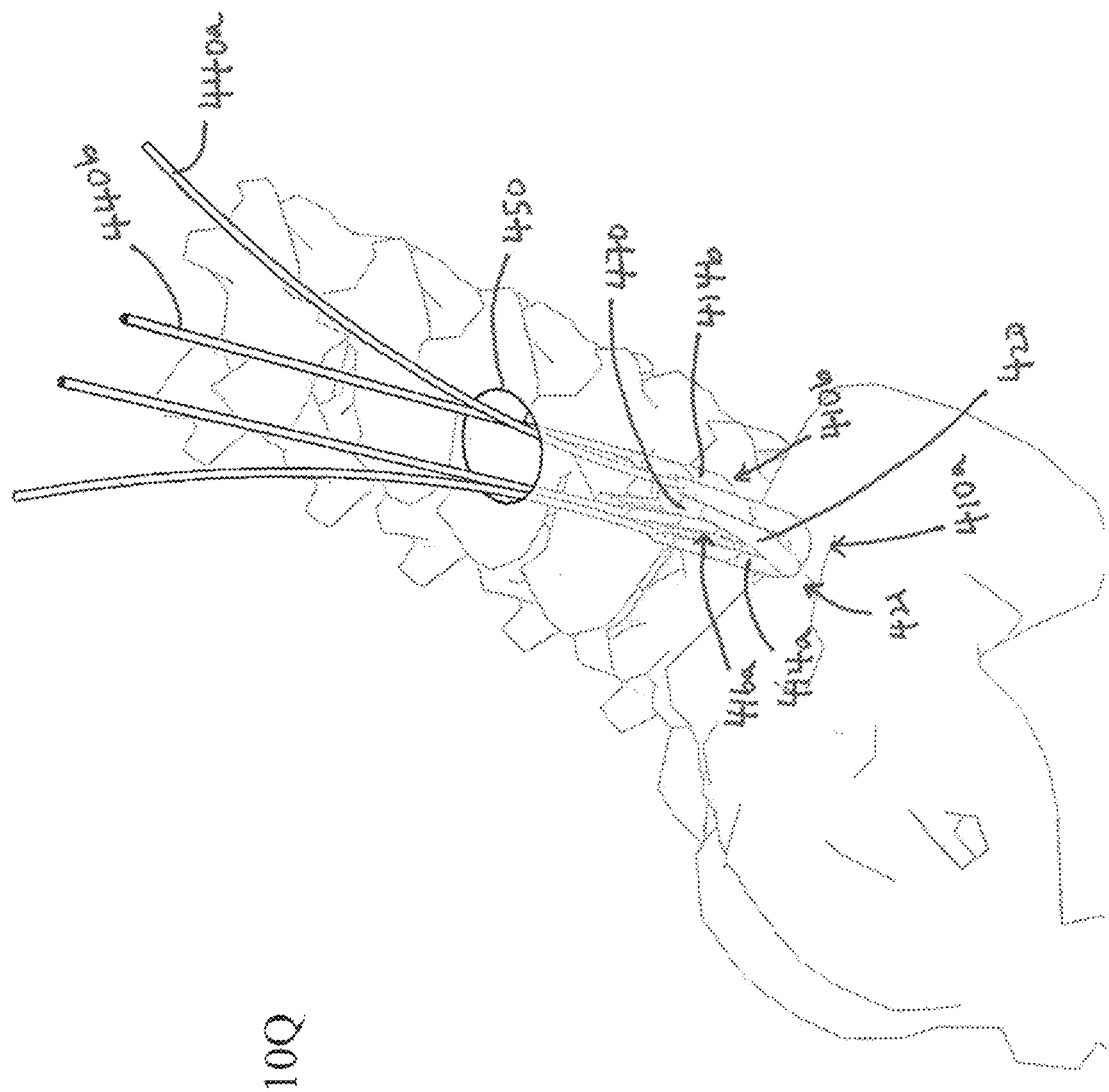
Figure 10R:
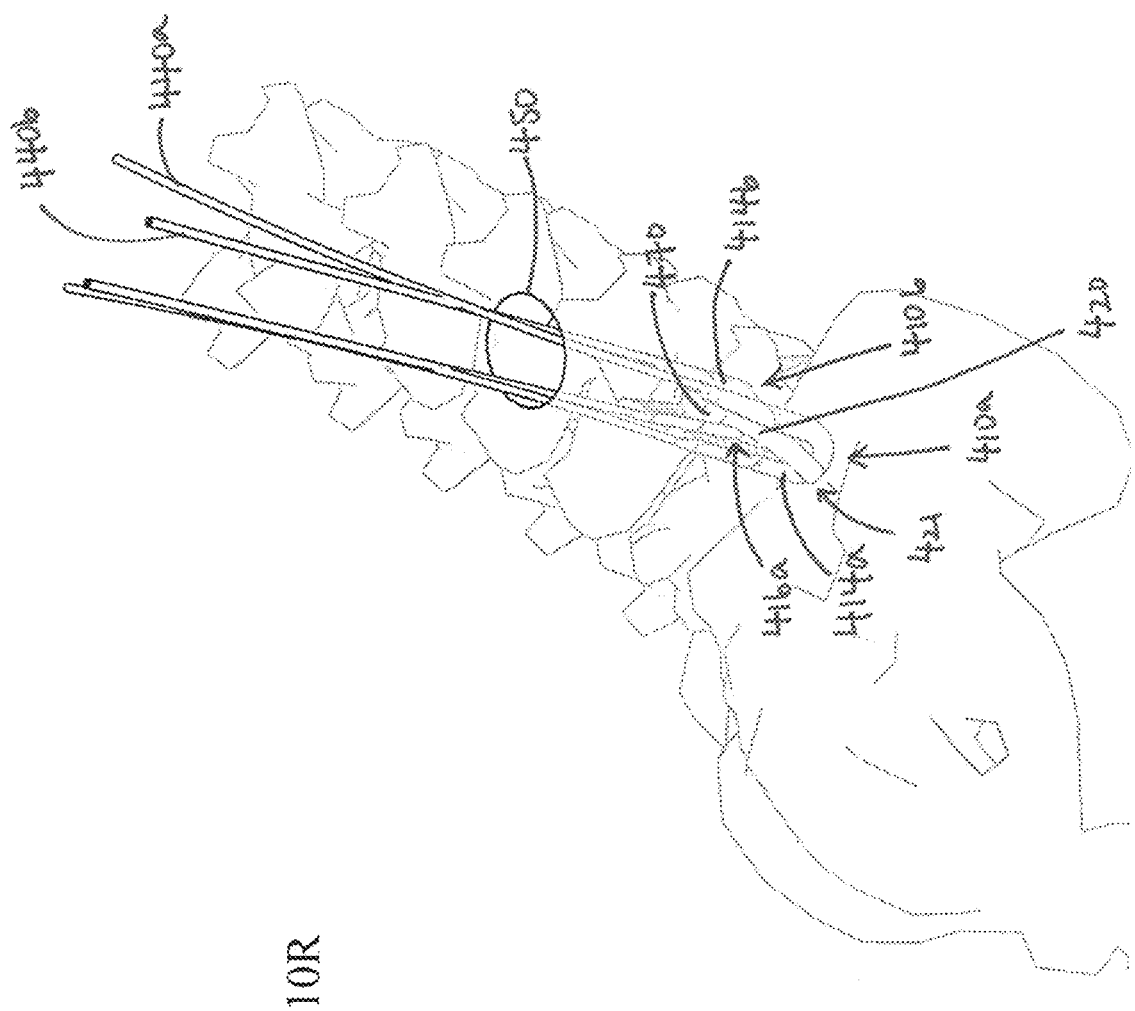
Figure 10S:
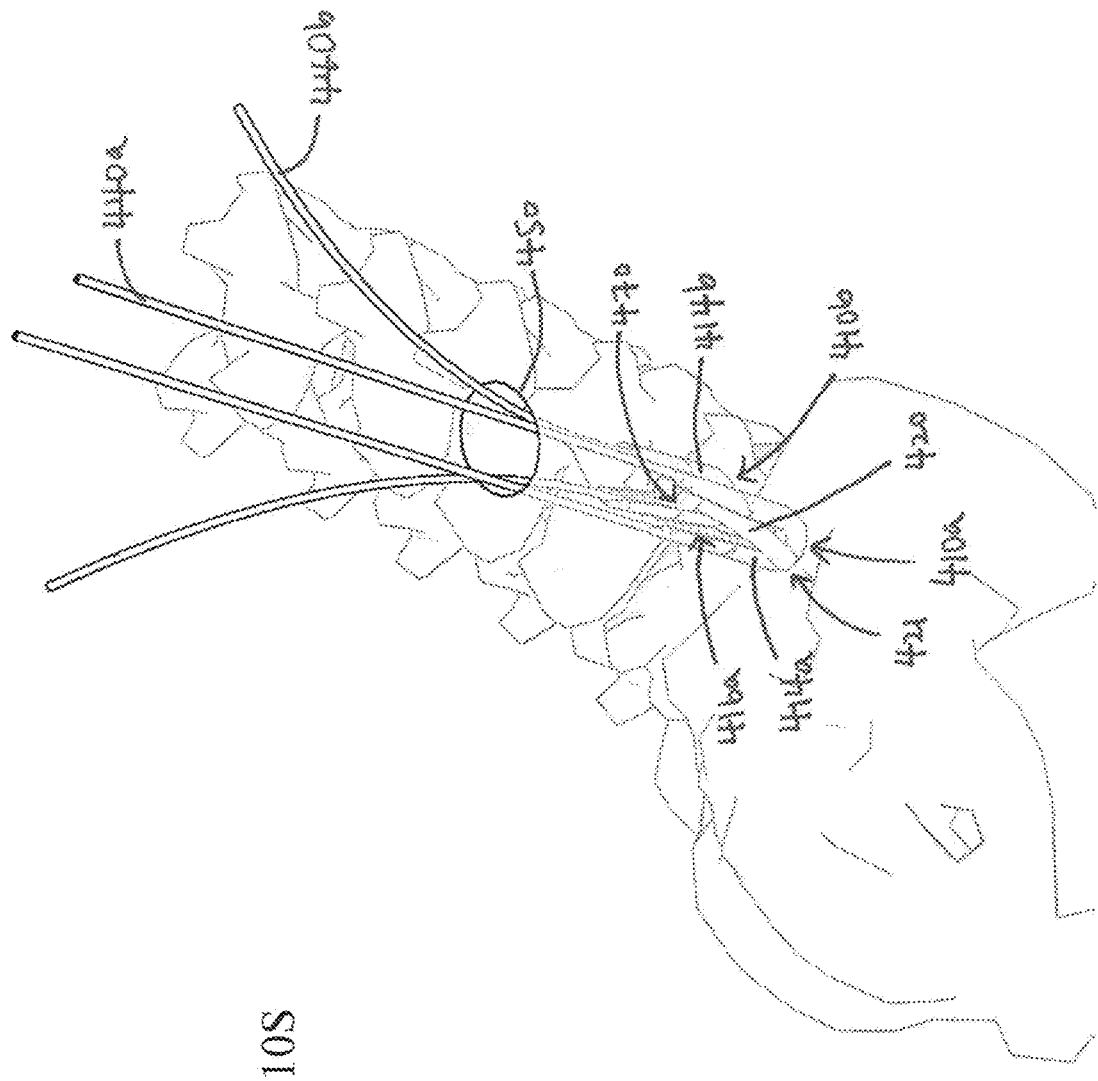
Figure 10T:
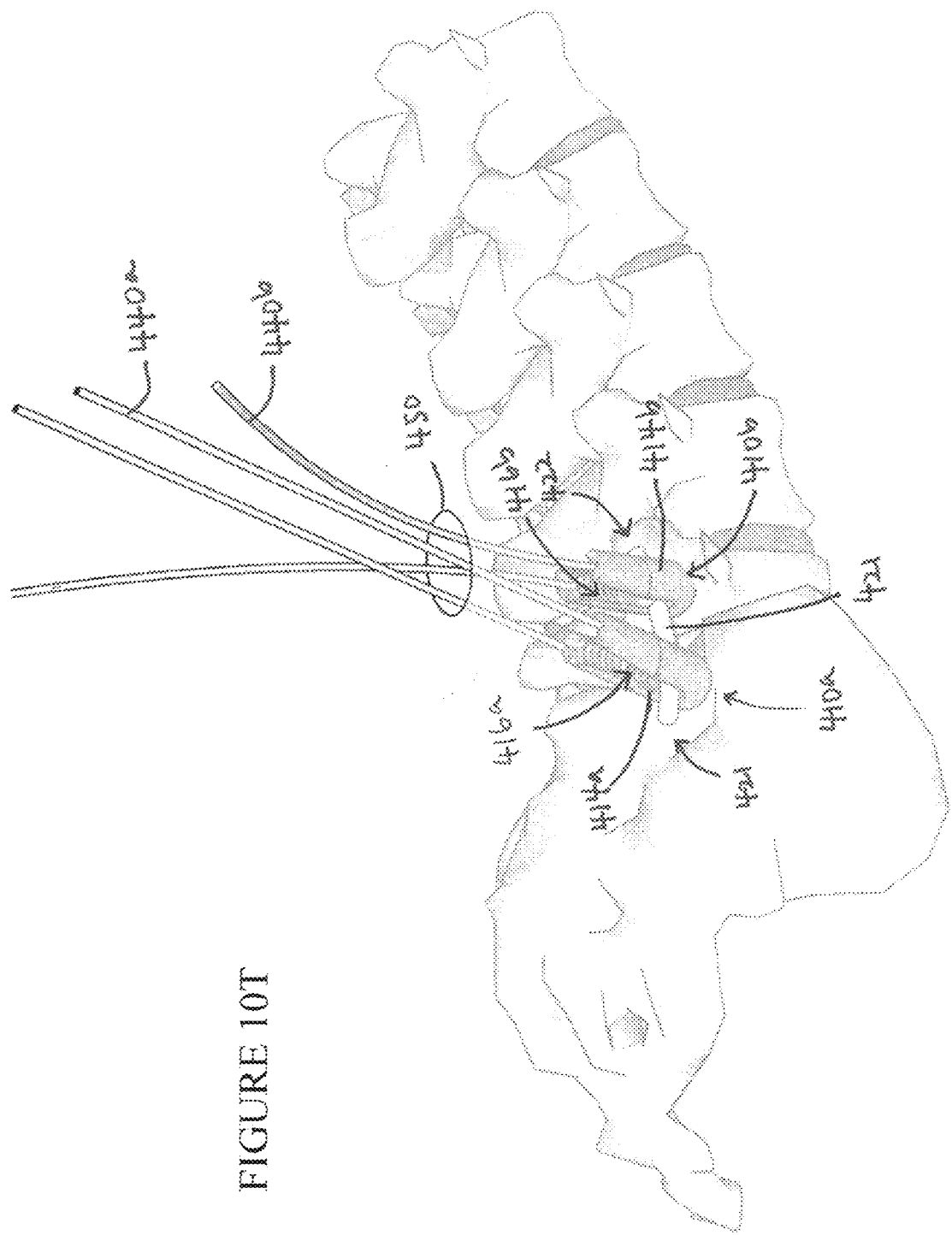
Figure 10U:
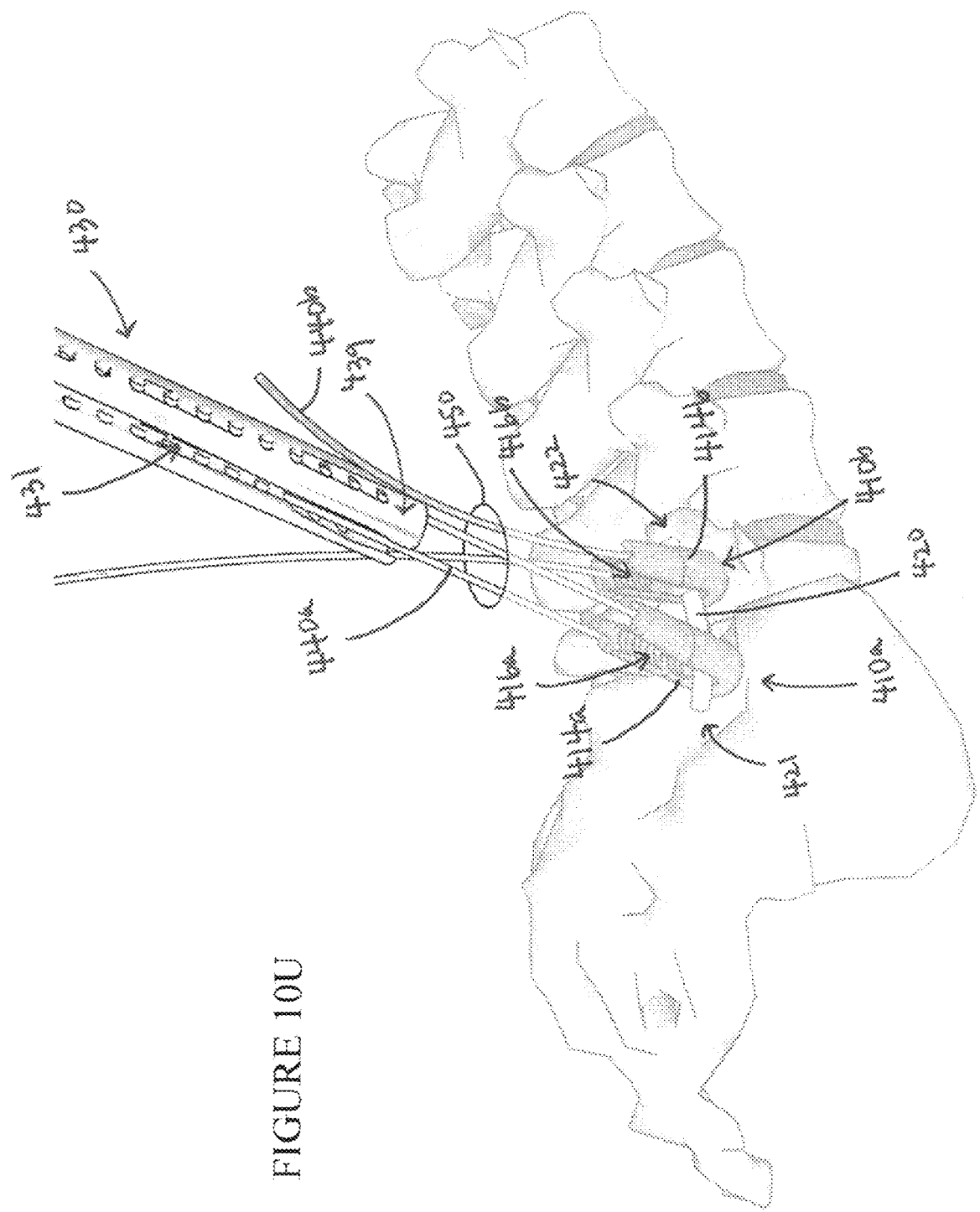
Figure 10V:
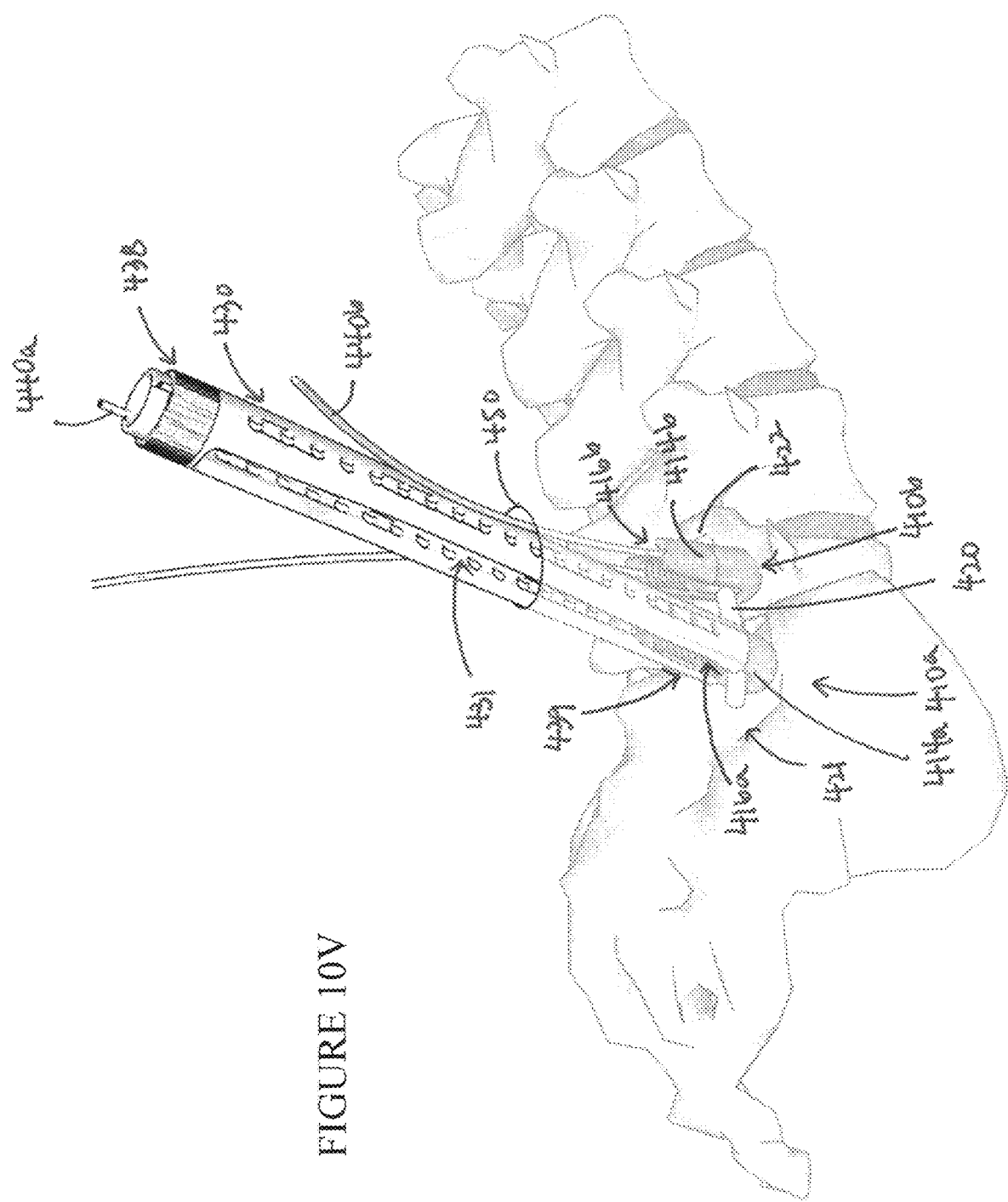
Figure 10W:
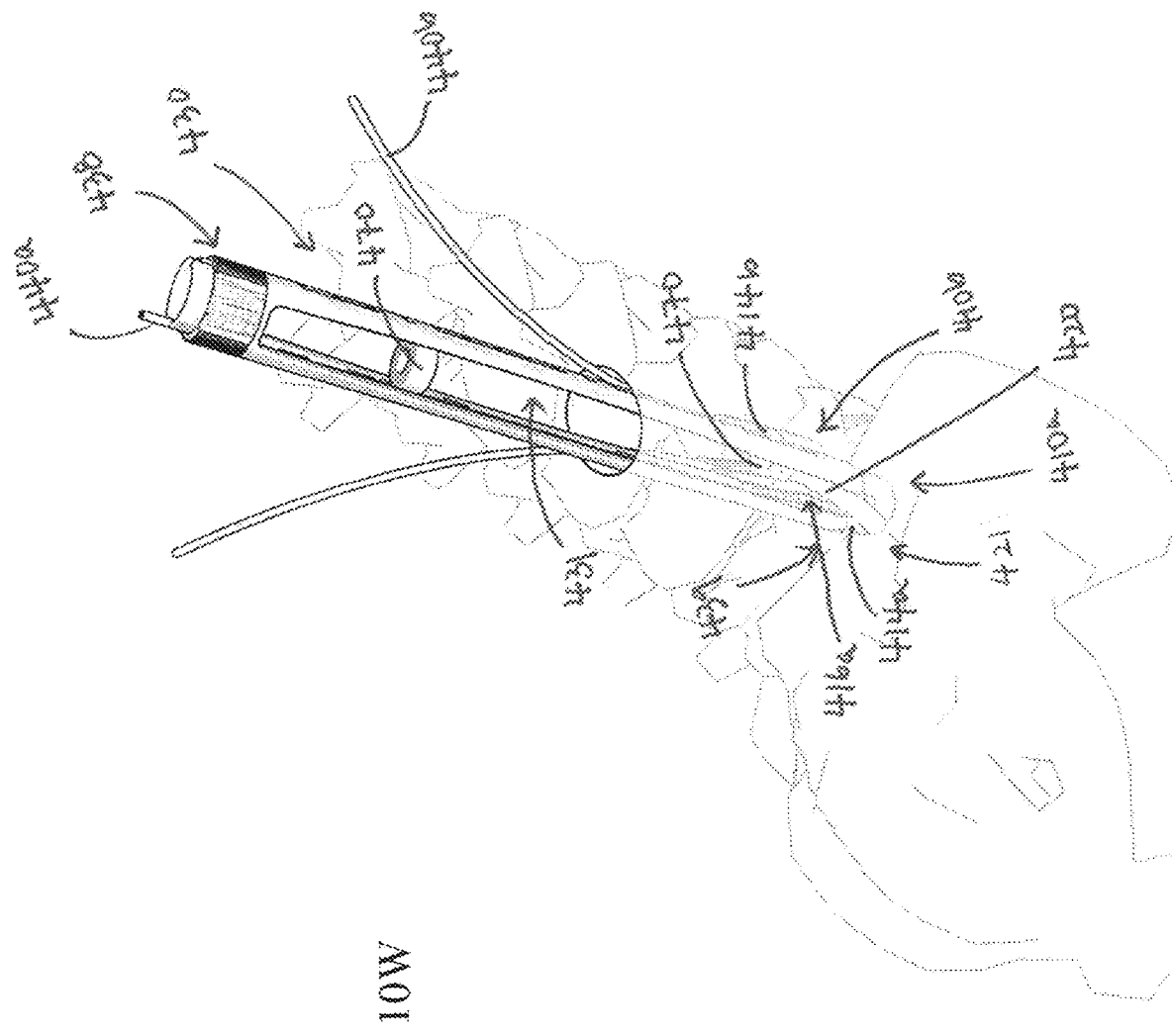
Figure 10X:
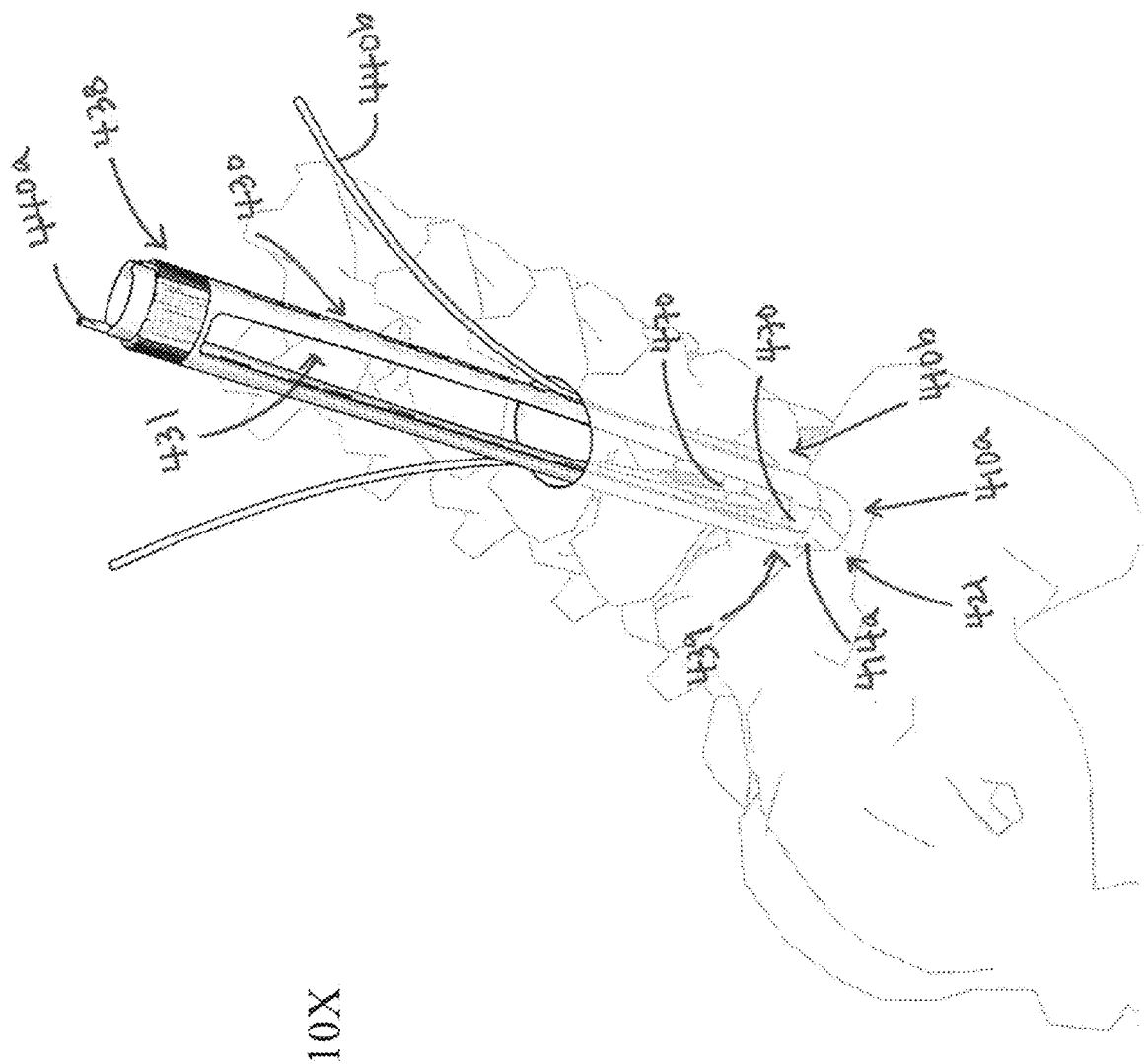
Figure 10Y:
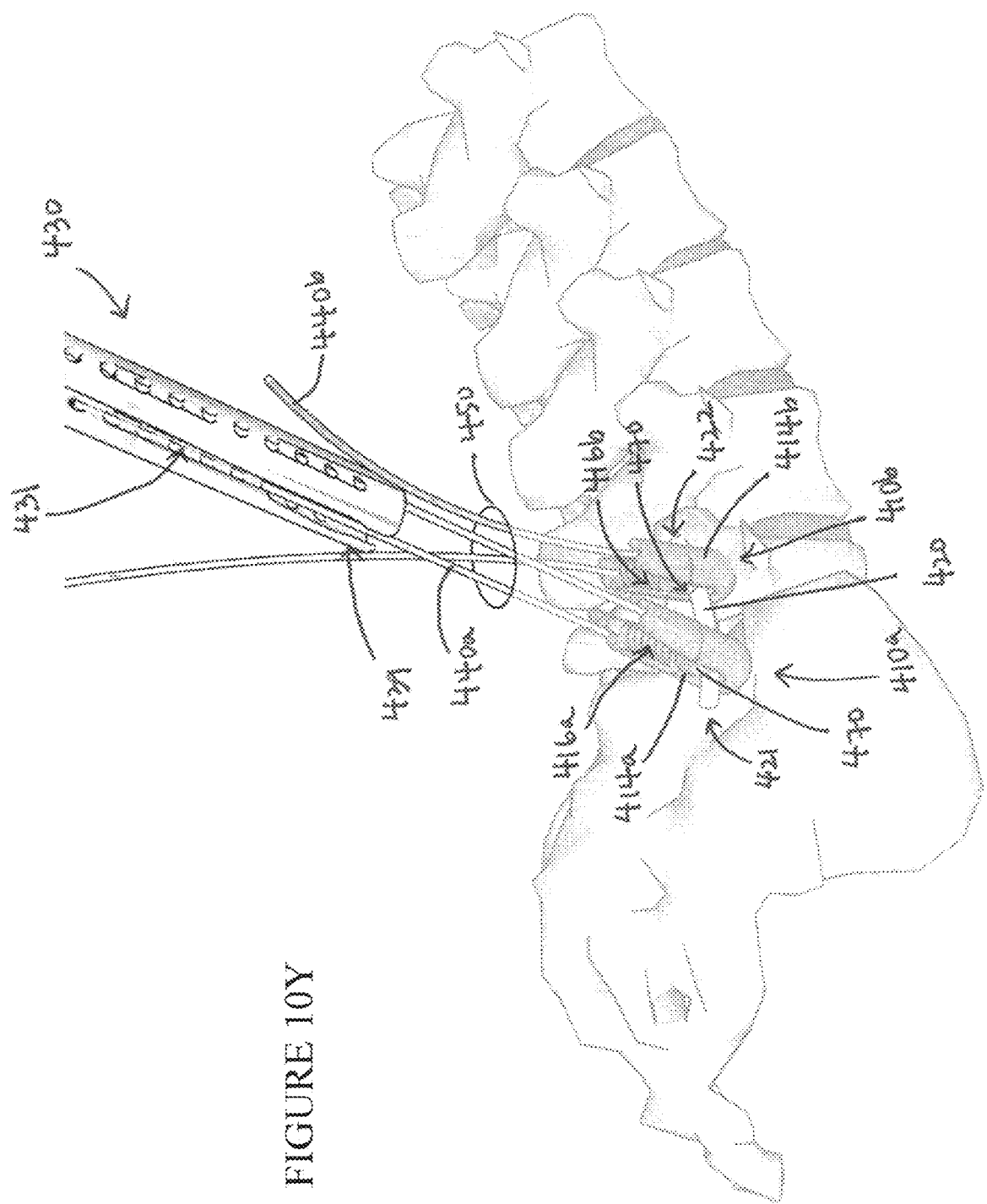
Figure 10Z:
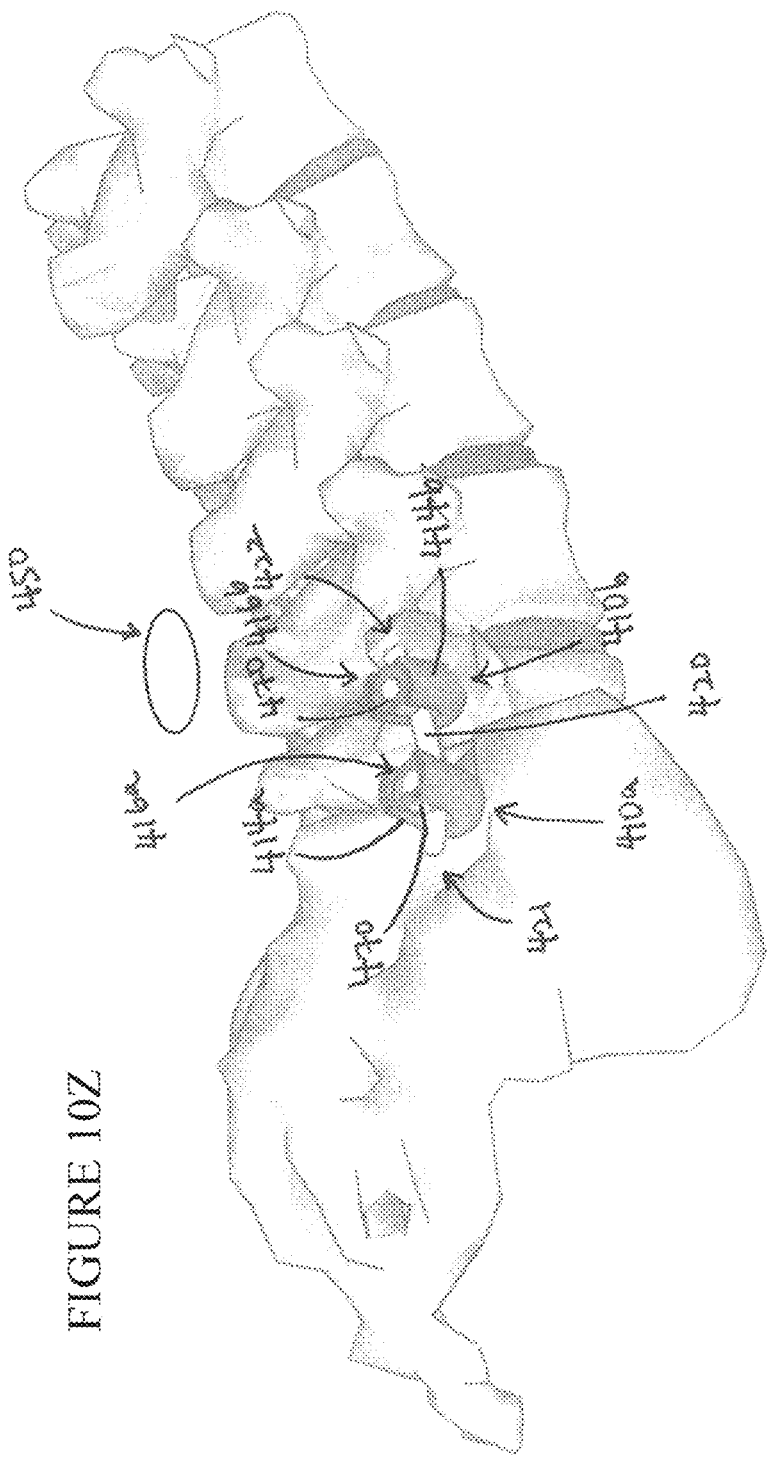

FIGS. 10A-10Z illustrate an embodiment of the method for implanting a plurality of screws into a plurality of vertebrae and the implantation and securement of a rod. The method disclosed in FIGS. 10A-10Z include the screw 410a and screw 410b illustrated above. Although the method illustrated only includes two screws, the disclosed method can be used for any number of screws to be implanted in any number of vertebrae in any order.

FIG. 10A illustrates a first guidewire 460a and a second guidewire 460b that are positioned at a target location on a first and second vertebra. As illustrated, the first guidewire 460a is directed to a vertebrae that is inferior to the vertebrae that the second guidewire 460b is directed to. Each of the first and second guidewires 460a, 460b are configured to directed a first screw 410a and a second screw 410b to their respective vertebrae. As is illustrated in FIG. 10B, the first screw 410a is directed down the first guidewire 460a. As discussed above, the first screw 410a includes a bone engaging shaft 412a and a screw head 414a and a plurality of wires 440a, where at least one wire of the plurality of wires 440a is located on either side of the screw head 414a.

Once the screw 410a is guided to the target location on the first vertebra, as illustrated in FIG. 10D, the bone engaging shaft 412a is screwed into and retained in the first vertebra. As illustrated in FIG. 10E, once the screw 410a is secured, the guidewire 460a is withdrawn out of the body.

FIG. 10E illustrates a perspective view of the implanted first screw 410a. As illustrated, the wires 440a are attached at a distal end to the screw head 414a such that the proximal end of the wires 440a extend out of the incision 450. To prepare for the implantation of the second screw 410b, the plurality of wires 440a are bent away from each other to increase access to the incision 250 (see FIG. 10F).

Similar to the implantation of the first screw 410a, the second screw 410b can be guided to the second vertebra by the second guidewire 460b. In some embodiments, as illustrated in FIG. 10G, the second screw 410b can be inserted with the distal end 439 of the tower 430 retained about the proximal end of the screw head 414b. As will be seen more clearly in subsequent figures, the tower 430 is disposed about the plurality of wires 440b. In some examples, as is illustrated in FIG. 10H, the proximal end of the wires 440b extends from the proximal end 438 of the tower 430.

FIG. 10I illustrates a perspective view of the implanted first screw 410a, the implanted second screw 410b, and the tower 430 disposed about the wires 440b and the screw head 414b of the second screw head 414b. As illustrated, the second guidewire 460b has been removed and the plurality of wires 440a remain bent away from each other to allow access to the window 431 of the tower 430.

FIGS. 10J-10L illustrate the insertion and placement of the rod 420 into the first insert 416a of the first screw 410a and the second insert 416b of the second screw 410b. In some embodiments, the rod 420 (or other implant) can be inserted through the incision 450 and between the bent wires 440a and the window 431 of the tower 430. In some examples, a first end 421 of the rod 420 is passed through the window 431 of the tower 430. The first end 421 can be guided down the window 431 of the tower 430 and the distal end of the wires 440a until it enters the insert 416a of the first screw head 414*a* in the first vertebra. In some examples, the second end 422 of the rod 420 is guided down the window 431 until it enters the insert 416*b* of the second screw head 414*a* in the second vertebra.

In some embodiments, in order to secure the rod 420 in the first screw 410*a* and second screw 410*b*, a locking assembly can be inserted over the rod 420. As discussed in more detail above, the locking assembly may be built into or attached onto the screw head or be a separate element. Locking assemblies that are separate elements include (but are not limited to) those reliant on caps and set screws The locking assembly may be guided down to the screw before or after insertion of the rod depending upon the details of the locking mechanism used to secure the rod. In some embodiments, the locking assembly is already present on the screw head before the rod is received. In some examples, the rod is inserted into the screw head 114 first and the locking assembly follows. In some embodiments, as illustrated in FIGS. 10M and 10N, the locking assembly is a screw cap 470 that can be placed over the rod 420. As illustrated in FIG. 10M, the screw cap 470 can be placed into the opening 433 at the proximal end 438 of the tower 430. The tower 430 is configured to guide the tower 430 into the screw head 414*b* of the screw 410*b* (see FIG. 10N). In some embodiments, the upwardly extending arms of the screw head 414*b* can be internally threaded and the screw cap 470 can be externally threaded. To secure the screw cap 470, the externally threaded screw cap 470 can be rotated into the screw head 414*b* to apply a downward force to the rod 420 sitting in the insert 416*b* of the screw head 414*b*. This downward force can also then lock the second end 422 of the rod 420 such that the screw head 414*b* is secured relative to the rod 420.

In some examples, the tower 430 can be moved from accessing one screw to another screw. FIGS. 10O-10V illustrate the tower 430 moved from accessing the second screw 410*b* to accessing the first screw 410*a*. As shown in FIG. 10O, the tower 430 can be withdrawn in a proximal direction such that the distal end 439 of the tower 430 is disengaged from the proximal end of the second screw head 414*b*. As the tower 430 is withdrawn, the tower 430 is pulled along the length of the wires 440*b* attached to the proximal end of the screw head 414*b* (see FIG. 10P). FIGS. 10Q-10S illustrates a perspective view of the implanted first screw 410*a* and the second screw 410*b*. In some embodiments, in order to allow the tower 430 to be disposed about the plurality of wires 440*a* of the first screw 410*a*, the wires 440*a* can be bent such that the pair of wires 440*a* are brought closer to each other (see FIG. 10R). In some examples, the plurality of wires 440*b* can be bent away from each other to provide additional room and access to the incision 450 (see FIG. 10S).

FIG. 10T illustrates a side view of the implanted first screw 410*a* and the second screw 410*b*. In some embodiments, once the wires 440*a* and wires 440*b* have been bent to accommodate the tower 430, the tower 430 can be disposed about the wires 440*a* of screw 410*a*. As shown in FIGS. 10U and 10V, the tower 430 can be inserted in a distal direction such that the distal end 439 of the tower 430 is disposed about the proximal end of the screw head 414*a*.

As discussed with regard to the insertion of the screw cap 470 into the screw head 414*a* of the screw 410*a*, a second screw cap 470 can be inserted through the opening 433 at the proximal end 438 of the tower 430. As shown in FIGS. 10W and 10X, the second screw cap 470 can be guided to the screw head 414*a* of the screw 410*a*. As discussed above with regard to the first screw cap 470, in some embodiments, the upwardly extending arms of the screw head 414*a* can be internally threaded and the second screw cap 470 can be externally threaded. To secure the second screw cap 470, the externally threaded screw cap 470 can be rotated into the screw head 414*a* to apply a downward force to the rod 420 sitting in the screw head 414*a* of the screw head 414*a*. This downward force can also then lock the first end 421 of the rod 420 such that the screw head 414*a* is secured relative to the rod 420.

Once the first screw 410*a* and the second screw 410*b* are implanted and the rod 420 is secured by the first screw cap 470 and the second screw cap 470, the tower 430 can be withdrawn from the incision 450. In some embodiments, as illustrated in FIG. 10Z, the first pair of wires 440*a* and the second pair of wires 440*b* can be removed from the implanted first screw 410*a* and second screw 410*b*. In some examples, the wires 440*a*, 440*b* are snapped off along with a proximal end of the screw head 414*a*, 414*b*. As shown in FIG. 10Z, in some embodiments, the first screw cap 470 and second screw cap 470 are adjacent to the proximal end of the screw head 414*a*, 414*b*.

In addition to the hybrid systems discussed above, additional hybrid systems that combine any of the guiding elements discussed above are also possible. For example, a system for rod delivery can include a mixture of one blade and one or more wires on a single screw. Another system for rod delivery can include one tube or tower on a first screw and one or more wire or blade combinations on the second screw. Various combinations of guiding elements that can be used through a single incision are possible.

The present disclosure is not limited to the embodiments described above. Various changes and modifications can, of course, be made, without departing from the scope and spirit of the present disclosure.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for bone stabilization, comprising:
   inserting a first screw into a first vertebra, the first screw having a first screw head comprising a first side and a second opposite side, wherein a first guiding element is removably attached to the first screw, the first guiding element comprising a first wire extending from the first side of the first screw head and a second wire extending from the second opposite side of the first screw head;
   inserting a second screw into a second adjacent vertebra, the second screw having a second screw head comprising a first side and a second opposite side, wherein a second guiding element is removably attached to the second screw, the second guiding element comprising a first wire extending from the first side of the second screw head and a second wire extending from the second opposite side of the second screw head,
      wherein the second screw and the second guiding element are inserted into the second adjacent vertebra between the first and second wires of the first guiding element;
   with a third guiding element positioned over the first and second wires of the second guiding element, delivering a spinal fixation element to the first and second screws using at least the first guiding element and the third guiding element;

delivering a first cap to secure a first portion of the spinal fixation element at the second screw, wherein the first cap is delivered using the third guiding element;

removing the third guiding element from the second guiding element;

moving the first and second wires of the first guiding element between the first and second wires of the second guiding element;

sliding the third guiding element over the first guiding element, wherein the third guiding element is moved between the first and second wires of the second guiding element; and delivering a second cap to secure a second portion of the spinal fixation element at the first screw, wherein the second cap is delivered using the third guiding element.

2. The method of claim 1, wherein the third guiding element is positioned between the first and second wires of the first guiding element when the third guiding element is positioned over the first and second wires of the second guiding element.

3. The method of claim 1, wherein the third guiding element is removably coupled with the second screw head when the second screw is inserted into the second adjacent vertebra.

4. The method of claim 1, wherein the third guiding element is a tower.

5. The method of claim 4, wherein the tower comprises a window that extends from a distal end of the tower to a proximal end of the tower.

6. The method of claim 5, wherein the window separates two curved arms of the tower.

7. The method of claim 5, wherein the window is configured to guide the spinal fixation element to the first and second screws.

8. The method of claim 1, wherein at least one of the first and second cap is externally threaded.

9. The method of claim 1, wherein the first cap is configured to be rotated into the first screw head and the second cap is configured to be rotated into the second screw head to apply a downward force to the spinal fixation element.

10. A method for bone stabilization, comprising:

inserting a first screw into a first vertebra, the first screw having a first screw head comprising a first side and a second opposite side, wherein a first guiding element is removably attached to the first screw, the first guiding element comprising a first portion extending from the first side of the first screw head and a second portion extending from the second opposite side of the first screw head;

inserting a second screw into a second adjacent vertebra, the second screw having a second screw head comprising a first side and a second opposite side, wherein a second guiding element is removably attached to the second screw, the second guiding element comprising a first portion extending from the first side of the second screw head and a second portion extending from the second opposite side of the second screw head, wherein the second screw and the second guiding element are inserted into the second adjacent vertebra between the first and second portions of the first guiding element;

after inserting the second screw and the second guiding element, inserting a third guiding element between the first and second portions of the first guiding element and over the second guiding element; and delivering a spinal fixation element to the first and second screws using at least the first guiding element and the third guiding element.

11. The method of claim 10, wherein the first portion of the first guiding element comprises a first wire, and wherein the second portion of the first guiding element comprises a second wire.

12. The method of claim 10, wherein the first portion of the second guiding element comprises a first wire, and wherein the second portion of the second guiding element comprises a second wire.

13. The method of claim 10, wherein the third guiding element comprises a tower.

14. The method of claim 13, wherein the tower includes a window that extends from a distal end of the tower to a proximal end of the tower.

15. The method of claim 14, wherein the window separates two curved arms of the tower.

16. The method of claim 14, wherein the window is configured to guide the fixation element to the first and second screws.

17. The method of claim 10, wherein the third guiding element is guided by the second guiding element.

* * * * *